United States Patent [19]

Guerry et al.

[11] Patent Number: 5,763,450
[45] Date of Patent: Jun. 9, 1998

[54] SUBSTITUTED BENZYL PYRIMIDINES

[75] Inventors: Philippe Guerry, Binningen; Synèse Jolidon, Blauen; Raffaello Masciadri; Henri Stalder, both of Basel, all of Switzerland; Rudolf Then, Weil am Rhein, Germany

[73] Assignee: Hoffmann-La Roche Inc., Nutley, N.J.

[21] Appl. No.: 836,857

[22] PCT Filed: Nov. 13, 1995

[86] PCT No.: PCT/EP95/04451

§ 371 Date: May 21, 1997

§ 102(e) Date: May 21, 1997

[87] PCT Pub. No.: WO96/16046

PCT Pub. Date: May 30, 1996

[30] Foreign Application Priority Data

Nov. 24, 1994 [CH] Switzerland ............... 03 536/94
Sep. 25, 1995 [CH] Switzerland ............... 02 704/95

[51] Int. Cl.$^6$ ............... A61K 31/505; C07D 239/48
[52] U.S. Cl. ............... 514/275; 514/256; 544/324; 544/325
[58] Field of Search ............... 514/256, 275; 544/324, 325

[56] References Cited

PUBLICATIONS

CA121: 271337, 1993.
CA94: 170109, 1980.

*Primary Examiner*—Yogendra N. Gupta
*Attorney, Agent, or Firm*—George W. Johnston; William H. Epstein; John P. Parise

[57] ABSTRACT

Compounds of the formula:

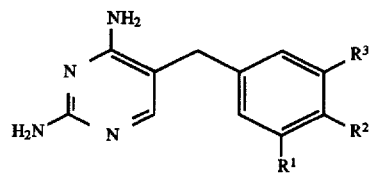

in which $R^1$ is lower alkoxy, $R^2$ is bromine or lower alkoxy, and $R^3$ is aryl, heteroaryl or a group —Q—$R^{30}$, wherein Q is ethylene, vinylene or ethynylene and $R^{30}$ is aryl, heteroaryl, lower alkoxycarbonyl or carbamoyl; hydrolyzable esters of carboxylic acids of formula I; and pharmaceutically acceptable salts of these compounds are useful for treating infectious diseases.

36 Claims, No Drawings

SUBSTITUTED BENZYL PYRIMIDINES

The present invention is concerned with substituted 5-benzyl-2,4-diaminopyrimidines of the general formula

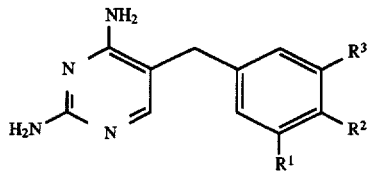

in which $R^1$ represents lower alkoxy, $R^2$ represents bromine or lower alkoxy and $R^3$ represents aryl, heteroaryl or a group —Q—$R^{30}$, wherein Q signifies ethylene, vinylene or ethynylene and $R^{30}$ signifies aryl, heteroaryl, lower alkoxycarbonyl or carbamoyl,
as well as readily hydrolyzable esters of carboxylic acids of formula I and pharmaceutically acceptable salts of these compounds.

These compounds are novel and possess valuable antibiotic properties. They can be used in the control or prevention of infectious diseases. In particular, they exhibit a pronounced antibacterial activity not only against multi-resistant gram-positive strains, but also against opportunistic pathogens such as e.g. *Pneumocystis carinii*. These compounds can also be administered in combination with known antibacterially active substances and then exhibit a synergistic effect. Typical combination partners are e.g. sulphonamides, which can be admixed with the compounds of formula I or their salts in various ratios.

Objects of the present invention are compounds of formula I, their readily hydrolyzable esters and pharmaceutically acceptable salts per se and for use as therapeutically active substances; medicaments based on these substances, optionally in combination with sulphonamides, and their production; the use of these substances as medicaments and for the production of antibacterially-active medicaments; as well as the manufacture of the compounds of formula I and their pharmaceutically acceptable salts and intermediates for their manufacture.

The term "lower" denotes residues and compounds with up to 7, preferably up to 4, carbon atoms. Alkyl and alkoxy residues can be straight-chain or branched, such as e.g. methyl, ethyl, n-propyl, isopropyl and t-butyl and, respectively, methoxy, ethoxy, n-propoxy, isopropoxy and t-butoxy. The same applies to "lower alkyl" as a component of other groups such as lower lower-alkanoyl.

"Aryl" denotes 6-membered aromatic groups which have one or more rings and which preferably have 6–14 carbon atoms. Phenyl, naphthyl, anthryl and phenanthryl are examples. These groups can be substituted, e.g. by phenyl; lower alkyl (e.g. methyl); $C_{3-6}$ cycloalkyl (e.g. cyclopropyl); halogen (e.g. bromine, fluorine); trifluoromethyl; lower alkenyl (e.g. 1-pentenyl); lower alkoxy (e.g. methoxy, n-butoxy); carboxy; lower alkoxycarbonyl (e.g. methoxycarbonyl); hydroxy; oxo; lower alkanoyloxy (e.g. acetoxy); amino; lower alkylamino (e.g. methylamino); di-(lower alkyl)-amino (e.g. dimethylamino, diethylamino); lower alkoxycarbonyl-lower alkylamino (e.g. methoxycarbonylethylamino); carboxy-lower alkylamino (e.g. carboxyethylamino); lower alkanoylamino (e.g. acetylamino); lower alkoxycarbonyl-lower alkanoylamino (e.g. 2-ethoxycarbonyl-acetylamino, 4-methoxycarbonyl-n-butyrylamino); lower alkoxycarbonylbenzoylamino (e.g. 4-methoxycarbonylbenzoylamino); hydroxybenzoylamino; carboxy-lower alkanoylamino (e.g. 2-carboxyacetylamino, 4-carboxy-n-butyrylamino); carboxybenzoylamino (e.g. 4-carboxybenzoylamino); mono- or di-(heterocyclylcarbonyl)amino (e.g. furan-2-carbonylamino); aminobenzenesulphonyl (e.g. 4-aminobenzenesulphonyl); sulphamoyl; hydroxyiminomethyl; aminobenzenesulphonylamino (e.g. 4-aminobenzenesulphonylamino); aryl-lower alkyl (e.g. benzyl); heteroaryl-lower alkyl (e.g. 2,4-diaminopyrimidin-5-ylmethyl); arylamino (e.g. 3-chloro-1,4-dioxo-1,4-dihydro-naphthalen-2-ylamino); nitro-lower alkylamino, e.g. (2-nitro-ethyl)amino; carboxy-lower alkenyl, e.g. 2-carboxyvinyl; lower-alkyloxycarbonyl-lower-alkenyl, e.g. 2-methoxycarbonylvinyl; formyl, cyano, hydroxy-lower-alkyl, e.g. hydroxymethyl; di-(lower-alkoxycarbonyl)-lower-alkenyl, e.g. di-(ethoxycarbonyl) vinyl; —C(O)C(CH-lower-alkoxy)COOH; —C(O)C(NOH)COOH; —C(O)C(NOH)CO—O-lower-alkyl; —C(O)C(NO-trityl)CO—O-lower-alkyl; —C(O)C(NO-lower-alkyl)COO-lower-alkyl; —C(O)C(NO-lower-alkoxy-lower-alkyl)CO-O-lower-alkyl; —C(O)C(CHN-(lower-alkyl)$_2$)CO—O-lower-alkyl; mono- or di-(lower-alkyl or cycloalkyl) carbonylamino, e.g. N-cyclopropylcarbonyl-N-acetyl-amino; cyano-lower-alkylcyclopropyl-carbonyl-amino, e.g. (2-cyano)ethyl-cyclopropyl-carbonylamino; lower-alkanoyl, e.g. acetyl; cyclopropyl-carbonyl; lower-alkoxy-lower-alkoxy, e.g. methoxy-methoxy; lower-alkoxycarbonyl-lower-alkanoyl, e.g. ethoxycarbonyl-acetyl; trifluoromethyl-sulphonylamino; lower-alkylsulphonylamino-carbonyl; tetrahydropyranylamino; lower-alkoxycarbonyl-lower-alkanoyl; N-tetrahydropyranyl-N-lower-alkanoylamino; N-lower-alkanoyl-N-heterocyclylcarbonylamino, such as N-cyclopropyl-N-furoylamino; lower-alkylaminocarbonyl, such as cyclopropylaminocarbonyl; lower-alkoxycarbonylamino-lower-alkyl-carbonylamino; N-lower-alkoxyphenyl-lower-alkyl-N-trifluoromethylsulphonylamino, such as N-(p-methoxybenzyl)-trifluorosulphonylamino; N-lower-alkyl-trifluorosulphonylamino; amino-lower-alkylarbonylamino; —P(O)(O-lower-alkyl)$_2$; P(O)(O-lower-alkyl)OH, —P(O)(OH)$_2$; N-(carboxy-lower-alkyl) trifluoromethylsulphonylamino, such as N-(carboxymethyl) trifluoromethylsulphonylamino; N-(lower-alkoxycarbonyl-lower-alkyl)trifluoromethylsulphonylamino, such as N-(ethoxycarbonylmethyl)trifluoromethylsulphonylamino; —C(O)NHCH(heterocyclyl)$_2$, such as di-(α-pyridyl) methylaminocarbonyl; or aminophenyl-sulphonylamino, or by
a group of the general formula

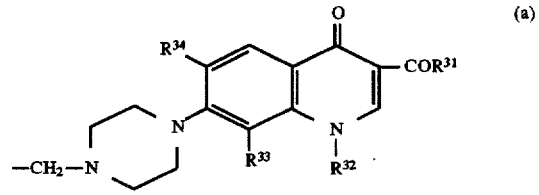

(a)

in which $R^{31}$ represents hydroxy, lower-alkoxy, e.g. methoxy or ethoxy, amino, (hydroxy-lower-alkyl) amino, di-lower-alkylamino-lower-alkoxy or morpholino-lower-alkoxy, $R^{32}$ represents hydrogen, lower-alkyl, e.g. methyl, ethyl, tert.-butyl, 1,1,3,3-tetramethylbutyl, hydroxy-lower-alkyl, e.g. hydroxyethyl, 2-hydroxy-1,1-dimethylethyl and 2,3,4,5,6-pentahydroxyhexyl; phenyl, cyclohexyl, aminocyclohexyl, cyclopentyl, cyclopropyl cyclopropylmethyl, 2,2,2-trifluoroethyl, pyridylmethyl, piperidylmethyl, adamantyl, bicyclo[2.2.1]hept-2-yl, 2-(tert.-butyl-dimethylsilanyloxy)-1,1-dimethylethyl, 2-(2-(2-hydroxyethoxy)ethoxy)ethyl, furylmethyl, tetrahydrofurylmethyl, tetrahydropyranyl, or aryl-lower-alkyl, such as benzyl; and $R^{33}$ and $R^{34}$ each independently represent hydrogen, fluorine, hydroxy or methoxy.

4-(1-Cyclopropyl-3-ethoxycarbonyl-6,8-difluoro-4-oxo-1,4-dihydro-7-quinolinyl)-1-piperazinylmethyl) is an example of a group (a).

"Heteroaryl" denotes 5- or 6- membered heteroaromatic groups which contain one or more rings and which preferably have 5–13 carbon atoms and 1–4 hetero atoms, preferably N, O and/or S. Furyl, pyranyl, thienyl, pyrrolyl, pyrazolyl, imidazolyl, triazolyl, tetrazolyl, oxazolyl, oxadiazolyl, isoxazolyl, thiazolyl, isothiazol, pyridyl, pyridazinyl, pyrimidinyl, pyrazinyl and triazinyl are examples. These groups can also be linked with a fused ring, preferably a phenyl ring, e.g. benzopyranyl, benzofuranyl, indolyl and quinolinyl. The "heteroaryl groups" can also be further substituted, for example as described above for the "aryl groups".

Preferred groups $R^3$ are groups of the formulae

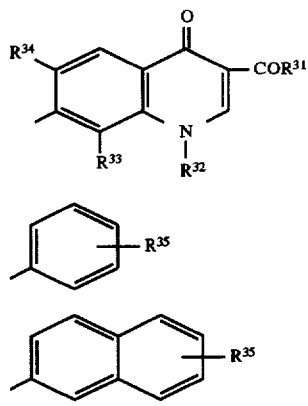

(b)

(c)

(d)

in which $R^{31}$–$R^{34}$ have the significances given above for group (a) and $R^{35}$ represents hydrogen, hydroxy or carboxy.

$R^{31}$ is preferably hydroxy; $R^{32}$ is preferably cyclohexyl, cyclopropyl, benzyl or tert.-butyl; and $R^{33}$ is preferably hydrogen or fluorine. $R^{34}$ is preferably hydrogen or fluorine. Q is preferably vinylene or ethynylene. $R^1$ and $R^2$ are preferably methoxy.

Preferred compounds of formula I are:

1-Cyclohexyl-7-[5-(2,4-diamino-pyrimidin-5-ylmethyl)-2,3-dimethoxy-phenylethynyl]-4-oxo-1,4-dihydro-quinoline-3-carboxylic acid, 5-(3,4-dimethoxy-5-naphthalen-2-yl-benzyl)-pyrimidine-2,4-diamine, 5-(3,4-dimethoxy-5-naphthalen-6-hydroxy-2-yl-benzyl) pyrimidine-2,4-diamine, 5-(4'-carboxyl-5,6-dimethoxy-biphenyl-3-ylmethyl) pyrimidine-2,4-diamine, 5-(3'-hydroxy-5,6-dimethoxy-biphenyl-3-ylmethyl) pyrimidine-2,4-diamine, 1-cyclopropyl-7-[5-(2,4-diamino-pyrimidin-5-ylmethyl)-2,3-dimethoxy-phenyl]-6-fluoro-4-oxo-1,4-dihydro-quinoline-3-carboxylic acid, 1-cyclopropyl-7-[5-(2,4-diamino-pyrimidin-5-ylmethyl)-phenyl]-6-fluoro-4-oxo-1,4-dihydro-quinoline-3-carboxylic acid, 1-cyclopropyl-7-[5-(2,4-diamino-pyrimidin-5-ylmethyl)-2-methoxy-phenyl]-6-fluoro-4-oxo-1,4-dihydro-quinoline-3-carboxylic acid, 5-[3,4-dimethoxy-5-(2-naphthalen-2-yl-vinyl)-benzyl]-pyrimidine-2,4-diamine, ethyl 1-ethyl-7-[5-(2,4-diamino-pyrimidin-5-ylmethyl)-2,3-dimethoxy-phenylethynyl]-4-oxo-1,4-dihydro-quinoline-3-carboxylate, 1-ethyl-7[5-(2,4-diamino-pyrimidin-5-ylmethyl)-2,3-dimethoxy-phenylethynyl]-4-oxo-1,4-dihydro-quinoline-3-carboxylic acid, 5-[3,4-dimethoxy-5-(2-naphthalen-6-carboxy-2-yl-ethynyl)-benzyl]-pyrimidine-2,4-diamine, 1-cyclopropyl-7-[5-(2,4-diamino-pyrimidin-5-ylmethyl)-2,3-dimethoxy-phenylethynyl-1]-6,8-difluoro-4-oxo-1,4-dihydro-quinoline-3-carboxylic acid, 1-cyclopropyl-7-[5-(2,4-diamino-pyrimidin-5-ylmethyl)-2,3-dimethoxy-phenylethynyl-1]-6-fluoro-4-oxo-1,4-dihydro-quinoline-3-carboxylic acid, 1-benzyl-7-[5-(2,4-diamino-pyrimidin-5-ylmethyl)-2,3-dimethoxy-phenylethynyl]-1-methyl-4-oxo-1,4-dihydro-quinoline-3-carboxylic acid, 1-tert-butyl-7-[5-(2,4-diamino-pyrimidin-5-ylmethyl)-2,3-dimethoxy-phenylethynyl]-4-oxo-1,4-dihydro-quinoline-3-carboxylic acid as well as pharmaceutically acceptable salts of these compounds.

The compounds of formula I form pharmaceutically acceptable acid addition salts with organic and inorganic acids. Examples of acid addition salts of compounds of formula I are salts with mineral acids, for example hydrohalic acids such as hydrochloric acid, hydrogen bromide and hydrogen iodide, sulphuric acid, nitric acid, phosphoric acid and the like, salts with organic sulphonic acids, for example with alkyl- and arylsulphonic acids such as methanesulphonic acid, p-toluenesulphonic acid, benzenesulphonic acid and the like as well as salts with organic carboxylic acids, for example with acetic acid, tartaric acid, maleic acid, citric acid, benzoic acid, salicylic acid, ascorbic acid and the like.

The compounds of formula I—insofar as they contain a carboxyl or phenolic hydroxy group—also form pharmaceutically acceptable salts with bases. Examples of such salts of compounds of formula I are the alkali metal salts, for example the sodium and potassium salts, the ammonium salts, the salts with organic basis, for example with amines such as diisopropylamine, benzylamine, dibenzylamine, triethanolamine, triethylamine, N,N-dibenzylethylenediamine, N-methylmorpholine, pyridine, piperazine, N-ethylpiperidine, N-methyl-D-glucamine and procaine or with amino acids such as arginine and lysine.

The readily hydrolyzable esters of compounds of formula I are carboxylic acid esters, i.e. esters of compounds of formula I in which $R^3$ contains a free carboxy group. These are preferably esters which can be hydrolyzed under mild conditions, especially those which can be hydrolyzed enzymatically under physiological conditions. Examples of such esters, which can be of the conventional type, are the 1-(lower alkanoyloxy)-lower alkyl esters, e.g. the acetoxymethyl, pivaloyloxymethyl, 1-acetoxyethyl and 1-pivaloyloxyethyl esters, the 1-(lower alkoxycarbonyloxy) lower alkyl esters, e.g. the (methoxycarbonyloxy)methyl, 1-(ethoxycarbonyloxy)ethyl and 1-(isopropoxycarbonyloxy)ethyl esters, the lactonyl esters, e.g. the phthalidyl and thiophthalidyl esters, the 1-(lower alkoxy)-lower alkyl esters, e.g. the methoxymethyl esters, the 1-(lower alkanoylamino)-lower alkyl esters, e.g. the acetamidomethyl esters, the benzyl esters, the cyanomethyl esters and the (2-oxo-1,3-dioxol-4-yl)methyl esters.

The compounds of formula I and their pharmaceutically acceptable salts can be manufactured in accordance with the invention by a) reacting a compound of the general formula

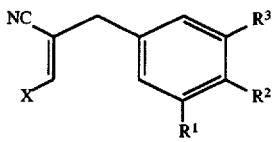

II in which $R^1$, $R^2$ and $R^3$ have the above significance, with any phenolic hydroxy groups present being protected, and X represents a leaving group, with guanidine and cleaving off protecting groups present, or b) for the manufacture of compounds of formula I in which $R^3$ represents aryl or N-heteroaryl, reacting a compound of the general formula

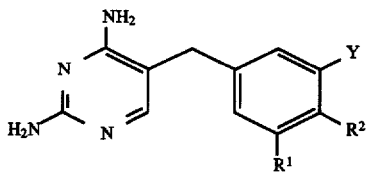

III with a compound of the general formula $R^{36}Z$  IV in which $R^1$ and $R^2$ have the above significance and $R^{36}$ represents aryl or N-heteroaryl, with any phenolic hydroxy groups present being protected, one of the symbols $Y^1$ and Z represents a leaving group and the other represents a group which is eliminated with this leaving group, and cleaving off protecting groups present, or c) for the manufacture of compounds of formula I in which $R^3$ represents the group —Q—$R^{30}$ with Q=vinylene or ethynylene, reacting a compound of the general formula

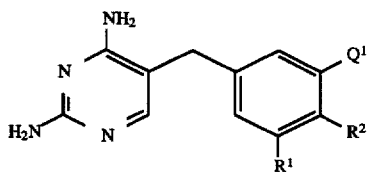

V with a compound of the general formula $R^{30}Q^2$  VI in which $R^1$, $R^2$ and $R^{30}$ have the above significance, with any phenolic hydroxy groups present being protected, one of the symbols $Q^1$ and $Q^2$ represents a group which is eliminated and the other represents vinyl or ethynyl, and cleaving off protecting groups present, or d) for the manufacture of compounds of formula I in which $R^3$ represents the group —Q—$R^{30}$ with Q=ethylene or vinylene, appropriately reducing a compound of the general formula

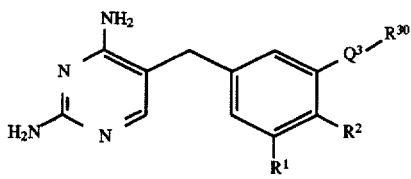

Ia in which $R^1$, $R^2$ and $R^{30}$ have the above significance and $Q^3$ represents vinylene or ethynylene, or e) saponifying or hydrolyzing a carboxylic acid ester group present in $R^3$ in a compound of formula I, or f) converting a carboxylic acid group present in $R^3$ in a compound of formula I into a readily hydrolyzable ester group, or g) converting a compound of formula I into a pharmaceutically acceptable salt.

The cyclization of the starting materials II with guanidine in accordance with variant a) of the process in accordance with the invention is preferably carried out in an inert organic solvent, preferably in a lower alkanol, e.g. ethanol, or in dimethyl sulphoxide, tetrahydrofuran or dioxan, and at about 50° to 100° C. The guanidine is preferably used as a salt, e.g. as the hydrochloride, in which case the reaction is preferably carried out in the presence of a base, e.g. potassium t-butylate.

In the reaction of the compounds III and IV in accordance with variant b) of the process in accordance with the invention there are to be understood under eliminating groups leaving groups Y and, respectively, Z which react with one another and accordingly both "eliminate" with the formation of an eliminating byproduct. Many possibilities present themselves to a person skilled in the art in this respect; the following embodiments are mentioned as examples:

Y=bromine, iodine, methylsulphonyloxy, trifluoromethylsulphonyloxy, phenylsulphonyloxy, p-tosylsulphonyloxy;

Z=(OH)$_2$B—.

This reaction with a (N-hetero)-arylboric acid IV, also known as a "Suzuki coupling", is preferably effected in an inert organic solvent such as e.g. dioxan or tetrahydrofuran at a temperature between about 20° C. and the boiling point of the reaction mixture. Preferably, a base such as an alkali metal carbonate, e.g. potassium carbonate, is preferably added as well as a catalyst, preferably a palladium complex such as tetrakis-triphenylphosphine-palladium.

A (N-hetero)-aryl-metal compound with Z=—Sn(lower-alkyl)$_3$, e.g. —Sn(CH$_3$)$_3$ or —Sn(n-butyl)$_3$ ("Stille reaction"); —MgHal ("Grignard coupling"); or —ZnHal and Hal=bromine or iodine can be used in the above reaction as the reaction partner IV. No base is used in this reaction, although the catalyst described above is preferably used. It can also be advantageous to add an inert salt, especially lithium chloride.

The aforementioned reaction can also be carried out with interchanged substituents Y and Z, e.g. with Y=—Sn(CH$_3$)$_3$, —MgHal or —ZnHal and Z=bromine, iodine, methylsulphonyloxy, trifluoromethylsulphonyloxy, phenylsulphonyloxy, p-tosylsulphonyloxy. The reaction conditions are essentially the same.

A so-called "Heck reaction" is carried out for the manufacture of compounds of formula I in which $R^3$ represents a group —Q—R³⁰ and Q=vinylene or ethynylene by e.g. reacting a starting material of formula V in which Q¹ represents bromine, iodine, methylsulphonyloxy, trifluoromethylsulphonyloxy, phenylsulphonyloxy or p-tosylsulphonyloxy with a compound of general formula VI in which Q² represents vinyl or ethynyl. An inert organic solvent, e.g. dioxan, tetrahydrofuran or dimethylformamide, is preferably used. The reaction is preferably effected in the presence of a base such as an alkali metal carbonate, e.g. potassium carbonate, or a tertiary amine, e.g. in a tri-(lower-alkyl)-amine such as triethylamine or tri-n-butyl-amine, as well as together with a catalayst, preferably a palladium complex such as palladium(II) acetate, tetrakis-triphenylphosphinepalladium, or copper(I) iodide and triphenylphosphine, optionally with the addition of a phase transfer catalyst such as a tetraalkylammonium salt, e.g. tetramethylammonium chloride. The temperature at which the "Heck reaction" is carried out preferably lies in the range between about 40° C. and the boiling point of the reaction mixture.

The "Heck reaction" can also be carried out with interchanged substituents Q¹ and Q², i.e. by reacting a starting material of formula V in which Q¹ represents vinyl or ethynyl with a compound of general formula VI in which Q² represents e.g. bromine, iodine, methylsulphonyloxy, trifluoromethylsulphonyloxy, phenylsulphonyloxy or p-tosylsulphonyloxy. The reaction conditions are essentially the same.

In accordance with variant d) the unsaturated group Q³ in compound V is further saturated; in particular, Q³ as vinylene is converted into ethylene or as ethynylene is converted into vinylene or ethylene. This reduction is effected, for example, by catalytic hydrogenation with palladium-charcoal (e.g. 5–10%) at about 20° C. to about 60° C. in a lower alkanol such as methanol. For the complete hydrogenation (Q=ethylene), a higher amount of palladium-charcoal (about 10–15%) is preferably used and the hydrogenation is carried out in an organic carboxylic acid such as acetic acid in a non-polar solvent such as dimethylformamide or dimethyl sulphoxide.

A carboxylic acid ester group present in R³ in a compound of formula I is saponified or hydrolyzed in accordance with variant e) of the process in accordance with the invention. This is especially the case when a quinoline group substituted by esterified carboxy in the 3-position, such as a corresponding group esterified at carboxy in the case of the above group (a) or in the case of the above group (b), is present. The saponification in accordance with the invention is effected in alcoholic solution with alkali, e.g. with an alkali metal hydroxide (potassium, lithium or sodium hydroxide) or an alkali metal carbonate (potassium or sodium carbonate). The hydrolysis is effected in acidic medium by treatment with a mineral acid, e.g. hydrochloric or sulphuric acid in aqueous or aqueous/alcoholic solution. The temperature at which the saponification or hydrolysis is carried out lies in the range between room temperature and the boiling point of the reaction mixture.

Phenolic hydroxy groups are preferably protected in a preproduct stage, preferably using silyl groups, e.g. trimethylsilyl, t-butyldimethylsilyl. These are advantageously introduced by treatment with the corresponding silyl chloride. The cleavage can be effected by the action of a fluoride, preferably [an] alkali metal fluoride or tetrabutylammonium fluoride, in an organic solvent, e.g. dimethylformamide or acetonitrile, at about 0° C. to 50° C.

The phenolic hydroxy groups can also be protected by lower alkanoyl groups, e.g. acetyl. Introduction is e.g. by treatment with a lower alkanoyl halide or anhydride, e.g. the chloride, in the presence of a base such as sodium hydroxide, DBU or diisopropylethylamine. The cleavage is effected under mild alkaline conditions (pH about 7–8), e.g. with sodium hydroxide or carbonate, at about 0° to 50° C.

For the manufacture of the readily hydrolyzable esters of the carboxylic acids of formula I in accordance with variant f), the carboxylic acid is preferably reacted with the corresponding halide, preferably with the iodide, which contains the ester group. The reaction can be accelerated with the aid of a base, e.g. an alkali metal hydroxide, alkali metal hydrogen carbonate or carbonate or an organic amine such as triethylamine, 1,8-diazabicyclo[5.4.0]undec-7-ene (DBU) or tetramethylguanidine. This reaction is preferably carried out in an inert organic solvent such as dimethylacetamide, hexamethylphosphoric acid triamide, dimethyl sulphoxide or, preferably, dimethylformamide. The temperature preferably lies in the range of about 0° to 40° C.

The manufacture of the salts of the compounds of formula I in accordance with variant g) can be effected in a manner known per se, e.g. by reacting a carboxylic acid of formula I with an equivalent amount of the desired base, conveniently in a solvent such as water or in an organic solvent such as ethanol, methanol or acetone. Acid addition salt formation is likewise brought about by addition of an organic or inorganic acid. The temperature at which the salt formation is carried out is not critical. It generally lies at room temperature, but can also readily be thereunder or thereover, for example in the range of 0° C. to +50° C.

The starting materials of formula II can be prepared in accordance with the Reaction Scheme hereinafter:

Reaction Scheme

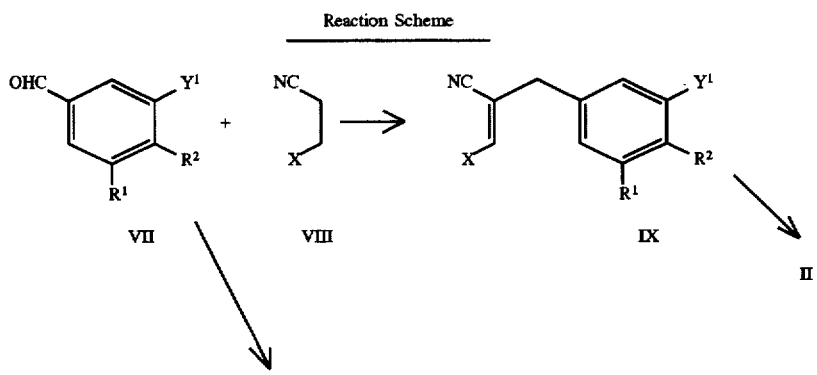

-continued
Reaction Scheme

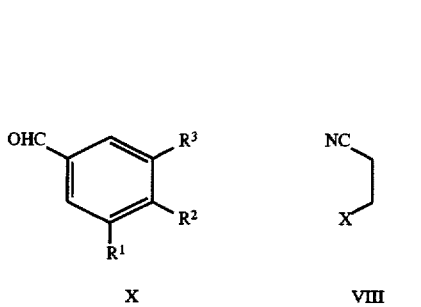

X                    VIII

In the above Reaction Scheme $R^1$, $R^2$ and X have the above significance. $Y^1$ signifies a leaving group, e.g. bromine, chlorine, methylsulphonyloxy, trifluoromethylsulphonyloxy, p-toluenesulphonyloxy or phenylsulphonyloxy.

VII+VIII→IX; X+VIII→II

This condensation is preferably carried out in an inert organic solvent, e.g. in dioxan, or, preferably, in dimethyl sulphoxide, at about 20° C. to 100° C. in the presence of a strong base, e.g. potassium t-butylate or sodium hydride.

VII→X; IX→II

These aryl couplings are carried out in the same manner as described above for process variant b). If desired, the coupling VII→X can be effected while acetalizing the aldehyde group. The aldehyde VII is thereby preferably acetalized in an inert solvent such as benzene or toluene in the presence of an excess of an alcohol such as ethanol, ethylene glycol or 2,2-dimethylpropanediol and an acid catalyst such as sulphuric acid or p-toluenesulphonic acid in a temperature range of 80° C. to 120° C. while separating water. After introduction of the group $R^3$ in the desired manner the acetal group is converted into the aldehyde group, preferably by treatment with an aqueous, dilute mineral acid, e.g. hydrochloric acid and an organic solvent such as dioxan or ethanol at about 0° to 100° C.

The starting materials of formula III in which Y represents a leaving group are known compounds. (Y=Br: U.S. Pat. No. 3,878,252; Y=I: Arzneimittelforschung (1982), 32 (7) 711–714; Y=substituted sulphonyloxy: from the corresponding 3-hydroxy compound III—Arch. Pharm. Chem., Sci. Ed. 1983, 11, 1–6—and a sulphonic acid) or can be prepared in an analogous manner to the known compounds. Starting materials of formula V are prepared in an analogous manner as for the "Heck reaction" described above under process variant b), with mono-protected acetylene or ethylene, preferably ethynyl-trimethylsilane or vinyl-trimethylsilane, being subjected to a Heck reaction and the protecting group in the reaction product being subsequently cleaved off. Trimethylsilyl is cleaved off e.g. by alkali fluoride in an organic solvent such as dimethylformamide at room temperature. If desired, tetrabutylammonium fluoride in acetonitrile can be used.

The temperature preferably lies between about 0° C. and 50° C.

As mentioned earlier, the compounds of formula I and their pharmaceutically acceptable salts possess valuable antibacterial properties. They are active against a large number of pathogenic microorganisms such as e.g. *Staphylococcus areus, Pneumocystis carinii* etc. by virtue of their action in inhibiting bacterial dihydrofolate reductase (DHFR).

The inhibition of the enzyme was taken as a measurement for the antibacterial activity. It is determined using the method of Baccanari and Joyner (Biochemistry 20, 1710 (1981)); see also P. G. Hartman et al., FEB 242, 157–160 (1988).

The $IC_{50}$ values (concentration at which the enzyme is inhibited to 50%) are determined graphically.

The following Table contains inhibitory concentrations determined in the above test for representative members of the class of compound defined by formula I. The $C_{50}$ values (µM) are given against the purified DHFR of the reference strain *S. aureus* ATCC 35923 as well as against the purified DHFR of the multi-resistant strain *S. aureus* 157/4696. The third column shows the $IC_{50}$ values (µM) of the purified DHFR of the opportunistic pathogen *P. carinii*. The inhibition constants of trimethoprim are also given as a comparison.

| End product from Example No. | S. aureus ATCC 25923 | S. aureus 157/4696 | P. carinii |
|---|---|---|---|
| 4h | 0.0022 | 1.3000 | 1.6000 |
| 5b | 0.0040 | 2.2000 | 2.3000 |
| 5c | 0.0009 | 0.4200 | 0.4800 |
| 5h | 0.0013 | 0.5000 | 1.0000 |
| 9a | 0.0009 | 0.0500 | 0.0190 |
| 9b | 0.0002 | 0.1100 | 0.0380 |
| 9c | 0.0019 | 0.2100 | 0.2000 |
| 10b | 0.0200 | 0.7500 | 4.0000 |
| 12g | 0.0050 | 0.1300 | 0.9000 |
| 15a | 0.0150 | 0.7000 | 8.0000 |
| 16c | 0.0012 | 0.0024 | 0.0360 |
| 16e | 0.0029 | 0.0800 | 3.4000 |
| 16f | 0.0015 | 0.0065 | 0.2800 |
| 16j | 0.0009 | 0.0240 | 5.0000 |
| 16p | 0.0012 | 0.0013 | 0.14 |
| 16ac | 0.0009 | 0.0016 | 0.1900 |
| Trimethoprim | 0.0340 | 16.0000 | 43.0000 |

The products in accordance with the invention can be used as medicaments, e.g. in the form of pharmaceutical preparations for enteral or parenteral administration. The products in accordance with the invention can be administered, for example, perorally, e.g. in the form of tablets, coated tablets, dragées, hard and soft gelatine capsules, solutions, emulsions or suspensions, rectally, e.g. in the form of suppositories, or parenterally, e.g. in the form of injection solutions.

The production of the pharmaceutical preparations can be effected in a manner which will be familiar to any person skilled in the art by bringing the substances in accordance with the invention, if desired in combination with other therapeutically valuable substances, into a galenical administration form together with suitable, non-toxic, inert, therapeutically compatible solid or liquid carrier materials and, if desired, the usual pharmaceutical adjuvants.

Not only inorganic carrier materials, but also organic carrier materials are suitable as such carrier materials. Thus, lactose, corn starch or derivatives thereof, talc, stearic acid or its salts can be used, for example, as carrier materials for tablets, coated tablets, dragées and hard gelatine capsules. Suitable carriers for soft gelatine capsules are, for example, vegetable oils, waxes, fats and semi-solid and liquid polyols (depending on the nature of the active substance no carriers are, however, required in the case of soft gelatine capsules). Suitable carrier materials for the production of solutions and syrups are, for example, water, polyols, sucrose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

The usual preservatives, solubilizers, stabilizers, wetting agents, emulsifiers, sweeteners, colorants, flavorants, salts for varying the osmotic pressure, buffers, coating agents and antioxidants come into consideration as pharmaceutical adjuvants.

For parenteral administration the compounds of formula I and, respectively their salts are preferably provided as lyophilizates or dry powders for dilution with conventional carriers such as water or isotonic saline.

As already mentioned, the compounds of formula I and their salts have antibacterial activity. They inhibit bacterial dihydrofolate reductase and potentiate the antibacterial activity of sulphonamides such as e.g. sulfisoxazole, sulfadimethoxine, sulfamethoxazole, 4-sulphanilamido-5,6-dimethoxy-pyrimidine, 2-sulphanilamido-4,5-dimethyl-pyrimidine or sulfaquinoxaline, sulfadiazine, sulfamonomethoxine, 2-sulphanilamido-4,5-dimethyl-isoxazole and other inhibitors of enzymes which are involved in folic acid biosynthesis, such as e.g. pteridine derivatives.

Oral, rectal and parenteral administration come into consideration for the treatment of hosts, especially warm-blooded hosts, e.g., in human medicine, with the compounds of formula I or combinations thereof with sulphonamides. A daily dosage of about 0.2 g to about 2 g of a compound of formula I in accordance-with the invention comes into consideration for adults. When administered in combination with antibacterial sulphonamides the ratio of compound I to sulphonamide can vary within a wide range; it amounts to e.g. between 1:40 (parts by weight) and 1:1 (parts by weight); 1:10 to 1:2 are preferred ratios. Thus, e.g. a tablet can contain 80 mg of a compound I in accordance with the invention and 400 mg of sulfamethoxazole, a tablet for children can contain 20 mg of a compound I in accordance with the invention and 100 mg of sulfamethoxazole; syrup (per 5 ml) can contain 40 mg of compound I and 200 mg of sulfamethoxazole.

The compounds of formula I are characterized by a high antibacterial activity and, respectively, a pronounced synergistic effect in combination with sulphonamides and good tolerance.

The following Examples illustrate the invention. The temperatures are given in degrees Celsius.

EXAMPLE 1

Preparation of aryl-metal compounds IV

1a) A solution of 19.6 g of bromobenzene in 250 ml of tetrahydrofuran is treated dropwise at −78° over 2 hrs. with 94 ml of a 1.6M butyllithium solution in n-hexane. The solution is stirred for a further 2 hrs. at −78°, then treated dropwise at this temperature with a solution of 30 g of trimethyltin chloride in 100 ml of tetrahydrofuran. The mixture is stirred at room temperature for a further 3 hrs. and then poured on to ice. After extraction with diethyl ether the organic phase is dried over magnesium sulphate, evaporated and the residue is chromatographed on silica gel with n-hexane/ethyl acetate 98:2. 2.95 g (10%) of trimethyl-phenyl-stannate are isolated as a colourless oil. Mass spectrum: peaks: inter alia at m/e: 227 (M+, 100%), 197 (32%).

1b) In analogy to Example 1a), from 1-bromo-4-fluorobenzene there is obtained trimethyl-4-fluorophenyl-stannate as a colourless oil. Yield: 42%. Mass spectrum: peaks: inter alia at m/e: 245 (M±methyl, 100%), 215 (28%), 169 (42%).

1c) According to J. Heterocycl. Chem. 27, 1841 (1990), from 4-chloro-2,6-dimethylpyridine and sodium trimethyl-stannate there is obtained trimethyl-4-(2,6-dimethyl-pyridinyl)-stannate as a colourless liquid. Yield: 53%. B.p. 105°–107°/1700 Pa. Mass spectrum: peaks: inter alia at m/e: 269 (M+, 8%), 256 (100%), 252 (M±methyl, 45%).

1d) In analogy to Example 1a), from 5-bromopyrimidine there is obtained trimethyl-5-pyrimidinyl-stannate as a yellowish oil. Yield: 10%. Mass spectrum: peaks: inter alia at m/e: 229 (M±methyl, 100%), 199 (20%).

1e) In analogy to Example 1a), from 3-bromopyridine there is obtained trimethyl-3-pyridinyl-stannate as a yellowish oil. Yield: 18%. Mass spectrum: peaks: inter alia at m/e: 228 (M±methyl, 100%), 149 (66%), 106 (86%), 93 (40%), 92(40%).

1f) In analogy to Example 1a), from 4-bromo-(dimethyl-t-butyl-silyl-oxy)-benzene there is obtained trimethyl-4-(dimethyl-t-butylsilyl-oxy)-phenyl-stannate as a colourless oil.

Yield: 97%. Mass spectrum: peaks: inter alia at m/e: 356 (M±methyl, 100%), 341 (26%), 207 (43%).

1g) In analogy to Example 1a), from 4-bromopyridine there is obtained trimethyl-4-pyridinyl-stannate as a yellowish oil. Yield: 33%. Mass spectrum: peaks: inter alia at m/e: 228 (M±methyl, 100%), 198 (36%), 135 (26%), 51 (48%).

1h) In analogy to Example 1a), from 3-bromo-(dimethyl-t-butyl-silyl-oxy)-benzene there is obtained trimethyl-3-(dimethyl-t-butyl-silyl-oxy)-phenyl-stannate as a yellowish oil. Yield: 77%.-Mass spectrum: peaks: inter alia at m/e: 357 (M±methyl, 100%), 165 (34%), 135 (20%).

1i) In analogy to Example 1a), from 4-bromo-n-butoxy-benzene there is obtained trimethyl-4-n-butoxy-phenyl-stannate as a yellowish oil. Yield: 32%. Mass spectrum: peaks: inter alia at m/e: 299 (M±methyl, 100%), 107 (22%).

1j) In analogy to Example 1a), from 4-bromo-(1-pentenyl)-benzene there is obtained trimethyl-4-(1-pentenyl)-phenyl-stannate as a yellowish oil. Yield: 47%. Mass spectrum: peaks: inter alia at m/e: 295 (M±methyl, 100%), 265 (24%), 263 (22%).

1k) 1.0 g of methyl 4-iodo-benzoate, 1.18 ml of hexam-ethyldistannate and 44 mg of tetrakis-triphenylphosphine-palladium are dissolved in 25 ml of dioxan and held at reflux for 2 hrs. The mixture is poured into saturated sodium chloride solution and extracted with diethyl ether. The organic phase is dried over magnesium sulphate and, after concentration, chromatographed on silica gel with n-hexane/ethyl acetate 95:5. 1.04 g (92%) of trimethyl-4-methoxycarbonyl-phenyl-stannate are isolated as a colourless oil. Mass spectrum: peaks: inter alia at m/e: 285 (M±methyl, 100%), 255 (30%), 253 (26%).

1l) In analogy to Example 1k), from methyl 3-iodobenzoate there is obtained trimethyl-3-methoxycarbonylphenyl-stannate as a colourless oil. Yield: 41%. Mass spectrum: peaks: inter alia at m/e: 285 (M±methyl, 28%), 183 (14%).

1m) In analogy to Example 1k), from 4-bromobiphenyl there is obtained trimethyl-4-biphenylyl-stannate as a yellowish oil. Yield: 64%. Mass spectrum: peaks: inter alia at m/e: 303 (M±methyl, 100%), 299 (46%), 152 (30%).

1n) In analogy to Example 1k), from 4-iodo-trifluoromethylbenzene there is obtained trimethyl-4-trifluoromethyl-phenyl stannate as a yellowish oil. Yield: 51%. Mass spectrum: peaks: inter alia at m/e: 295 (M±methyl, 100%), 107 (48%).

1o) In analogy to Example 1k), from 5-(5-iodo-3,4-dimethoxybenzyl)-pyrimidine-2,4-diamine there is obtained 5-(3,4-dimethoxy-5-trimethylstannyl-benzyl)-pyrimidine-2,4-diamine as a colourless solid. Yield: 26%. M.p. 203°.

1p) 1.0 g of ethyl 7-iodo-1,4-dihydro-4-oxo-quinoline-3-carboxylate, 1.68 ml of hexa-n-butyidistannate and 34 mg of tetrakis-triphenylphosphine-palladium in 3 ml of dimethylformamide and 10 ml of triethylamine are heated at 100° C. for 20 hrs. The mixture is concentrated in a high vacuum. The residue is triturated with 10 ml of ethyl acetate/n-hexane 1:1, filtered off from insoluble material and chromatographed on silica gel with ethyl acetate/n-hexane 1:1. 1.13 g (78%) of ethyl 7-(tri-n-butyl-stannyl)-1,4-dihydro-4-oxo-quinoline-3-carboxylate are isolated as a yellowish oil. Mass spectrum: peaks: inter alia at m/e: 544 (M+, 3%), 478 (92%), 422 (46%), 366 (100%).

1q) In analogy to Example 1a), from 3,4-dimethoxybromobenzene there is obtained trimethyl-3,4-trimethoxyphenyl-stannate as a colourless oil. Yield: 23%. Mass spectrum: peaks: inter alia at m/e: 287 (M±CH$_3$, 100%), 285 (78%), 257 (38%).

EXAMPLE 2

Preparation of compounds of formula I (couplings according to Stille)

2a) 138 mg of 5-(3-bromo-4,5-dimethoxy-benzyl)-pyrimidine-2,4-diamine, 98 mg of trimethyl-phenyl-stannate (Example 1a), 51 mg of lithium chloride, 25 mg of tetrakis-triphenylphosphinepalladium and a crystal of 2,6-di-t-butyl-p-cresol in 10 ml of dioxan are held at reflux under argon for 4 hrs. The yellowish reaction mixture is poured into about 10% aqueous ammonia and extracted three times with methylene chloride. The organic phase is dried over magnesium sulphate and chromatographed on silica gel with methylene chloride/methanol 9:1. 62 mg (46%) of 5-(5,6-dimethoxy-biphenyl-3-ylmethyl)-pyrimidine-2,4-diamine are isolated as a yellowish solid. Mass spectrum: peaks: inter alia at m/e: 336 (M+, 100%), 321 (28%), 305 (54%), 123 (36%).

2b) In analogy to Example 2a), with trimethyl-4-fluorophenylstannate (Example 1b) there is obtained 5-(4'-fluoro-5,6-dimethoxy-biphenyl-3-ylmethyl)-pyrimidine-2,4-diamine as a colourless solid. Yield: 19%. Mass spectrum: peaks: inter alia at m/e: 354 (M+, 100%), 339 (34%), 323 (44%), 123 (34%).

2c) In analogy to Example 2a), with trimethyl-4-(2,6-dimethylpyridinyl)-stannate (Example 1c) there is obtained 5-(3,4-dimethoxy-5-(2,6-dimethyl-4-pyridinyl)-benzyl)-pyrimidine-2,4-diamine as a colourless solid. Yield: 30%. M.p. 176°.

2d) In analogy to Example 2a), with trimethyl-5-pyrimidinylstannate (Example 1d) there is obtained 5-(3,4-dimethoxy-5-(5-pyrimidinyl)-benzyl)-pyrimidine-2,4-diamine as a yellowish solid. Yield: 74%. M.p. 240° (decomposition).

2e) In analogy to Example 2a), with trimethyl-3-pyridinyl-stannate (Example 1e) there is obtained 5-(3,4-dimethoxy-5-(3-pyridinyl)-benzyl)pyrimidine-2,4-diamine as a yellowish solid. Yield: 33%. M.p. 89° (decomposition).

2f) In analogy to Example 2a), with trimethyl-4-(dimethyl-t-butylsilyloxy)-phenyl-stannate (Example 1f) there is obtained 5-(4'-t-butyl-dimethylsilyloxy-5,6-dimethoxy-biphenyl-3-yl-methyl)-pyrimidine-2,4-diamine as a colourless solid. Yield: 42%. M.P. 173°.

2g) in analogy to Example 2a), with trimethyl-4-pyridinyl-stannate (Example 1g) there is obtained 5-(3,4-dimethoxy-5-(4-pyridinyl)-benzyl-pyrimidine-2,4-diamine as a colourless solid. Yield: 56%. Mass spectrum: peaks: inter alia at m/e: 337 (M+, 100%), 322 (72%), 306 (62%), 123 (54%).

2h) In analogy to Example 2a), with trimethyl-3-(dimethyl-t-butyl-silyl-oxy)-phenyl-stannate (Example 1h) there is obtained 5-(3'-t-butyl-dimethylsilyloxy-5,6-dimethoxy-biphenyl-3-ylmethyl)-pyrimidine-2,4-diamine as a yellowish solid. Yield: 70%. Mass spectrum: peaks: inter alia at m/e: 466 (M+, 50%), 409 (100%), 123 (24%).

2i) in analogy to Example 2a), with trimethyl-4-methoxycarbonylphenyl-stannate (Example 1k) there is obtained 5-(4'-methoxycarbonyl-5,6-dimethoxy-biphenyl-3-ylmethyl)-pyrimidine-2,4-diamine as a colourless solid. Yield: 49%. M.p. 133°.

2k) In analogy to Example 2a), with trimethyl-3-methoxycarbonylphenyl-stannate (Example 1l) there is obtained 5-(3'-methoxycarbonyl-5,6-dimethoxy-biphenyl-3-ylmethyl)-pyrimidine-2,4-diamine as a colourless solid. Yield: 40%. M.p. 83°.

2l) In analogy to Example 2a), with trimethyl-4-biphenylylstannate (Example 1m) there is obtained 5-(4'-phenyl-5,6-dimethoxy-biphenyl-3-ylmethyl)-pyrimidine-2,4-diamine as a colourless solid. Yield: 22%. M.p. 188°.

2m) In analogy to Example 2a), with trimethyl-4-trifluoromethyl-phenyl-stannate (Example 1n) there is obtained 5-(4'-trifluoromethyl-5,6-dimethoxy-biphenyl-3-ylmethyl)pyrimidine-2,4-diamine as a colourless solid. Yield: 35%. Mass spectrum: peaks: inter alia at m/e: 404 (M+, 100%), 389 (42%), 373 (44%), 123 (28%).

2n) 0.89 g 5-(3,4-dimethoxy-5-iodo-benzyl)-pyrimidine-2,4-diamine and trimethyl-4-n-butoxy-phenyl-stannate (Example 1i) are dissolved in 50 ml of dioxan, treated with 0.36 g of lithium chloride and 0.18 g of tetrakis-triphenylphosphine-palladium and held at reflux under argon for 14 hrs. The mixture is poured on to ice-water, extracted with methylene chloride and dried over magnesium sulphate. After evaporation the residue is chromatographed on silica gel with methylene chloride/methanol 9:1. 23 mg (4%) of 5-(4'-butyloxy-5,6-dimethoxy-biphenyl-3-ylmethyl)-pyrimidine-2,4-diamine are isolated as a colourless solid. Mass spectrum: peaks: inter alia at m/e: 408 (M+, 100%), 377 (24%), 321 (22%), 123 (38%).

2o) In analogy to Example 2n), with trimethyl-4-(1-pentenyl)phenyl-stannate (Example 1j) there is obtained 5-(4'-pentenyl-5,6-dimethoxy-biphenyl-3-ylmethyl)-pyrimidine-2,4-diamine as a colourless solid. Yield: 19%. Mass spectrum: peaks: inter alia at m/e: 404 (M+, 100%), 389 (34%), 373 (36%), 123 (40%).

2p) 1.0 g of 5-(3,4-dimethoxy-5-trimethylstannyl-benzyl) -pyrimidine-2,4-diamine (Example 1o) and 0.472 g of 4-bromobenzamide are dissolved in 50 ml of dioxan, treated with 0.3 g of lithium chloride and 0.15 g of tetrakis-triphenylphosphine-palladium and held at reflux under argon for 14 hrs. The mixture is poured on to ice-water, extracted with methylene chloride, dried over magnesium sulphate and, after concentration, the residue is chromatographed on silica gel with methylene chloride/methanol 2:1. 64 mg (7%) of 5-(4'-carbamoyl-5,6-dimethoxy-biphenyl-3-ylmethyl)-pyrimidine-2,4-diamine are isolated as a colourless solid. M.p. 199° (decomposition).

2q) In analogy to Example 2p), with 4-(4-bromophenylsulphonyl)-aniline there was obtained 5-(4'-(4-amino-benzene sulphonyl)-5,6-dimethoxy-biphenyl-3-ylmethyl)-pyrimidine-2,4-diamine as a yellowish solid. Yield: 4%. Mass spectrum (FAB): peaks: inter alia at m/e: 492 (M++H, 100%).

2r) In analogy to Example 2p), with 4-bromo-t-butylbenzene there was obtained 5-(4'-t-butyl-5,6-dimethoxy-biphenyl-3-ylmethyl)-pyrimidine-2,4-diamine as a colourless solid. Yield: 9%. Mass spectrum: peaks: inter alia at m/e: 392 (M+, 100%), 377 (64%), 361 (42%), 123 (32%).

2s) In analogy to Example 2p), with 4-bromo-benzenesulphonamide there was obtained 5-(4'-sulphamoyl-5,6-dimethoxybiphenyl-3-ylmethyl)-pyrimidine-2,4-diamine as a colourless solid. Yield: 12%. M.p. 207°.

2t) 216 mg of 5-(3,4-dimethoxy-5-iodo-benzyl)-pyrimidine-2,4-diamine, 300 mg of 7-(tri-n-butyl-stannyl)-1-ethyl-1,4-dihydro-4-oxo-quinoline-3-carboxylate (Example 1p) and 40 mg of bis-triphenylphosphine-palladium dichloride in 5 ml of dimethylformamide are held at reflux under argon for 30 hrs. The yellow reaction mixture is poured into 50 ml of water and extracted three times with 50 ml of methylene chloride. The organic phase is dried on magnesium sulphate, concentrated and the residue is chromatographed on silica gel with methylene chloride/methanol 4:1. 88 mg (31%) of ethyl 7-[5-(2,4-diaminopyrimidin-5yl-methyl)-2,3-dimethoxy-phenyl]-1-ethyl-1,4-dihydro-4-oxo-quinoline-3-carboxylate are isolated as a yellowish solid. M.p. 139° (dec.).

2u) In analogy to Example 2t), from 5-(3-iodo-4-methoxybenzyl)-pyrimidine-2,4-diamine [Eur. J. Med. Chem. (Chim. Ther.) 1982, 17, 497] and ethyl 7-(tri-n-butyl-stannyl)-1,4-dihydro-4-oxo-quinoline-3-carboxylate (Example 1p) there is obtained ethyl 7-[5-(3-diamino-pyrimidin-5yl-methyl)-2-methoxy-phenyl]-1-ethyl- 1,4-dihydro-4-oxo-quinoline-3-carboxylate as a yellowish solid. Yield: 23%. M.p. 157° (dec.).

2v) In analogy to Example 2a), from trimethyl-(3,4-dimethoxyphenyl)-stannate (Example 1q) there is obtained 5-(3',4',5,6-tetramethoxy-biphenyl-3-ylmethyl)-pyrimidine-2,4-diamine as a colourless solid. Yield: 35%. M.p. 208°–210°.

EXAMPLE 3

Preparation of arylboric acids IV

3a) A solution of the corresponding Grignard compound is prepared from 16.8 g 4-bromo-N,N-dimethyl-aniline and 2.04 g of magnesium in 150 ml of tetrahydrofuran. This is now slowly added dropwise while stirring at −60° to a solution of 9.4 ml of trimethylborate in 50 ml of tetrahydrofuran under argon. Subsequently, the mixture is stirred at room temperature overnight. The mixture is poured on to ice-water, adjusted to pH 3–4 with dilute sulphuric acid and extracted with diethyl ether. The extract is dried, evaporated and the residue is recrystallized from water. 5.6 g (40%) of 4-dimethylamino-phenylboric acid are obtained. Mass spectrum: peaks inter alia at m/e: 164 (M±H, 100%).

3b) In analogy to Example 3a), from 4-bromo-N,N-diethylaniline there is obtained 4-diethylamino-phenylboric acid. Yield: 14%. Mass spectrum: peaks: inter alia at m/e: 193 (M+, 28%), 178 (100%), 106 (22%).

3c) 1.86 g of 3-aminophenyl-boric acid hemisulphate are suspended are suspended in 20 ml of water and treated with 5 ml of a 2N sodium hydroxide solution. The clear, yellowish solution is treated dropwise while cooling with ice with a solution of monoethyl malonyl chloride in 7 ml of tetrahydrofuran. The mixture is stirred at room temperature for a further 15 min. and the precipitate is filtered off under suction. It is recrystallized in 50 ml of water. 1.12 g (45%) of 3-(2-ethoxycarbonylacetylamino)-phenylboric acid are isolated. M.p. 247°.

3d) In analogy to Example 3c), with 4-nitrobenzenesulphochloride there is obtained 3-(4-nitrobenzene-sulphonylamino)phenylboric acid. Yield: 77%. M.p. 135°–145° (decomposition).

3e) In analogy to Example 3c), with 2-furoyl chloride there is obtained 3-((furan-2-carbonyl)-amino-phenylboric acid. Yield: 94%. M.p. 320°.

3f) In analogy to Example 3c), with monomethyl glutaryl chloride there is obtained 3-(4-methoxycarbonyl-n-butyrylamino)-phenylboric acid. Yield: 83%. Mass spectrum (FAB): peaks: inter alia at m/e: 264 (M±H, 100%), 232 (65%), 188 (20%).

3 g) In analogy to Example 3c), with monomethyl terephthaloyl chloride there is obtained 3-(((4'-methoxycarbonyl)-benzoyl)amino)-phenylboric acid. Yield: 85%. Mass spectrum (FAB): peaks: inter alia at 298 (M±H, 100%), 254 (255%).

3h) In analogy to Example 3a), with 2-bromo-6-(t-butyl-dimethyl-silyloxy)-naphthalene there is obtained 6-(t-butyl-dimethyl-silyloxy)-2-naphthylboric acid. Yield: 40%. Mass spectrum (FAB): peaks: inter alia at 301 (M±H, 75%), 187 (100%).

3i) In analogy to Example 3c), with O-acetylsalicyloyl chloride there is obtained 3-(2-acetoxybenzoylamino)-phenylboric acid. Yield: 92%. Mass spectrum (FAB): peaks: inter alia at 256 (M+acetyl, 100%), 238 (10%).

3j) 1.2 g of 3-aminophenyl-boric acid hemisulphate are suspended in 20 ml of water and treated with 3.2 ml of a 2N sodium hydroxide solution. The clear solution is treated with 1.67 g of methyl acrylate in 15 ml of dioxan. The mixture is heated to reflux under argon for 48 hrs. Subsequently, it is poured on to ice-water, extracted with ethyl acetate, dried, concentrated and the residue is chromatographed on silica gel with ethyl acetate/cyclohexane 1:1. 500 mg (35%) of not quite pure 3-(2-methoxycarbonylethylamino)-phenylboric acid are isolated as a brown resin. Mass spectrum (FAB): peaks: inter alia at 222 (M±H), 190 (8%).

3k) 1.14 g of 2,3-dichloro-1,4-naphthoquinone (sic) and 0.93 g of 3-aminophenyl-boric acid hemisulphate are suspended in 40 ml of ethanol and treated with 0.9 g of sodium acetate. The mixture is stirred at room temperature for 1hr., then heated to 60° for 2 hrs. The residue is filtered off under suction and washed with 10 ml of ice-water. 1.38 g (84%) of 3-(3-chloro-1,4-dioxo-1,4-dihydro-naphthalen-2-ylamino)-phenylboric acid are thus isolated as an orange-red solid. M.p>270°. Mass spectrum (FAB): peaks: inter alia at 326 (M±H), 282 (28%), 246 (20%).

3l) 1.0 g of ethyl 1-cyclopropyl-6,8-difluoro-4-oxo-1,4-dihydro-7-(piperazin-1-yl)-quinoline-3-carboxylate (German Offenlegungsschrift 3,525,108, C.A. 106:176189) and 0.57 g of 4-(bromo-methyl)-phenyl-boric acid (J. Am. Chem. Soc. 80, 835, 1958) are treated with 1.41 g of sodium carbonate in 25 ml of dimethylformamide. The reaction mixture is stirred at room temperature for 4 hrs., then poured into 150 ml of water and adjusted to pH 6 with 2N hydrochloric acid. The mixture is extracted twice with 100 ml of methylene chloride each time, the organic phase is dried over magnesium sulphate and concentrated. The crude product is triturated with 10 ml of ether, filtered off under suction and dried. 961 mg of ethyl 1-cyclopropyl-7-[4-(4-dihydroxyboro-phenylmethyl)-piperazin-1-yl]-6,8-difluoro-4-oxo-1,4-dihydro-quinolinecarboxylate are obtained as a yellowish solid. M.p.>173° C. (dec.). Mass spectrum (ISP) peaks: inter alia at 510.3 ((M−H)+, 100%).

3m) 900 mg of 4-formyl-benzeneboric acid (Lancaster) were dissolved in 15 ml of DMSO, treated with 3.05 g of methoxycarbonyl-methylene-triphenylphosphorane and stirred at room temperature under Ar for 30 min. The mixture is poured on to ice-water, made acid with dilute hydrochloric acid and extracted with ethyl acetate. Chromatography on silica gel with ethyl acetate/hexane yields 550 mg (44%) of 4-(3-acrylic acid methyl ester)-phenyl boric acid as a colourless solid. This is used in Example 4r) without further characterization.

3n) 450 mg of 4-formyl-benzeneboric acid (Lancaster) and 625 mg of hydroxylamine hydrochloride are stirred at room temperature overnight in 15 ml of water. The colourless precipitate is filtered off under suction and dried in a high vacuum. 490 mg of the oxime of 4-formyl-benzeneboric acid are isolated. Yield: 99%. M.p.= 228°–230°.

3o) 3.98 g of 5-bromoindole in 40 ml of tetrahydrofuran were treated at 0° under argon with 4 g of a 20 percent potassium hydride suspension in oil. After 15 min, the mixture is cooled to −78° and treated slowly with 27 ml of a 1.5M solution of t-butyllithium in pentane. After 10 min. at −78° a solution of 4.5 ml trimethyl borate in 10 ml of tetrahydrofuran is added dropwise. The mixture is warmed to room temperature and subsequently poured into 150 ml of an ice-cold 1M phosphoric acid solution. The mixture is extracted 3 times with ether. The organic phases are washed 3 times with 15 ml of 1M sodium hydroxide solution and dried over magnesium sulphate. After concentration the residue is chromatographed on silica gel (methylene chloride/methanol 9:1). 834 mg of indole-5-boric acid are isolated as a yellowish solid. Yield: 25%. M.p.=245° (decomposition).

3p) 14 g of furfural diethyl acetal (H.Scheibler et al., Ber. 57, 1443 (1924)) are dissolved in 30 ml of ether and the solution is cooled to −40°. Thereafter, a 1.6M solution of butyllithium in hexane is slowly added dropwise. The mixture is stirred at room temperature for 2 hrs. and subsequently again cooled to −40°. A solution of 11 ml of trimethyl borate in 50 ml of ether is now added dropwise thereto. The mixture is warmed to room temperature and then held at reflux for a further 0.5 hr. The mixture is poured into ice-cold 2N hydrochloric acid and extracted 3 times with ethyl acetate The organic phase is washed 3 times with saturated sodium carbonate solution and dried over magnesium sulphate. After evaporation the residue is recrystallized from water. 3.0 g of fural-(2-formyl)-5-boric acid are isolated as a colourless solid. Yield: 26%. M.p.=140°–142°.

3q) 1g of fural-(2-formyl)-5-boric acid (Example 3p) is dissolved in 17 ml of tetrahydrofuran and treated with 2.4 g of methoxycarbonyl-methylene-triphenylphosphorane. The orange mixture is stirred at room temperature for 3 hrs., thereafter poured on to ice-water and extracted with ethyl acetate. The crude methyl 3-(5-boric acid-furan-2-yl)-acrylate obtained after evaporation is used in Example 4w) without further purification.

3r) 0.5 g of fural-(2-formyl)-5-boric acid (Example 3p) and 0.74 g of hydroxylamine hydrochloride are stirred at room temperature overnight with the addition of 0.98 g of sodium acetate in 18 ml of water. The mixture is partly concentrated and the resulting precipitate is filtered off under suction and dried. There is thus obtained 0.233 g of the oxime of fural-(2-formyl)-5-boric acid as a light yellowish solid. Yield: 42%. M.p.=168°–171°.

3s) In an analogy to Example 3p), from 2,2'-bifuranyl (T.Kauffmann, Chem. Ber. 114, 3667 (1981)) there is obtained 2,2'-bifuranyl-5-boric acid as a yellowish oil. Yield: 29%. This is used in Example 4aa) without further characterization.

3t) 450 mg of 5-(4-bromophenyl)-1H-tetrazole (J. W. Tilley et al, J. Med. Chem. 34, 1125 (1991)) is suspended in 20 ml of THF and the suspension is cooled to −78°. 3 ml of a 15M solution of t-butyllithium in pentane is added dropwise thereto while stirring and the mixture is stirred at −78° for 15 min. Thereafter, 0.56 g of trimethyl borate is added thereto and the mixture is slowly warmed to room temperature. There is obtained a clear, colourless solution which is concentrated to about one half in a rotary evaporator at 45°. It is treated with 50 ml of 1N hydrochloric acid and the separated, unreacted 5-(4-bromophenyl)-1H-tetrazole is filtered off under suction. The mother liquor is held in a refrigerator overnight, a 3:1 mixture (mass spectrum) of 5-(4-boric acid phenyl)-1H-tetrazole and 5-1H-tetrazole separating. This mixture is used in Example 4ab) without further purification.

3u) 450 mg of 4-formyl-benzeneboric acid and 1.2 g of diethyl malonate are held at reflux for 2 hrs. in a mixture of 15 ml of pyridine and 0.5 ml of piperidine. The mixture is poured into 100 ml of 3N hydrochloric acid and extracted 3 times with ethyl acetate. Chromatography on silica gel with ethyl acetate gives 260 mg of yellowish diethyl 2-(4-boric acid-benzylidene)malonate. Yield: 30%. M.p. 146°–148°.

EXAMPLE 4

Preparation of compounds of formula I (couplings according to Suzuki)

4a) 376 mg of 5-(3,4-dimethoxy-5-iodo-benzyl)-pyrimidine-2,4-diamine and 400 mg of 4-dimethylamino-phenylboric acid (Example 3a)) are treated with 40 ml of dioxan and 2.4 ml of a 2M potassium carbonate solution and 24 mg of tetrakis-tri-phenylphosphine-palladium. The mixture is heated at reflux under argon for 14 hrs. Subsequently, it is poured on to ice-water, extracted with methylene chloride, dried over magnesium sulphate and chromatographed on silica gel with methylenechloride/methanol 98:2. 327 mg (91%) of 5-(4'-dimethylamino-5,6-dimethoxy-biphenyl-3-ylmethyl)-pyrimidine-2,4-diamine are isolated as a yellowish solid. M.p. 230°.

4b) In analogy to Example 4a) with 4-diethylamino-phenylboric acid (Example 3b)) there is obtained 5-(4'-diethylamino-5,6-dimethoxy-biphenyl-3-ylmethyl)-pyrimidine-2,4-diamine as a yellowish solid. Yield: 39%. M.p. 227°.

4c) In analogy to Example 4a), with phenyl-1,4-diboric acid (J.Chem.Soc. (C) 1970, 488) there are obtained, after chromatography, two different compounds:

5-(4'-Boric acid-5,6-dimethoxy-biphenyl-3-ylmethyl) pyrimidine-2,4-diamine as a yellowish solid. Yield: 41%. M.p. >270°. Mass spectrum (FAB): peaks: inter alia at 381 (M++H, 100%);

1,4-bis-(5-(2,4-diamino-pyrimidin-5-ylmethyl)-2,3-dimethoxy-phenyl)-benzene as a colourless solid. Yield: 28%. M.p.>270°. Mass spectrum (FAB): peaks: inter alia at 595 (M++H, 100%), 336 (75%).

4d) In analogy to Example 4a), with 3-aminophenyl-boric acid there is obtained 5-(3'-amino-5,6-dimethoxy-biphenyl-3-yl-methyl)-pyrimidine-2,4-diamine as a yellowish solid. Yield: 74%. M.p. 87°–91°.

4e) In analogy to Example 4a), with 3-(2-ethoxycarbonyl-acetylamino)-phenylboric acid (Example 3c)) there is obtained 5-(3 '-(2-ethoxycarbonyl-acetylamino)-5,6-dimethoxy-biphenyl-3-ylmethyl)-pyrimidine-2,4-diamine as a colourless solid. Yield: 12%. M.p.>260°. Mass spectrum (FAB): peaks: inter alia at 466 (M++H, 100%).

4f) In analogy to Example 4a), with 3-(4-nitrobenzene-sulphonylamino)-phenylboric acid (Example 3d)) there is obtained 5-(3'-(4-nitrobenzene-sulphonylamino)-5,6-dimethoxy-biphenyl-3-ylmethyl)-pyrimidine-2,4-diamine as a yellowish solid. Yield: 73%. M.p.>260°. Mass spectrum (FAB): peaks: inter alia at 535 (M±H, 100%).

4g) In analogy to Example 4a), with 1-naphthyl-boric acid there is obtained 5-(3,4-dimethoxy-5-naphthalen-1-yl-benzyl)pyrimidine-2,4-diamine as a colourless solid. Yield: 97%. Mass spectrum: peaks: inter alia at 386 (M+, 100%), 371 (18%), 355 (34%), 123 (44%).

4h) In analogy to Example 4a), with 2-naphthyl-boric acid there is obtained 5-(3,4-dimethoxy-5-naphthalen-2-yl-benzyl)pyrimidine-2,4-diamine as a colourless solid. Yield: 51%. Mass spectrum: peaks: inter alia at 386 (M+, 100%), 371 (22%), 355 (32%), 123 (36%).

4i) In analogy to Example 4a), with 3-((furan-2-carbonyl)amino-phenylboric acid (Example 3e)) there is obtained 5-(3'-furan-2-carbonylamino)-5,6-dimethoxy-biphenyl-3-ylmethyl)pyrimidine-2,4-diamine as a colourless solid. Yield: 53%. M.p. 280°.

4j) In analogy to Example 4a), with 3-(4-methoxycarbonyl-n-butyrylamino)-phenylboric acid (Example 3f)) there is obtained 5-(3'-(4-methoxycarbonyl-n-butyrylamino)-5,6-dimethoxybiphenyl-3-ylmethyl)-pyrimidine-2,4-diamine as a colourless solid. Yield: 59%. M.p. 210°.

4k) In analogy to Example 4a), with 3-(((4'-methoxycarbonyl)benzoyl)-amino)-phenylboric acid (Example 3 g)) there is obtained 5-(3'-(4-methoxycarbonyl-benzoyl)-amino)-5,6-dimethoxybiphenyl-3-ylmethyl)-pyrimidine-2,4-diamine as a colourless solid. Yield: 13%. Mass spectrum (FAB): peaks: inter alia at 541 (M±H, 100%), 353 (40%), 331 (75%).

4l) In analogy to Example 4a), with 6-(t-butyl-dimethyl-silyloxy)-2-naphthylboric acid (Example 3h)) there is obtained 5-(3,4-dimethoxy-5-naphthalen-6-(t-butyl-dimethyl-silyloxy)-2-yl-benzyl)-pyrimidine-2,4-diamine as a colourless solid. Yield: 53%. Mass spectrum: peaks: inter alia at 516 (M+, 100%), 459 (66%).

4m) In analogy to Example 4a), with ³-(2-acetoxy-benzoylamino)-phenylboric acid (Example 3i)) there is obtained N-{5'-(2,4-diamino-pyrimidin-5-ylmethyl)-2',3'-dimethoxy-biphenyl-3-yl}-2-hydroxy-benzamide, which is converted with potassium hydroxide solution into the corresponding potassium salt (the O-acetyl group is cleaved off during the normal working up). Yield: 21%. Mass spectrum (FAB): peaks: inter alia at 472 (M++H, 100%).

4n) In analogy to Example 4a), with 3-(2-methoxycarbonylethylamino)-phenylboric acid (Example 3j)) there is obtained 5-(3'-(2-methoxycarbonylethyl-amino)-5,6-dimethoxy-biphenyl-3-ylmethyl)-pyrimidine-2,4-diamine as a colourless solid which is not quite pure. The compound is used in Example 5i) without further purification.

4o) In analogy to Example 4a), with 3-(3-chloro-1,4-dioxo-1,4-dihydro-naphthalen-2-ylamino)-phenylboric acid (Example 3k)) there is obtained 2-chloro-3-[5'-(2,4-diamino-pyrimidin-5-ylmethyl)-2',3'-dimethoxy-biphenyl-3-ylamino][1,4]-naphthoquinone as an orange solid. Yield: 41%. M.p. 248°–252°.

4p) In analogy to Example 4a), with ethyl with 1-cyclopropyl-7-[4-(4-dihydroxyboro-phenylmethyl)-piperazin-1-yl]-6,8-difluoro-4-oxo-1,4-dihydro-quinolinecarboxylate (Example 31)) there is obtained ethyl 1-cyclopropyl-7-[4-[5'-(2,4-diamino-pyrimidin-5-ylmethyl)-2',3'-dimethoxy-biphenyl-4-ylmethyl]piperazin-1-yl]-6,8-difluoro-4-oxo-1,4-dihydro-quinoline-3-carboxylate as a yellowish solid. Yield: 81%. M.p.>145° C. (dec.). Mass spectrum (ISP): peaks: inter alia at 726.4 (M++H, 6%), 364.2 (100%).

4q) In analogy to Example 4a), with 2-furylboric acid (D.Florentin et al., Bull. Soc. Chim. France 1976, 1999) there is obtained 5-(3-furan-2-yl-4,5-dimethoxy-benzyl)-pyrimidine-2,4-diamine as a colourless solid. Yield: 83%. M.p.=205°.

4r) In analogy to Example 4a), with 4-(3-acrylic acid methyl ester)-phenylboric acid (Example 3m)) there is obtained methyl 3-[5'-(2,4-diamino-pyrimidin-5-ylmethyl)-2',3'-dimethoxy-biphenyl-4-yl]-acrylate as a yellowish solid. This is reacted in Example 5n) without further purification.

4s) In analogy to Example 4a), with the oxime of 4-formylbenzeneboric acid (Example 3n)) there is obtained 5'-(2,4-diamino-pyrimidin-5-ylmethyl)-2',3'-dimethoxy-biphenyl-4-carbaldehyde oxime as a yellowish solid. Yield: 23%; M.p.=238°–239°.

4t) In analogy to Example 4a), with 4-formyl-benzeneboric acid there is obtained 5'-(2,4-diamino-pyrimidin-5-ylmethyl)-2',3'-dimethoxy-biphenyl-4-carbaldehyde as a colourless solid. Yield: 84%; M.p.=99°.

4u) In analogy to Example 4a), with indole-5-boric acid (Example 3o)) there is obtained 5-[3-(1H-indol-5-yl)-4,5-dimethoxy-benzyl]-pyrimidine-2,4-diamine as a beige solid. Yield: 93%. Mass spectrum (ISP): peaks inter alia at m/e: 377 (18%), 376 (M+, 100%). 4v) In analogy to Example 4a), with 2-benzofuryl-boric acid (GLAXO, GB 9102114) there is obtained 5-(3-benzofuran-2-yl-4,5-dimethoxy-benzyl)-pyrimidine-2,4-diamine as a colourless solid. Yield: 28%. M.p.=94°.

4w) In analogy to Example 4a), with methyl 3-(5-boric acid-furan-2-yl)-acrylate (Example 3q) there is obtained methyl 3-[5-[5-(2,4-diaminopyrimidin-5-ylmethyl)-2,3-dimethoxyphenyl]furan-2-yl-acrylate as a yellowish solid. Yield: 65%. Mass spectrum (ISP): peaks inter alia at m/e: 410 (M+, 100%), 363 (40%), 123 (11%).

4x) In analogy to Example 4a), with the oxime of furyl-(2-formyl)-5-boric acid (Example 3r) there is obtained 5-[5-(2,4-diamino-pyrimidin-5-ylmethyl)-2,3-dimethoxy-phenyl]-furan-2-carbaldehydeoxime as a beige solid. Yield : 32%. M.p.=237°–240°.

4y) In analogy to Example 4a), with furyl-(2-formyl)-5-boric acid (Example 3p)) there is obtained 5-[5-(2,4-diamino-pyrimidin-5-ylmethyl)-2,3-dimethoxy-phenyl]-furan-2-carbaldehyde as a yellowish solid. Yield: 12%. Mass spectrum (ISP): peaks inter alia at m/e: 354 (M+, 100%).

4z) In analogy to Example 4a), with 3-furylboric acid (D.Florentin et al., Bull. Soc. Chim. France 1976, 1 999)

there is obtained 5-(3-furan-3-yl-4,5-dimethoxy-benzyl)-pyrimidine-2,4-diamine as a yellowish solid. Yield: 91%. Mass spectrum (ISP): peaks inter alia at m/e: 326 (M+, 100%), 311 (30%), 295 (32%).

4aa) In analogy to Example 4a), with 2,2'-bifuranyl-5-boric acid (Example 3s)) there is obtained 5-(3-[2,2']-bifuranyl-5-yl-4,5-dimethoxy-benzyl)-pyrimidine-2,4-diamine as a yellowish solid. Yield: 5%. M.p.=1950 (decomposition).

4ab) In analogy to Example 4a), with the impure 5-(4-boric acid phenyl)-1H-tetrazole from Example 3t)) there is obtained 5-[5,6-dimethoxy-4'-(1H-tetrazol-5-yl)-biphenyl-3-ylmethyl]-pyrimidine-2,4-diamine as a colourless solid. Yield: 8%. Mass spectrum (ISP): peaks inter alia at m/e: 405 (M±H, 100%); 329 (30%), 261 (10%), 206 (35%).

4ac) In analogy to Example 42) with 2-(4-boric acid-benzylidene)-malonate (Example 3u)) there is obtained diethyl 2-[5'-(2,4-diamino-pyrimidin-5-ylmethyl)-2',3'-dimethoxy-biphenyl-4-ylmethylene]-malonate as a yellowish solid. Yield: 41%. M.p.=77°–80°.

EXAMPLE 5

Transformation of compounds of type I 5a) 267 mg of 5-(4'-t-butyl-dimethylsilyloxy-5,6-dimethoxybiphenyl-3-ylmethyl)-pyrimidine-2,4-diamine (Example 2f)) are dissolved in 6 ml of tetrahydrofuran and treated with 361 mg of tetrabutylammonium fluoride trihydrate. The mixture is stirred at room temperature for 1hr. and subsequently concentrated. The residue is chromatographed on MCl-Gel CHP20P (Mitsubishi Corporation) with water/acetonitrile 4:1. 73 mg (36%) of 5-(4'-hydroxy-5,6-dimethoxy-biphenyl-3-ylmethyl)-pyrimidine-2,4-diamine are isolated as a colourless solid. M.p. 233°.

5b) In analogy to Example 5a), from 5-(3'-t-butyl-dimethylsilyloxy-5,6-dimethoxy-biphenyl-3-ylmethyl)-pyrimidine-2,4-diamine (Example 2h)) there was obtained 5-(3'-hydroxy-5,6-dimethoxy-biphenyl-3-ylmethyl)-pyrimidine-2,4-diamine as a colourless solid. Yield: 65%. M.p. 215°.

5c) 285 mg of 5-(4'-methoxycarbonyl-5,6-dimethoxy-biphenyl-3-ylmethyl)-pyrimidine-2,4-diamine (Example 2i)) are held at reflux in 15 ml 2N aqueous hydrochloric acid for 6 hrs. After evaporation of the solution there are obtained 248 mg (82%) of 5-(4'-carboxyl-5,6-dimethoxy-biphenyl-3-ylmethyl)-pyrimidine-2,4-diamine hydrochloride as a colourless solid. M.p. 180°.

5d) 100 mg of 5-(3'-methoxycarbonyl-5,6-dimethoxy-biphenyl-3-ylmethyl)-pyrimidine-2,4-diamine (Example 2k)) are dissolved in 3 ml of methanol and treated with 0.25 ml of a 1N sodium hydroxide solution. The mixture is stirred at 50° for 3 hrs., concentrated and the residue is recrystallized in water. 86 mg (89%) of 5-(3'-carboxyl-5,6-dimethoxy-biphenyl-3-ylmethyl)pyrimidine-2,4-diamine are isolated as a colourless solid. M.p. 203° (decomposition).

5e) 322 mg of 5-(3'-(4-nitrobenzene-sulphonylamino)-5,6-dimethoxy-biphenyl-3-ylmethyl)-pyrimidine-2,4-diamine (Example 4f)) are dissolved in 15 ml of glacial acetic acid and treated portionwise with 650 mg of iron powder. The mixture is stirred at room temperature for 2 hrs. Subsequently, it is poured on to ice-water, made alkaline with dilute sodium hydroxide solution and filtered. The residue and the aqueous phase are washed with ethyl acetate; the combined organic phases are dried, evaporated and the residue is chromatographed on silica gel. Eluent: methylene chloride/methanol/conc. ammonia 90:10:1. 230 mg (76%) of 5-(3'-(4-aminobenzene-sulphonylamino)-5,6-dimethoxy-biphenyl- 3-ylmethyl)-pyrimidine-2,4-diamine are isolated as a yellowish solid. M.p. 223°–226°.

5f) 100 mg of 5-(3'-(4-methoxycarbonyl-n-butyrylamino)-5,6-dimethoxy-biphenyl-3-ylmethyl)-pyrimidine-2,4-diamine (Example 4j)) are dissolved in 20 ml of methanol and 2 ml of water and treated with 12 mg of potassium hydroxide. The mixture is stirred at room temperature overnight, then poured on to ice and neutralized with dilute hydrochloric acid. The precipitate is filtered off under suction and washed with water and methylene chloride. 62 mg (64%) of 5-(3'-(4-carboxyl-n-butyrylamino)-5,6-dimethoxy-biphenyl-3-ylmethyl)-pyrimidine-2,4-diamine are isolated as a colourless solid. M.p. 110°.

5g) In analogy to Example 5f)), from 5-(3'-(4-methoxycarbonylbenzoyl)-amino)-5,6-dimethoxy-biphenyl-3-ylmethyl)-pyrimidine-2,4-diamine (Example 4k)) there is obtained S-(3'-(4-carboxyl-benzoyl)-amino)-5,6-dimethoxy-biphenyl-3-ylmethyl)pyrimidine-2,4-diamine as a colourless solid. Yield: 20%. Mass spectrum (FAB): peaks: inter alia at 500 (M++H, 100%), 387 (20%).

5h) In analogy to Example 5a), from 5-(3,4-dimethoxy-5-naphthalen-6-(t-butyl-dimethyl-silyloxy)-2-yl-benzyl)-pyrimidine-2,4-diamine (Example 4l)) there is obtained 5-(3,4-dimethoxy-5-naphthalen-6-hydroxy-2-yl-benzyl)-pyrimidine-2,4-diamine as a colourless solid. Yield: 97%. Mass spectrum: peaks: inter alia at 402 (M+, 100%), 371 (20%), 123 (44%).

5i) 640 mg of 5-(3'-(2-methoxycarbonylethyl-amino)-5,6-dimethoxy-biphenyl-3-ylmethyl)-pyrimidine-2,4-diamine (Example 4n)) are treated with 8 ml of a 1M solution of potassium hydroxide in methanol and stirred at room temperature for 10 hrs. Insoluble material is filtered off from the mixture and the filtrate is concentrated. The residue is chromatographed on MCl-Gel CHP20P (Mitsubishi Corporation) with water/acetonitrile 3:1. 180 mg (26%) of 5-(3'-(2-carboxyethyl-amino)-5,6-dimethoxy-biphenyl-3-ylmethyl)-pyrimidine-2,4-diamine are isolated as a white yellowish solid. M.p. 136°–140° (decomposition).

5j) 200 mg of 5-(4'-carboxyl-5,6-dimethoxy-biphenyl-3-ylmethyl)-pyrimidine-2,4-diamine hydrochloride (Example 5c)) are dissolved in 3 ml of dimethylformamide and treated at 5° with 139 mg of 1,8-diaza-bicyclo[5,4,0]undec-7-ene. 113 mg of pivaloyloxymethyl iodide are added thereto and the mixture is stirred at 0° to 5° for 2 hrs. Subsequently, it is poured into a mixture of 20 ml of ethyl acetate and 20 ml of water. The organic phase is separated and washed with 10 ml of a 50% sodium thiosulphate solution and then with 10 ml of a 50% sodium chloride solution, dried over magnesium sulphate, concentrated and the residue is chromatographed on silica gel with methylene chloride/methanol/conc. ammonia 95:5:0.5. 49 mg (21%) of 5-(4'-pivaloyloxymethylcarbonyl-5,6-dimethoxybiphenyl-3-ylmethyl)-pyrimidine-2,4-diamine are isolated as a colourless solid. Mass spectrum: peaks: inter alia at 494 (M+, 100%), 463 (20%), 363 (46%).

5k) 82 mg of ethyl 7-[5-(2,4-diamino-pyrimidin-5-ylmethyl)-2,3-dimethoxy-phenyl]-1-ethyl-1,4-dihydro-4-oxo-quinoline-3-carboxylate (Example 2t)) are held at reflux in 1 ml of ethanol and 1 ml of 2N aqueous sodium hydroxide solution for one hr. The reaction mixture is cooled to room temperature and acidified with 25% aqueous hydrochloric acid. The precipitated substance is filtered off under suction, washed with water, ethanol and ether and dried. 49 mg (59%) of 7-[5-(2,4-diamino-pyrimidin-5-ylmethyl)-2,3- dimethoxy-phenyl]-1-ethyl-1,4-dihydro-4-oxo-quinoline-3-carboxylic acid hydrochloride are obtained as a colourless solid. M.p.>230° C. Mass spectrum (ISP): peaks: inter alia at 476 (M++H, 100%).

5l) In analogy to Example 5k), from ethyl 7-[5-(2,4-diaminopyrimidin-5-ylmethyl)-2-methoxy-phenyl]-1-ethyl-1,4-dihydro-4-oxo-quinoline-3-carboxylate (Example 2u)) there is obtained 7-[5-(2,4-diamino-pyrimidin-5ylmethyl)-2-methoxy-phenyl]-1-ethyl-1,4-dihydro-4-oxo-quinoline-3-carboxylic acid hydrochloride as a colourless solid. Yield: 71%. M.p.>230°. Mass spectrum (ISP): peaks: inter alia at 446 (M++H, 100%).

5m) in analogy to Example 5k), with ethyl 1-cyclopropyl-7-[4-[5'-(2,4-diamino-pyrimidin-5-ylmethyl)-2',3'-dimethoxybiphenyl-4-ylmethyl]-piperazin-1-yl]-6,8-difluoro-4-oxo-1,4-dihydro-quinoline-3-carboxylate (Example 4p)) there is obtained 1-cyclopropyl-7-[4-[5'-(2,4-diamino-pyrimidin-5-ylmethyl)-2',3'-dimethoxy-biphenyl-4-ylmethyl]-piperazin-1-yl]-6,8-difluoro-4-oxo-1,4-dihydro-quinoline-3-carboxylic acid hydrochloride as a yellowish solid. M.p.>230°. Mass spectrum (ISP): peaks: inter alia at 698.4 ((M++H), 100%).

5n) In analogy to Example 5f), from methyl 3-[5'-(2,4-diaminopyrimidin-5-ylmethyl)-2',3'-dimethoxy-biphenyl-4-yl]-acrylate (Example 4r)) there is obtained the corresponding 3-[5'-(2,4-diamino-pyrimidin-5-ylmethyl)-2',3'-dimethoxy- biphenyl-4-yl]-acrylic acid as a colourless material. Yield: 15%. M.p.>250°.

5o) 182 mg of 5'-(2,4-diamino-pyrimidin-5-ylmethyl)-2',3'-dimethoxy-biphenyl-4-carbaldehyde in 10 ml of methanol are treated at 0° at 19 mg of sodium borohydride. After 1.5 hr. the mixture is concentrated and poured into water. Extraction with methylene chloride and recrystallization from methylene chloride/hexane finally yields 115 mg of [5'-(2,4-diaminopyrimidin-5-ylmethyl)-2',3'-dimethoxy-biphenyl-4-yl]-methanol as a colourless solid. Yield: 63%; m.p.=86°.

5p) In analogy to Example 5f), from methyl 3-[5-[5-(2,4-diaminopyrimidin-5-ylmethyl)-2,3-dimethoxyphenyl]-furan-2-yl-acrylate (Example 4w)) there is obtained the corresponding 3-[5-[5-(2,4-diaminopyrimidin-5-ylmethyl)-2,3-dimethoxyphenyl]-furan-2-yl-acrylic acid as a yellowish solid. Yield: 84%. M.p.=210° (decomposition).

EXAMPLE 6

Preparation of acetals of compounds VI 6a) 90 g of 3-bromo-4,5-dimethoxybenzaldehyde, 42 g of 2,2-dimethyl-propane-1,3-diol and 3.5 g of toluene-4-sulphonic acid in 500 ml of toluene are heated at reflux using a water separator for 0.5 hr. Subsequently, the reaction mixture is cooled and washed with 300 ml of saturated, aqueous sodium bicarbonate solution and then with 300 ml of water. The organic phase is dried over magnesium sulphate and concentrated. The residue is recrystallized in 750 ml of hot n-hexane. 108.6 g (89%) of colourless crystals of 2-(3-bromo-4,5-dimethoxy-phenyl)-5,5-dimethyl-1,3-dioxan are obtained. M.p. 77°–78° C.

6b) In analogy to Example 6a), with 3-bromo-4-methoxybenzaldehyde and 2,2-dimethyl-propane-1,3-diol there is obtained 2-(3-bromo-4-methoxy-phenyl)-5,5-dimethyl-1,3-dioxan. Yield: 55%. M.p. 91°–93°.

6c) In analogy to Example 6a), with 3-bromo-benzaldehyde and ethanol there is obtained 1-bromo-3-diethoxymethyl-benzene. Yield: 97%. B.p. 72°–74°/20 Pa.

EXAMPLE 7

Preparation of acetals of compounds IX

7a) A solution of 1.17 g of 2-(3-bromo-4,5-dimethoxy-phenyl)-5,5-dimethyl-1,3-dioxan (Example 6a)) in 10 ml of tetrahydrofuran is treated dropwise at −100° over 20 minutes with 2.2 ml of a 1.6M n-butyllithium solution in n-hexane. The solution is stirred for a further hour at −100° and then treated dropwise at this temperature with 7 ml of a 0.5M zinc chloride solution in tetrahydrofuran within 20 minutes. The reaction mixture is warmed slowly to 0° and stirred at this temperature for a further 1hr. The solution is then slowly added dropwise through a Teflon tube to a boiling mixture of 1 g of ethyl 1-cyclopropyl-6-fluoro- 1,4-dihydro-4-oxo-7-[[(trifluoromethyl)sulphonyl]oxy]quinoline-3-carboxylate (J. Heterocyclic Chem., 28, 1581 (1991)) and 20 mg of tetrakis-triphenylphosphine-palladium in 10 ml of tetrahydrofuran. The mixture is stirred at reflux temperature for a further 2 hrs. it is cooled to room temperature, diluted with 50 ml of ethyl acetate and washed with 50 ml of a saturated aqueous ammonium chloride solution, 50 ml of water and 50 ml of a saturated aqueous sodium chloride solution. The organic phase is dried over magnesium sulphate and concentrated. The residue is chromatographed on silica gel with ethyl acetate. 850 mg (68%) of ethyl 1-cyclopropyl-7-[5-(5,5-dimethyl-1,3-dioxan-2-yl)-2,3-dimethoxy-phenyl]-6-fluoro-1,4-dihydro-4-oxo-quinoline-3-carboxylate are isolated as a colourless solid. M.p. 178°–180° after recrystallization from ethyl acetate/n-hexane.

7b) In analogy to Example 7a), from 2-(3-bromo-4-methoxyphenyl)-5,5-dimethyl-1,3-dioxan (Example 6b)) and ethyl 1-cyclopropyl-6-fluoro-1,4-dihydro-4-oxo-7[[(trifluoromethyl)sulphonyloxy]-3-quinoline-carboxylate (J. Heterocyclic Chem., 28, 1581 (1991)) there is obtained ethyl 1-cyclopropyl-7-[5-(5,5-dimethyl-1,3-dioxan-2-yl)-2-methoxy-phenyl]-6-fluoro-1,4-dihydro-4-oxo-quinoline-3-carboxylate as a colourless solid. Yield: 40%. M.p. 220° (decomposition) after recrystallization from ethyl acetate/n-hexane.

7c) In analogy to Example 7a), from 1-bromo-3-diethoxymethyl-benzene (Example 6c)) and ethyl 1-cyclopropyl-6-fluoro-1,4-dihydro-4-oxo-7-[[(trifluoromethyl)sulphonyl]oxy]-quinoline-3-carboxylate there is obtained ethyl 1-cyclopropyl-7-(3-diethoxymethyl-phenyl]-6-fluoro-1,4-dihydro-4-oxo-quinoline-3-carboxylate as a colourless solid. Yield: 44%. Mass spectrum: peaks: inter alia at 453 (M+, 16%), 408 (21%), 381 (100%).

EXAMPLE 8

Biaryl compounds IX 8a) 575 mg of ethyl 1-cyclopropyl-7-[5-(5,5-dimethyl-1,3-dioxan-2-yl)-2,3-dimethoxy-phenyl]-6-fluoro-1,4-dihydro-4-oxo-quinoline-3-carboxylate (Example 7a)) are heated to boiling under reflux in a mixture of 8 ml of a 2N aqueous hydrochloric acid solution and 5 ml of ethanol for 6 hrs. The reaction mixture is cooled in an ice bath and the separated precipitate is filtered off under suction and washed with 20 ml of water and with 50 ml of ether. 330 mg (73%) of 1-cyclopropyl-6-fluoro-7-(5-formyl-2,3-dimethoxy-phenyl)-1,4-dihydro-4-oxo-quinoline-3-carboxylic acid are obtained as a colourless solid. M.p.>230°. Mass spectrum: peaks: inter alia at 411 (M+, 6%), 367 (100%), 338 (6%), 202 (8%), 184 (10%).

8b) In analogy to Example 8a), from ethyl 1-cyclopropyl-7-[5-(5,5-dimethyl-1,3-dioxan-2-yl)-2-methoxy-phenyl]-6-fluoro-4-oxo-1,4-dihydro-quinoline-3-carboxylate there is obtained 1-cyclopropyl-6-fluoro-7-(5-formyl-2-methoxy-phenyl)-1,4-dihydro-4-oxo-quinoline-3-carboxylic acid as a colourless solid. Yield: 61%. M.p.>230°. Mass spectrum: peaks: inter alia at 380 (M+, 100%), 336 (52%).

8c) In analogy to Example 8a), from ethyl 1-cyclopropyl-7-(3-diethoxymethyl-phenyl]-6-fluoro-1,4-dihydro-4-oxo-quinoline-3-carboxylate there is obtained 1-cyclopropyl-6-fluoro-7-(3-formyl-phenyl)-1,4-dihydro-4-oxo-quinoline-3-carboxylic acid as a colourless solid. Yield: 86%. M.p.>230°. Mass spectrum: peaks: inter alia at 351 (M+, 4%), 307 (100%), 278 (11%), 202 (9%).

EXAMPLE 9

Preparation of compounds of formula I

9a) A suspension of 310 mg of 1-cyclopropyl-6-fluoro-7-(5-formyl-2,3-dimethoxy-phenyl)-1,4-dihydro-4-oxo-quinoline-3-carboxylic acid (Example 8a)) in 3 ml of dimethyl sulphoxide is treated with 110 mg of 3-anilinopropionitrile and 185 mg of potassium tert-butylate. The resulting solution is stirred at room temperature for one hr. The reaction mixture is poured into 30 ml of water, adjusted to pH 5 with 2N aqueous HCl and extracted twice with 50 ml of methylene chloride each time. The combined organic phases are washed with 50 ml of water and with 50 ml of saturated, aqueous sodium chloride solution, dried over magnesium sulphate and concentrated. 400 mg (98%) of 7-[5-(2-cyano-3-phenylamino-allyl)-2,3-dimethoxy-phenyl]-1-cyclopropyl-6-fluoro-1,4-dihydro-4-oxo-quinoline-3-carboxylic acid are obtained as a yellow foam.

A solution of 215 mg of guanidine hydrochloride in 5 ml of ethanol is treated with 337 mg of potassium tert-butylate in 5 ml of ethanol. After half an hour the resulting suspension is added to 400 mg of 7-[5-(2-cyano-3-phenylamino-allyl)-2,3-dimethoxy-phenyl)]-1-cyclopropyl-6-fluoro-1,4-dihydro-4-oxo-quinoline-3-carboxylic acid and the suspension is held at reflux for 6 hrs. The reaction mixture is cooled to room temperature and poured into 30 ml of water, adjusted to pH 5 with 2N aqueous hydrochloric acid and stirred for 1 hr. The precipitate is filtered off under suction, washed with 20 ml of water, 20 ml of ethanol and 20 ml of ether and dried. 178 mg (44%) of 1-cyclopropyl-7-[5-(2,4-diamino-pyrimidin-5-ylmethyl)-2,3-dimethoxyphenyl]-6-fluoro-1,4-dihydro-4-oxo-quinoline-3-carboxylic acid are isolated as beige crystals. This substance is suspended in 5 ml of methylene chloride and treated with 0.3 ml of trifluoroacetic acid, whereby a solution results. The latter is treated with 1 ml of ether and stirred for a further 30 min. The crystallized-out substance is filtered off under suction and washed with 20 ml of ether. 129 mg (63%) of 1-cyclopropyl-7-[5-(2,4-diaminopyrimidin- 5-ylmethyl)-2,3-dimethoxy-phenyl]-6-fluoro-1,4-dihydro-4-oxo-quinoline-3-carboxylic acid trifluoroacetate are obtained as beige crystals. M.p.>230°. Mass spectrum: peaks: inter alia at 505 (M+, 1.5%), 461 (3.3%), 45 (100).

9b) In analogy to Example 9a), from 1-cyclopropyl-6-fluoro-7-(5-formyl-2-methoxy-phenyl)-1,4-dihydro-4-oxo-quinoline-3-carboxylic acid (Example 8b)) there is obtained 1-cyclopropyl-7-[5-(2,4-diamino-pyrimidin-5-ylmethyl)-2-methoxy-phenyl]-6-fluoro-1,4-dihydro-4-oxo-quinoline-3-carboxylic acid trifluoroacetate as beige crystals. Yield: 29%. M.p.>230°. Mass spectrum (ISP): peaks: inter alia at 476 (M++H, 100%).

9c) In analogy to Example 9a), from 1-cyclopropyl-6-fluoro-7-(3-formyl-phenyl)-1,4-dihydro-4-oxo-quinoline-3-carboxylic acid (Example 8c)) there is obtained 1-cyclopropyl-7-[5-(2,4-diamino-pyrimidin-5-ylmethyl)-phenyl]-6-fluoro-1,4-dihydro-4-oxo-quinoline-3-carboxylic acid as a beige solid. Yield: 23%. M.p.>230°. Mass spectrum (ISP): peaks: inter alia at 446 (M++H, 100%).

EXAMPLE 10

Preparation of vinyl compounds of formula I via the Heck reaction

10a) A mixture of 500 mg of 5-(3,4-dimethoxy-5-iodo-benzyl)pyrimidine-2,4-diamine, 1.53 g of styrene, 1.46 g of triethylamine and 31 mg of palladium-(II) acetate in 25 ml of dioxan is held at reflux under argon for 14 hrs. The mixture is poured on to ice-water, adjusted to pH 5 to 7 with 3N aqueous hydrochloric acid and extracted with methylene chloride. The organic phase is dried over magnesium sulphate, concentrated and the residue is chromatographed on silica gel with methylene chloride/methanol 97:3. 252 mg (53%) of 5-(3,4-dimethoxy-5-styryl-benzyl)pyrimidine-2,4-diamine are isolated as an orange solid. M.p.226°.

10b) In analogy to Example 1a), with 2-vinyl-naphthalene there is obtained 5-[3,4-dimethoxy-5-(2-naphthalen-2-yl-vinyl)-benzyl]-pyrimidine- 2,4-diamine as a yellowish solid. Yield: 15%. M.p. 203°.

10c) In analogy to Example 1a), from 3,4-dimethoxy-styrene there is obtained 5-[3,4-dimethoxy-5-(3',4'-dimethoxy-styryl)benzyl]-pyrimidine-2,4-diamine as a yellowish solid. Yield: 64%. M.p. 256°.

10d) In analogy to Example 1a), from 4-vinyl-biphenyl there is obtained 5-[3-(2-biphenyl-4-yl-vinyl)-4,5-dimethoxy-benzyl]-pyrimidine-2,4-diamine as a colourless solid. Yield: 43%. M.p. 155°.

10e) In analogy to Example 1a), from 4-vinyl-N,N-dimethylaniline (Yoshida et al, Bull. Chem. Soc. Japan 63, 1751) there is obtained 5-[3,4-dimethoxy-5-(4'-dimethylamino-styryl)-benzyl]-pyrimidine-2,4-diamine as a yellowish solid. Yield: 13%. Mass spectrum: peaks: inter alia at 405 (M+, 100%), 390 (36%), 134 (44%), 123 (64%).

10f) In analogy to Example 1a), from 1-vinyl-naphthalene there is obtained 5-[3,4-dimethoxy-5-(1-naphthalen-2-yl-vinyl)benzyl]-pyrimidine-2,4-diamine as a yellowish solid. Yield: 5%. Mass spectrum: peaks: inter alia at 412 (M+, 50%), 397 (22%), 381 (14%), 123(100%).

10g) In analogy to Example 1a), from N-(p-vinylbenzyl)-N,N-dimethylamine there is obtained 5-[3-[2-(4-dimethylaminomethyl-phenyl)-vinyl]-4,5-dimethoxy-benzyl]-pyrimidine-2,4-diamine as a yellowish solid. Yield: 26%. Mass spectrum (FAB): peaks: inter alia at 420 (M++H, 100%).

10h) In analogy to Example 1a), from 4-hydroxy-styrene there is obtained 5-[3,4-dimethoxy-5-(4'-hydroxystyryl)-benzyl]-pyrimidine-2,4-diamine as a yellowish solid. Yield: 10%. Mass spectrum: peaks: inter alia at 379 (M++H, 100%).

10i) 1.93 g of 5-(3,4-dimethoxy-5-iodo-benzyl)-pyrimidine-2,4-diamine, 55 mg of palladium-(II) acetate, 10 ml of t-butyl acrylate and 25 ml of tri-n-butylamine is held at reflux under argon for 5 hrs. The mixture is poured on to ice-water, extracted with methylene chloride, dried and concentrated. After chromatography on silica gel with methylene chloride/methanol/conc. ammonia 82 mg (4%) of t-butyl 3-[5-(2,4-diamino-pyrimidin-5-ylmethyl)-2,3-dimethoxy-phenyl]-acrylate are obtained as a colourless solid. M.p. 101°.

EXAMPLE 11

Preparation of ethynyl compounds of formula I

11a) A mixture of 8.7 g of 5-(3,4-dimethoxy-5-iodobenzyl)-pyrimidine-2,4-diamine, 6.2 ml of ethynyltrimethylsilane, 80 mg of bis-trimethylphosphinepalladium dichloride and 1 mg of copper(I) iodide in 25 ml of triethylamine and 25 ml of dimethylformamide is stirred at 60° for 16 hrs. After cooling to room temperature the reaction mixture is treated with 400 ml of water and extracted three times with 200 ml of methylene chloride each time. The combined organic phases are washed twice with 250 ml of water, once with 250 ml of a saturated sodium chloride solution and dried over magnesium sulphate. The crude product is chromatographed on silica gel with methylene chloride/methanol 9:1. 4.73 g (59%) of 5-[3-trimethylsilyl-ethynyl-4,5-dimethoxy-benzyl]-pyrimidine-2,4-diamine are obtained as beige crystals. M.p. 189°–190°.

11b) A suspension of 4.65 g of 5-[3-trimethylsilyl-ethynyl-4,5-dimethoxy-benzyl]-pyrimidine-2,4-diamine and 2.7 g of potassium fluoride dihydrate in 20 ml of dimethylformamide is stirred at room temperature for 1 hr. The suspension is poured into 200 ml of water and extracted three times with 150 ml of methylene chloride each time. The combined organic phases are washed with 150 ml of saturated sodium chloride solution and dried over magnesium sulphate. The crude product is triturated with 25 ml of methylene chloride, filtered off under suction and dried. 2.41 g (65%) of 5-[3-ethynyl-4,5-dimethoxy-benzyl]-pyrimidine-2,4-diamine are obtained. M.p. 173°–175°.

11c) In analogy to Example 11a), with 1-(4-ethynyl-phenyl)ethanone there is obtained 1-{4-[5-(2,4-diamino-pyrimidin-5-ylmethyl)-2,3-dimethoxy-phenylethynyl]-phenyl}-ethanone. Yield: 30%. M.p. 234° C.

EXAMPLE 12

Preparation of ethynyl compounds of formula I

12a) A solution of 200 mg of 5-[3-ethynyl-4,5-dimethoxy-benzyl]-pyrimidine-2,4-diamine (Example 11b)), 207 mg of ethyl 1-cyclopropyl-6,8-difluoro-4-oxo-1,4-dihydro-7-[[(trifluoromethyl)sulphonyl]oxy]-quinoline-3-carboxylate (J. Heterocyclic Chem., 28, 1581 (1991)) and 10 mg of bis-triphenylphosphinepalladium dichloride in 1.5 ml of triethylamine and 7.5 ml of dimethylformamide is stirred at 900 for one hr. The reaction mixture is cooled to room temperature, poured into 50 ml of water and extracted four times with 50 ml of methylene chloride each time. The combined organic phases are washed with 100 ml of saturated, aqueous sodium chloride solution, dried over magnesium sulphate and concentrated. The residue is chromatographed on silica gel with methylene chloride/methanol 9:1. 108 mg (39%) of ethyl 1-cyclopropyl-7-[5-(2,4-diamino-pyrimidin-5-ylmethyl)-2,3-dimethoxy-phenylethynyl]-6,8-difluoro-4-oxo-1,4-dihydro-quinoline-3-carboxylate are isolated as a colourless solid. M.p.>230°. Mass spectrum: peaks: inter alia at 575 (M+, 36%), 503 (18%), 481 (20%), 123 (42%), 32(100%).

12b) In analogy to Example 3a), with ethyl 1-cyclopropyl-6-fluoro-4-oxo-1,4-dihydro-7-[[(trifluoromethyl)sulphonyl]oxy]-quinoline-3-carboxylate (J. Heterocyclic Chem., 28, 1581 (1991)) there is obtained ethyl 1-cyclopropyl-7-[5-(2,4-diamino-pyrimidin-5-ylmethyl)-2,3-dimethoxy-phenylethynyl]-6-fluoro-4-oxo-1,4-dihydro-quinoline-3-carboxylate as a colourless solid. Yield: 48%. M.p.>230°. Mass spectrum (ISP): peaks: inter alia at 558.5 (M++H, 100%).

12c) In analogy to Example 3a), with ethyl 1-ethyl-6-fluoro-4-oxo-1,4-dihydro-7-[[(trifluoromethyl)sulphonyl]oxy]-quinoline-3-carboxylate (Example 13b)) there is obtained ethyl 1-ethyl-7-[5-(2,4-diamino-pyrimidin-5-ylmethyl)-2,3-dimethoxy-phenylethynyl]-6-fluoro-4-oxo-1,4-dihydro-quinoline-3-carboxylate as a colourless solid. Yield: 68%. M.p.>230°. Mass spectrum (ISP): peaks: inter alia at 546.5 (M++H, 100%).

12d) In analogy to Example 3a), with methyl 6-iodo-pyridine-3-carboxylate (Example 13d)) there is obtained methyl 6-[5-(2,4-diamino-pyrimidin-5-ylmethyl)-2,3-dimethoxy-phenylethynyl]nicotinate as a yellowish solid. Yield: 58%. M.p. 157° (dec.).

12e) In analogy to Example 3a), with ethyl 6-(trifluoro-methanesulphonyloxy)-naphthalene-2-carboxylate (Example 13c)) there is obtained ethyl 6-[5-(2,4-diamino-pyrimidin-5-ylmethy))-2,3-dimethoxy-phenylethynyl]-naphthalene-2-carboxylate as a yellowish solid. Yield: 12%. M.p. 220°–222°.

12f) In analogy to Example 3a), with methyl 4-iodo-salicylate (Canadian J. of Chemistry, 48, 945, 1970) there is obtained methyl 4-[5-(2,4-diamino-pyrimidin-5-ylmethyl)-2,3-dimethoxy-phenylethynyl]-2-hydroxy-benzoate as a colourless solid. Yield: 37%. M.p. 183°°185°.

12g) In analogy to Example 3a), with ethyl 7-bromo-1-ethyl-4-oxo-1,4-dihydro-quinoline-3-carboxylate (U.S. Pat. No. 4,959,363, C.A. 114:81620z) there is obtained ethyl 1-ethyl-7-[5-(2,4-diamino-pyrimidin-5-ylmethyl)-2,3-dimethoxy-phenylethynyl]-4-oxo-1,4-dihydro-quinoline-3-carboxylate as a colourless solid. Yield: 27%. M.p. 129° (dec.).

12h) 3 g of ethyl 7-bromo-1-cyclohexyl-4-oxo-1,4-dihydro-quinoline-3-carboxylic acid (Example 13ad)) are dissolved in 35 ml of N,N-dimethylformamide to 90° C. under argon with 200 mg of bis(triphenylphosphine)palladium(II) dichloride and treated dropwise within one hour with a solution of 5-[3-ethynyl-4,5-dimethoxy-benzyl]-pyrimidine-2,4-diamine (Example 11b)) in 35 ml of N,N-dimethylformamide and 35 ml of triethylamine. The dark red solution is stirred at 90° C. for a further 1 hr. The reaction mixture is left to cool to room temperature and is poured into 150 ml of 10% aqueous sodium carbonate solution while stirring. After 15 min. the suspension is suction filtered and the residue is washed with 100 ml of water and then with 100 ml of diethyl ether and dried at room temperature in a high vacuum. The crude product is triturated with 50 ml of diethyl ether for one hour, filtered off under suction and dried in a high vacuum at room temperature. 3.83 g (83%) of ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate are obtained as a light yellow solid. M.p. 228°–230° C.

12i) In analogy to Example 12h), with ethyl 7-iodo-4-oxo-1-propyl-1,4-dihydro-quinoline-3-carboxylate (Example 13i)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-4-oxo-1-propyl-1,4-dihydro-quinoline-3-carboxylate as a beige solid. Yield: 54%. M.p.>139° C. (dec.). mass spectrum (ISP): 542 (M++H).

12j) In analogy to Example 12h), with ethyl 1-cyclopropylmethyl-7-iodo-4-oxo-1,4-dihydro-quinoline-3-carboxylate (Example 13j)) and 5-[3-ethynyl-4,5-dimethoxy-benzyl]-pyrimidine-2,4-diamine (Example 11b)) there is obtained ethyl 1-cyclopropylmethyl-7-[5-(2,4-diamino-pyrimidin-5-ylmethyl)-2,3-dimethoxy-phenylethynyl]-4-oxo-1-propyl-1,4-dihydro-quinoline-3-carboxylate as a beige solid. Yield: 46%. M.p. 117°–119° C.

12k) In analogy to Example 12h), with ethyl 1-(2-hydroxy-ethyl)-7-iodo-4-oxo-1,4-dihydro-quinoline-3- carboxylate (Example 13k)) and 5-[3-ethynyl-4,5-dimethoxy-benzyl]-pyrimidine-2,4-diamine (Example 11b)) there is obtained ethyl 1-7-[5-(2,4-diamino-pyrimidin-5-ylmethyl)-2,3-dimethoxy-phenylethynyl]-1-(2-hydroxy-ethyl)-4-oxo-1,4-dihydro-quinoline-3-carboxylate as a beige solid. Yield: 24%. Mass spectrum (FAB): Peaks inter alia at 544 (M++H, 100%), 502 (6%), 250 (16%).

12l) In analogy to Example 12h), with ethyl 1-{2-[2-(2-hydroxy-ethoxy)-ethoxy]-ethyl}-7-iodo-4-oxo-1,4-dihydro-quinoline-3-carboxylate (Example 13l)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxyphenylethynyl]-1-{2-[2-(2-hydroxy-ethoxy)-ethoxy]-ethyl}-4-oxo-1,4-dihydro-quinoline-3-carboxylate as a colourless amorphous solid. Yield: 64%. Mass spectrum (ISP): 632.5 (M++H, 100%).

12m) In analogy to Example 12h), with ethyl 7-iodo-4-oxo-1-(pyridin-4-yl)methyl-1,4-dihydro-quinoline-3-carboxylate (Example 13n)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-4-oxo-1-pyridin-4-ylmethyl-1,4-dihydro-quinoline-3-carboxylate as a yellowish solid. Yield: 87%. M.p.>141° C. (dec.). Mass spectrum (ISP): 12n) In analogy to 100%).

12n) In analogy to Example 12h), with ethyl 7-chloro-1-ethyl-4-oxo-1,4-dihydro-[1,8]naphthyridin-3-carboxylate (Chem. Pharm. Bull. 1982,30, 2399–2409) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-1-ethyl-4-oxo-14-dihydro-[ 1,8]naphthyridin-3-carboxylate as a light yellowish solid. Yield: 64%. M.p.>216° C.

Mass spectrum (ISP): 529.4 (M++H, 100%).

12o) In analogy to Example 12h), with ethyl 1-cyclopentyl-7-iodo-4-oxo-1,4-dihydro-quinoline-3-carboxylate (Example 13o)) and 5-[3-ethynyl-4,5-dimethoxy-benzyl]-pyrimidine-2,4-diamine (Example 11b)) there is obtained ethyl 1-cyclopentyl-7-[5-(2,4-diamino-pyrimidin-5-ylmethyl)-2,3-dimethoxy-phenylethynyl]-4-oxo-1,4-dihydro-quinoline-3-carboxylate as a yellowish solid. Yield: 36%. M.p.>113° C. (dec.). Mass spectrum (ISP): 568.4 (M++H, 100%).

12p) In analogy to Example 12h), with ethyl 1-adamantan-1-yl-7-iodo-4-oxo-1,4-dihydro-quinoline-3-carboxylate (Example 13p)) and 5-[3-ethynyl-4,5-dimethoxy-benzyl]-pyrimidine-2,4-diamine (Example 11b)) there is obtained ethyl 1-adamantan-1-yl-7-[5-(2,4-diamino-pyrimidin-5-ylmethyl)-2,3-dimethoxy-phenylethynyl]-4-oxo-1,4-dihydro-quinoline-3-carboxylate as a yellowish solid. Yield: 64%. M.p.>185° C. (dec.). Mass spectrum (FAB): peaks inter alia at 634 (M++H, 100%), 618 (3%), 582 (5%), 560(6%).

12q) In analogy to Example 12h), with ethyl ( )-1-exo-bicyclo [2.2.1]hept-2-yl-7-iodo-4-oxo-1,4-dihydro-quinoline-3-carboxylate (Example 13q)) and 5-[3-ethynyl-4,5-dimethoxy-benzyl]-pyrimidine-2,4-diamine (Example 11b)) there is obtained ethyl ( )-1-bicyclo[2.2.1]hept-2-yl-7-[5-(2,4-diamino-pyrimidin-5-ylmethyl)-2,3-dimethoxy-phenylethynyl]-4-oxo-1,4-dihydro-quinoline-3-carboxylate as a yellowish solid. Yield: 98%. M.p.>168° C. (dec.). Mass spectrum (FAB): peaks inter alia at 594 (M++H, 100%), 561 (2%), 500 (3%), 387 (9%).

12r) In analogy to Example 12h), with ethyl 7-iodo-4-oxo-1-(1,1,3,3-tetramethyl-butyl)-1,4-dihydro-quinoline-3-carboxylate and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-4-oxo-(1,1,3,3-tetramethyl-butyl)-1,4-dihydro-quinoline-3-carboxylate as a yellowish amorphous solid. Yield: 71%. Mass spectrum (ISP): peaks inter alia at 612.6 (M++H, 100%), 500.4 (96%), 454.3 (19%).

12s) In analogy to Example 12h), with ethyl 1-tert-butyl-7-iodo-4-oxo-1,4-dihydro-quinoline-3-carboxylate (Example 13s)) and 5-[3-ethynyl-4,5-dimethoxy-benzyl]-pyrimidine-2,4-diamine (Example 11b)) there is obtained ethyl 1-tert-butyl-7-[5-(2,4-diamino-pyrimidin-5-ylmethyl)-2,3-dimethoxy-phenylethynyl]-4-oxo-1,4-dihydro-quinoline-3-carboxylate as a yellowish solid. Yield: 45%. M.p.>205° C. (dec.). Mass spectrum (FAB): peaks inter alia at 556 (M++H, 100%), 509 (2%), 487 (3%).

12t) In analogy to Example 12h), with ethyl 1-(trans-4-tert-butoxycarbonylamino-cyclohexyl)-7-iodo-4-oxo-1,4-dihydro-quinoline-3-carboxylate (Example 13t)) and 5-[3-ethynyl-4,5-dimethoxy-benzyl]-pyrimidine-2,4-diamine (Example 11b)) there is obtained ethyl 1-(trans-4-tert-butoxycarbonylamino-cyclohexyl)-7-[5-(2,4-diamino-pyrimidin-5-ylmethyl)-2,3-dimethoxy-phenylethynyl]-4-oxo-1,4-dihydro-quinoline-3-carboxylate as a yellowish amorphous solid. Yield: 86%. Mass spectrum (ISP): peaks inter alia at 697.5 (M++H, 63%), 500.4 9%), 454.3 (26%), 321.5 (100%).

12u) In analogy to Example 12h), with ethyl 7-iodo-4-oxo-1-piperidin-4-ylmethyl-1,4-dihydro-quinoline-3-carboxylate (Example 13u)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-4-oxo-1-piperidin-4-ylmethyl-1,4-dihydro-quinoline-3-carboxylate as a yellowish solid. Yield: 48%. M.p.>205° C. (dec.). Mass spectrum (FAB): peaks inter alia at 597 (M++H, 47%), 500 (72%), 454 (31%), 299 (100%).

12v) In analogy to Example 12h), with 1-cyclopropyl-7-iodo-4-oxo-1,4-dihydro-quinoline-3-carboxylate (Example 13v)) and 5-[3-ethynyl-4,5-dimethoxy-benzyl]-pyrimidine-2,4-diamine (Example 11b)) there is obtained ethyl 1-cyclopropyl-7-[5-(2,4-diamino-pyrimidin-5-ylmethyl)-2,3-dimethoxy-phenylethynyl]-4-oxo-1,4-dihydro-quinoline-3-carboxylate as a yellowish solid. Yield: 39%. M.p.>230° C. (dec.). Mass spectrum (FAB): peaks inter alia at 540 (M++H, 100%), 494(2%), 247(7%).

12w) In analogy to Example 12h), with ethyl 7-iodo-4-oxo-1-(2,2,2-trifluoro-ethyl)-1,4-dihydro-quinoline-3-carboxylate (Example 13w)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]- 4-oxo-1-(2,2,2-trifluoro-ethyl)-1,4-dihydro-quinoline-3-carboxylate as a yellowish solid. Yield: 44%. M.p.>151° C. (dec.). Mass spectrum (ISP): 582.3 (M++H, 100%).

12x) In analogy to Example 12h), with ethyl 7-iodo-4-oxo-1-phenyl-1,4-dihydro-quinoline-3-carboxylate (Example 13x)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-4-oxo-1-phenyl-1,4-dihydro-quinoline-3-carboxylate as a yellowish amorphous solid. Yield: 80%. Mass spectrum (ISP): 576.4 (M++H, 100%).

12y) In analogy to Example 12h), with 2-chloro-4-iodo-1-acetophenone (Example 13ai)) and 5-[3-ethynyl-4,5-dimethoxy-benzyl]-pyrimidine-2,4-diamine (Example 11b))

there is obtained 2-chloro-4-[5-(2,4-diamino-pyrimidin-5-ylmethyl)-2,3-dimethoxy-phenylethynyl]-acetophenone as a yellowish amorphous solid. Yield: 20%. Mass spectrum (ISP): 437.4 (M++H, 100%).

12z) In analogy to Example 12h), with 1-ethyl-7-iodo-4-oxo-1,4-dihydro-quinoline-3-carboxylic acid (3-dimethylamino-propyl)-amide (Example 13z)) and 5-[3-ethynyl-4,5-dimethoxy-benzyl]-pyrimidine-2,4-diamine (Example 11b)) there is obtained 1-ethyl-7-[5-(2,4-diamino-pyrimidin-5-ylmethyl)-2,3-dimethoxy-phenylethynyl]-4-oxo-1,4-dihydro-quinoline-3-carboxylic acid (3-dimethylamino-propyl)-amide as a beige solid. Yield: 79%. M.p.>120° C. (dec.). Mass spectrum (ISP): 584.3 (M++H).

12aa) In analogy to Example 12h), with 1-ethyl-7-iodo-4-oxo-1,4-dihydro-quinoline-3-carboxylic acid (2-hydroxy-ethyl)-amide (Example 13aa) and 5-[3-ethynyl-4,5-dimethoxy-benzyl]-pyrimidine-2,4-diamine (Example 11b)) there is obtained 1-ethyl-7-[5-(2,4-diamino-pyrimidin-5-ylmethyl)-2,3-dimethoxy-phenylethynyl]-4-oxo-1,4-dihydro-quinoline-3-carboxylic acid (2-hydroxy-ethyl)-amide as a beige solid. Yield: 79%. M.p.>230° C. (dec.). Mass spectrum (ISP): 543.4 (M++H).

12ab) In analogy to Example 12h), with 2-dimethylamino-ethyl 1-ethyl-7-iodo-4-oxo-1,4-dihydro-quinoline-3-carboxylate (Example 13ab)) and 5-[3-ethynyl-4,5-dimethoxy-benzyl]-pyrimidine-2,4-diamine (Example 11b)) there is obtained 2-dimethylamino-ethyl 1-ethyl-7-[5-(2,4-diamino-pyrimidin-5-ylmethyl)-2,3-dimethoxy-phenylethynyl]-4-oxo-1,4-dihydro-quinoline-3-carboxylate as a beige solid. Yield: 82%. M.p.>95° C. (dec.). Mass spectrum (FAB): peaks inter alia at 571 (M++H, 8%), 500 (100%), 482 (43%).

12ac) In analogy to Example 12h), with 2-diisopropylamino-ethyl 7-bromo-1-cyclohexyl-4-oxo-1,4-dihydro-quinoline-3-carboxylate (Example 13af)) and 5-[3-ethynyl-4,5-dimethoxy-benzyl]-pyrimidine-2,4-diamine (Example 11b)) there is obtained 2-diisopropylamino-ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate as a beige solid. Yield: 26%. M.p.>175° C. (dec.). Mass spectrum (FAB): peaks inter alia at 681 (M++H, 7%), 554 (58%), 341 (100%).

12ad) In analogy to Example 12h), with 2-morpholin-4-yl-ethyl 7-bromo-1-cyclohexyl-4-oxo-1,4-dihydro-quinoline-3-carboxylate (Example 13ag)) and 5-[3-ethynyl-4,5-dimethoxy-benzyl]-pyrimidine-2,4-diamine (Example 11b)) there is obtained 2-morpholin-4-yl-ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate as a beige solid. Yield: 34%. M.p. 148°–150° C.

12ae) In analogy to Example 12h), with ethyl 7-bromo-1-cyclohexyl-8-methoxy-4-oxo-1,4-dihydro-quinoline-3-carboxylate (Example 13ah)) and 5-[³-ethynyl-4,5-dimethoxy-benzyl]-pyrimidine-2,4-diamine (Example 11b)) there is obtained ethyl 1-cyclohexyl-7-[5-(2,4-diamino-pyrimidin-5-ylmethyl)-2,3-dimethoxy-phenylethynyl]-8-methoxy-4-oxo-1,4-dihydro-quinoline-3-carboxylate as a yellowish amorphous solid. Yield: 52%. Mass spectrum (FAB): peaks inter alia at 612 (M++H, 100%), 582 (3%), 557 (2%).

12af) In analogy to Example 12h), with 1-ethyl-7-iodo-4-oxo-1,4-dihydro-quinoline-3-carboxamide (J. Med. Chem. 1993, 36, 1580–1596)) and 5-[3-ethynyl-4,5-dimethoxy-benzyl]-pyrimidine-2,4-diamine (Example 11b)) there is obtained 1-ethyl-7-[5-(2,4-diamino-pyrimidin-5-ylmethyl)-2,3-dimethoxy-phenylethynyl]-4-oxo-1,4-dihydro-quinoline-3-carboxamide as a yellowish solid. Yield: 19%. M.p.>230° C. (dec.). Mass spectrum: peaks inter alia at 498 (M+, 100%), 480 (18%), 466 (21%), 453 (51%).

12ag) In analogy to Example 12h), with 4-amino-N-(6-bromo-2-methoxy-pyridin-3-yl)-benzenesulphonamide (Helv. Chim. Acta, 1964, 47, 363–379) and 5-[3-ethynyl-4,5-dimethoxy-benzyl]-pyrimidine-2,4-diamine (Example 11b)) there is obtained 4-amino-N-{6-[5-(2,4-diamino-pyrimidin-5-ylmethyl)-2,3-dimethoxy-phenylethynyl]-2-methoxy-pyridin-3-yl}-benzenesulphonamide as a yellowish solid. Yield: 82%. M.p. 125°–127° C.

12ah) In analogy to Example 12h), with methyl 5-iodo-salicylate and 5-[3-ethynyl-4,5-dimethoxy-benzyl]-pyrimidine-2,4-diamine (Example 11b)) there is obtained methyl 5-[5-(2,4-diamino-pyrimidin-5-ylmethyl)-2,3-dimethoxy-phenylethynyl]-2-hydroxy-benzoate as a beige solid. Yield: 24%. M.p.>168° C. (dec.). Mass spectrum (ISP): 435.4 (M++H, 100%).

12ai) In analogy to Example 12h), with ethyl 1-cyclohexyl-6,8-difluoro-4-oxo-7-trifluoromethyl)sulphonyloxy-1,4-dihydro-quinolinecarboxylate (Example 13am)) and 5-[3-ethynyl-4,5-dimethoxy-benzyl]-pyrimidine-2,4-diamine (Example 11b)) there is obtained ethyl 1-cyclohexyl-7-[5-(2,4-diamino-pyrimidin-5-ylmethyl)-2,3-dimethoxy-phenylethynyl]-6,8-difluoro-4-oxo-1,4-dihydro-quinoline-3-carboxylate as a yellowish solid. M.p. 182°–185° C.

12aj) In analogy to Example 12h), with ethyl 6,8-difluoro-4-oxo-1-phenyl-7-trifluoromethyl)sulphonyloxy-1,4-dihydro-quinoline-carboxylate (Example 13an)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-6,8-difluoro-4-oxo-1-phenyl-1,4-dihydro-quinoline-3-carboxylate as a beige solid. M.p.>230° C. Mass spectrum (ISP): 612.3 (M++H, 100%).

12ak) In analogy to Example 12h), with N-(4-bromo-benzoyl)methanesulphonamide (Vopr. Khim. Khim. Tekhnol. 1974, 32, 26–28, CA 81:120162) and 5-[3-ethynyl-4,5-dimethoxy-benzyl]-pyrimidine-2,4-diamine (Example 11b)) there is obtained N-{4-[5-(2,4-diamino-pyrimidin-5-ylmethyl)-2,3-dimethoxy-phenylethynyl]-benzoyl}-methanesulphonamide as a beige solid. Yield: 20%. M.p.>230° C. Mass spectrum (ISP): 482.0 (M++H, 100%).

12al) In analogy to Example 12h), with 6-iodo-1,7-dimethoxy-naphthalene (C.Mellin et al., Tetrahed. 43, 5443 (1987)) and 5-[3-ethynyl-4,5-dimethoxy-benzyl]-pyrimidine-2,4-diamine (Example 11b)) there is obtained 5-[3-(3,5-dimethoxy-naphtalen-2-yl-ethynyl)-4,5-dimethoxy-benzyl]-pyrimidine-2,4-diamine as a brownish solid. Yield: 42%. M.p.=93°–103°.

12am) In analogy to Example 12h), with 5-bromoisatin and 5-[3-ethynyl-4,5-dimethoxy-benzyl]-pyrimidine-2,4-diamine (Example 11b)) there is obtained 5-[5-(2,4-diaminopyrimidin-5-ylmethyl)-2,3-dimethoxy-phenylethynyl]-1H-indole-2,4-dione as an orange solid. Yield: 19%. M.p.>250°.

12an) In analogy to Example 12h), with N-benzyl-5-bromo-isatin (G. Tacconi et al., J.Prakt.Chem. 315, 339 (1973)) and 5-[3-ethynyl-4,5-dimethoxy-benzyl]-pyrimidine-2,4-diamine (Example 11b)) there is obtained 5-[5-(2,4-diaminopyrimidin-5-ylmethyl)-2,3-dimethoxy-phenylethynyl]-1-benzyl-indole-2,4-dione as a red solid. Yield: 25%. Mass spectrum (ISP): peaks inter alia at m/e: 520 (M++H, 100%).

12ao) In analogy to Example 12h), with 5-iodovanillin and 5-[3-ethynyl-4,5-dimethoxy-benzyl]-pyrimidine-2,4-diamine (Example 11b)) there is obtained 3-[5-(2,4-diamino-pyrimidin-5-yl-methyl)-2,3-dimethoxy-phenylethynyl]-4-hydroxy-5-methoxy-benzaldehyde as a colourless solid. Yield: 14%. Mass spectrum (ISP): peaks inter alia at m/e: 435 (M++H, 100%).

12ap) In analogy to Example 12h), with 8-iodo-1,7-bismethoxy-naphthalene (Example 13ao)) and 5-[3-ethynyl-4,5-dimethoxy-benzyl]-pyrimidine-2,4-diamine (Example 11b) there is obtained 5-[3-(3,5-bis-methoxymethoxy-naphthalen-2-ylethynyl)-4,5-dimethoxy-benzyl]-pyrimidine-2,4-diamine as a brownish solid. Yield: 46%. M.p.=112°–117°.

12aq) In analogy to Example 12h), with 3-iodo-4,5-dimethoxy-benzaldehyde and 5-[3-ethynyl-4,5-dimethoxy-benzyl]-pyrimidine-2,4-diamine (Example 11b)) there is obtained 3-[5-(2,4-diamino-pyrimidin-5-ylmethyl)-2,3-dimethoxy-phenylethynyl]-4,5-dimethoxy-benzaldehyde as a yellowish solid. Yield: 14%. Mass spectrum: peaks inter alia at 449 (M+, 100%), 387 (10%).

12ar) In analogy to Example 12h), with 5-bromoisatin oxime (Example 13ap)) and 5-[3-ethynyl-4,5-dimethoxy-benzyl]-pyrimidine-2,4-diamine (Example 11b)) there is obtained 5-[5-(2,4-diamino-pyrimidin-5-ylmethyl)-2,3-dimethoxy-phenylethynyl]-1H-indole-2,3-dione 3-oxime as a yellowish solid. Yield: 9%. M.p.=105° (decomposition).

12as) In analogy to Example 12h), with N-benzyl-5-bromo-isatin oxime (Example 13aq)) and 5-[3-ethynyl-4,5-dimethoxy-benzyl]-pyrimidine-2,4-diamine (Example 11b) there is obtained 5-[5-(2,4-diamino-pyrimidin-5-ylmethyl)-2,3-dimethoxy-phenylethynyl]-1-benzyl-indole-2,3-dione 3-oxime as a yellow solid. Yield: 8%. Mass spectrum: peaks inter alia at 535 (M++H, 100%), 513(10%).

12at) In analogy to Example 12h), with cyclopropanecarboxylic acid acetyl-(3-iodo-phenyl)-amide (Example 13ar)) and 5-[3-ethynyl- 4,5-dimethoxy-benzyl]-pyrimidine-2,4-diamine (Example 11b) there is obtained cyclopropanecarboxylic acid acetyl-[3-[5-(2,4-diamino-pyrimidin-5-ylmethyl)-2,3-dimethoxy-phenylethynyl]-phenyl]-amide as a yellowish solid. Yield: 29%. M.p.=indefinite at approximately 135°.

12au) In analogy to Example 12h), with 3-iodo-4,5-dimethoxybenzaldehyde oxime (Example 13as) and 5-[3-ethynyl-4,5-dimethoxy-benzyl]-pyrimidine-2,4-diamine (Example 11b)) there is obtained 3-[5-(2,4-diamino-pyrimidin-5-ylmethyl)-2,3-dimethoxy-phenylethynyl]-4,5-dimethoxy-benzaldehyde oxime as a beige solid. Yield: 26%. Mass spectrum: peaks inter alia at 464 (M+, 100%).

12av) In analogy to Example 12h), with cyclopropanecarboxylic acid (2-cyano-ethyl)-(3-iodo-phenyl)-amide (Example 13at)) and 5-[3-ethynyl-4,5-dimethoxy-benzyl]-pyrimidine-2,4-diamine (Example 11b)) there is obtained cyclopropanecarboxylic acid (2-cyano-ethyl)-[3-[5-(2,4-diamino-pyrimidin-5-ylmethyl)-2,3-dimethoxy-phenylethynyl]-phenyl]-amide as a colourless solid. Yield: 32%. M.p.=127°–131°.

12ax) in analogy to Example 12h), with ethyl 7-bromo-4-oxo-1-(tetrahydro-furan-2-ylmethyl)-1,4-dihydro-quinoline-3-carboxylate (Example 13au)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-4-oxo-1-(tetrahydrofuran-2-ylmethyl)-1,4-dihydro-quinoline-3-carboxylate as a colourless solid. Yield: 14%. M.p.=136°.

12ay) In analogy to Example 12h), with ethyl 7-bromo-4-oxo-1-(furan-2-ylmethyl)-1,4-dihydro-quinoline-3-carboxylate (Example 13av)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-4-oxo-1-(furan-2-ylmethyl)-1,4-dihydro-quinoline-3-carboxylate as a colourless solid. Yield: 6%. Mass spectrum: peaks inter alia at m/e: 580.4 (M++H, 100%), 454.5 (35%).

12az) In analogy to Example 12h), with 3-iodo-4,5-dimethoxy-benzonitrile (Example 13ax)) and 5-[3-ethynyl-4,5-dimethoxy-benzyl]-pyrimidine-2,4-diamine (Example 11b)) there is obtained 3-[5-(2,4-diamino-pyrimidin-5-ylmethyl)-2,3-dimethoxy-phenylethynyl]-4,5-dimethoxy-benzonitrile as a colourless solid. Yield: 40%. M.p.=197°.

12ba) In analogy to Example 12h), from ethyl 3-iodo-4,5-dimethoxy-benzoate and 5-[3-ethynyl-4,5-dimethoxy-benzyl]-pyrimidine-2,4-diamine (Example 11b) there is obtained ethyl 3-[5-(2,4-diamino-pyrimidin-5-ylmethyl)2,3-dimethoxy-phenylethynyl]-4,5-dimethoxy-benzoate as a yellow solid. Yield: 63%. Mass spectrum: peaks inter alia at m/e: 492.2 (M+, 38%); 477.2 (18%); 134.0 (100%).

12bb) In analogy to Example 12h), from cyclopropanecarboxylic acid cyclopropancarbonyl-(3-iodo-phenyl)-amide (Example 13ay)) and 5-[3-ethynyl-4,5-dimethoxy-benzyl]-pyrimidine-2 , 4-diamine (Example 11b)) there is obtained cyclopropanecarboxylic acid cyclopropancarbonyl-[3-[5-(2,4-diamino-pyrimidin-5-ylmethyl)-2,3-dimethoxy-phenylethynyl]-phenyl]-amide as a yellowish resin. Yield 47%. Mass spectrum: peaks inter alia at m/e: 512.6 (M++H, 100%), 444 (12%), 426,6 (77%), 361.5 (60%).

12bc) In analogy to Example 12h), from ethyl 7-bromo-4-oxo-1-(tetrahydro-pyran-4-yl)-1,4-dihydro-quinoline-3-carboxylate (Example 13az)) and 5-[3-ethynyl-4,5-dimethoxy-benzyl]-pyrimidine-2,4-diamine (Example 11b)) there is obtained ethyl 7-[5-(2,4-diamino-pyrimidin-5-ylmethyl)-2,3-dimethoxy-phenylethynyl]-4-oxo-1-(tetrahydro-pyran-4-yl)-1,4-dihydro-quinoline-3-carboxylate as a colourless solid. Yield: 41%. M.p.=118°.

12bd) In analogy to Example 12h), from 1-(3-Iodo-4,5-dimethoxy-phenyl)-ethanone and 5-[3-ethynyl-4,5-dimethoxy-benzyl]-pyrimidine- 2,4-diamine (Example 11b)) there is obtained 1-[3-[5-(2,4-diamino-pyrimidin-5-ylmethyl)-2,3-dimethoxy-phenyl ethynyl]-4,5-dimethoxy-phenyl]-ethanone as a pink solid. Yield: 46%. Mass spectrum: peaks inter alia at m/e: 463 (M++H, 100%).

12be) In analogy to Example 12h), from 1-(3-iodo-4-hydroxy-5-methoxy-phenyl)-ethanone and 5-[3-ethynyl-4,5-dimethoxy-benzyl]-pyrimidine-2,4-diamine (Example 11b)) there is obtained 1-[3-[5-(2,4-diamino-pyrimidin-5-ylmethyl)-2,3-dimethoxy-phenylethynyl]-4-hydroxy-5-methoxy-phenyl]-ethanone as a yellowish solid. Yield: 39%. Mass spectrum: peaks inter alia at m/e: 449 (M++H, 100%); 387 (11%); 361 (15%).

12bf) In analogy to Example 12h), from ethyl 3-(3-iodo-4,5-dimethoxy-phenyl)-3-oxo-propionate (Example 13ba)) and 5-[3-ethynyl-4,5-dimethoxy-benzyl]-pyrimidine-2,4-diamine (Example 11b)) there is obtained ethyl 3-[3-[5-(2,4-diamino-pyrimidin-5-ylmethyl)-2,-3-dimethoxy-phenylethynyl]-4,5-dimethoxy-phenyl]-3-oxo-propionate as a yellow solid (keto/enol mixture). Yield: 49%. Mass spectrum: peaks inter alia at m/e: 535 (M+, 100%).

12bg) In analogy to Example 12h), from cyclopropanecarboxylic acid (3-iodo-phenyl)-amide (Example 13bb)) and 5-[3-ethynyl-4,5-dimethoxy-benzyl]-pyrimidine-2,4-diamine (Example 11b)) there is obtained cyclopropanecarboxylic acid [3-[5-(2,4-diamino-pyrimidin-5-ylmethyl)-2,3- dimethoxy-phenylethynyl]-phenyl]-amide as a brownish oil which solidifies after a few days. Yield: 11%. Mass spectrum: peaks inter alia at m/e: 444 (M++H, 100%).

12bh) In analogy to Example 12h), from furan-2-carboxylic acid (furan-2-carbonyl)-(3-iodo-phenyl)-amide (Example 13bc)) and 5-[3-ethynyl-4,5-dimethoxy-benzyl]-pyrimidine-2,4-diamine (Example 11b)) there is obtained furan-2-carboxylic acid [3-[5-(2,4-diamino-pyrimidin-5-ylmethyl)-2,3-dimethoxy-phenyl]-(furan-2-carbonyl)-amide as a colourless solid. Yield: 47%. Mass spectrum: peaks inter alia at m/e: 564 (M++H, 32%), 387 (17%).

12bi) In analogy to Example 12h), from (3-iodo-phenyl)-(tetrahydro-pyran-4-yl)-amine (Example 13bd)) and 5-[3-ethynyl-4,5-dimethoxy-benzyl]-pyrimidine-2,4-diamine (Example 11b)) there is obtained 5-[3,4-dimethoxy-5-[3-(tetrahydro-pyran-4-ylamino)-phenylethynyl]-benzyl]-pyrimidine-2,4-diamine as a yellowish solid. Yield: 23%. Mass spectrum: peaks inter alia at m/e: 460 (M++H, 100%), 387 (22%), 376 (20%), 361 (38%).

12bj) In analogy to Example 12h), from furan-2-carboxylic acid (3-iodo-phenyl)-amide (Example 13be)) and 5-[3-ethynyl-4,5-dimethoxy-benzyl]-pyrimidine-2,4-diamine (Example 11b)) there is obtained furan-2-carboxylic acid [3-[5-(2,4-diamino-pyrimidin-5-ylmethyl)-2,3-dimethoxy-phenylethynyl]-phenyl]-amide as a beige solid. Yield: 19%. Mass spectrum: peaks inter alia at m/e: 470 (M++H, 100%), 261 (10%).

12bk) In analogy to Example 12h), from cyclopropanecarboxylic acid (furan-2-carbonyl)-(3-iodo-phenyl)-amide and 5-[3-ethynyl-4,5-dimethoxy-benzyl]-pyrimidine-2,4-diamine (Example 11b)) there is obtained cyclopropanecarboxylic acid [3-[5-(2,4-diamino-pyrimidin-5-ylmethyl)-2,3-dimethoxy-phenylethynyl]phenyl]-(furan-2-carbonyl)-amide as a colourless solid. Yield: 20%. M.p.=128°.

12bl) In analogy to Example 12h), from cyclopropanecarboxylic acid (3-iodo-phenyl)-(tetrahydro-pyran-4-yl)-amide (Example 13bg)) and 5-[3-ethynyl-4,5-dimethoxy-benzyl]-pyrimidine-2,4-diamine (Example 11b)) there is obtained cyclopropanecarboxylic acid [3-[5-(2,4-diamino-pyrimidin-5-ylmethyl)-2,3-dimethoxy-phenylethynyl]-phenyl]-(tetrahydro-pyran-4-yl)-amide as a beige solid. Yield: 62%. Mass spectrum: peaks inter alia at m/e: 528 (M++H, 100%), 387 (30%), 339 (28%).

12bm) In analogy to Example 12h), from N-cyclopropyl-2-hydroxy-5-iodo-benzamide (Example 13bh)) and 5-[3-ethynyl-4,5-dimethoxy-benzyl]-pyrimidine-2,4-diamine (Example 11b)) there is obtained N-cyclopropyl-5-[5-(2,4-diamino-pyrimidin-5-ylmethyl)- 2,3-dimethoxy-phenylethynyl}-2-hydroxy-benzamide as a yellow solid. Yield: 15%. Mass spectrum: peaks inter alia at m/e: 460.3 (M++H, 100%).

12bn) In analogy to Example 12h), from tert.butyl [(3-iodophenylcarbamoyl)-methyl]-carbamate (Example 13bi)) and 5-[3-ethynyl-4,5-dimethoxy-benzyl]-pyrimidine-2,4-diamine (Example 11b)) there is obtained tert.butyl ([3-[5-(2,4-diamino-pyrimidin-5-ylmethyl)-2,3-dimethoxy-phenylethynyl]-phenylcarbamate as pale pink crystals. Yield: 16%. M.p.=111°.

12bo) In analogy to Example 12h), from diethyl (4-bromo-phenyl)-phosphonate (Hirao et al., Synthesis 1981, 56) and 5-[3-ethynyl-4,5-dimethoxy-benzyl]-pyrimidine-2,4-diamine (Example 11b)) there is obtained diethyl [4-[5-(2,4-diamino-pyrimidin-5-yl-methyl)-2,3-dimethoxy-phenylethynyl]-phenyl]-phosphonate as a colourless solid. Yield: 68%. M.p.=193°-197°.

12bp) In analogy to Example 12h), from N-(di-pyridin-2-yl-methyl)-3-iodo-benzamide (Example 13bj)) and 5-[3-ethynyl-4,5-dimethoxy-benzyl]-pyrimidine-2,4-diamine (Example 11b)) there is obtained 3-[5-(2,4-diamino-pyrimidin-5-ylmethyl)-2,3-dimethoxy-phenylethynyl]-N-(di-pyridin-2-yl-methyl)-benzamide as a yellowish solid. Yield: 60%. M.p.=115°-120° (decomposition).

12bq) In analogy to Example 12h), with ethyl 7-bromo-1-[2-(tert-butyl-dimethyl-silanyloxy)-1,1-dimethyl-ethyl]-4-oxo-1,4-dihydro-quinoline-3-carboxylate (Example 13bm)) there is obtained ethyl 1-[2-(tert-butyl-dimethyl-silanyloxy)-1,1-dimethyl-ethyl]-7-[5-(2,4-diamino-pyrimidin-5-ylmethyl)-2,3-dimethoxy-phenylethynyl]-4-oxo-1,4-dihydro-quinoline-3-carboxylate. Yield: 84%. Mass spectrum (ISP) peaks inter alia at 686 (M+H, 100%), 454 (8%), 343.7 (23%).

12br) In analogy to Example 12h), with ethyl [E/Z]-2-(4-bromo-2-chloro-benzoyl)-3-dimethylaminoacrylate (Example 13bk)) there is obtained ethyl [E/Z]-2-{2-chloro-4-[5-(2,4-diamino-pyrimidin-5-ylmethyl)-2,3-dimethoxy-phenylethynyl]-benzoyl}- 3-dimethylamino-acrylate. Yield: 88%. Mass spectrum (ISP) peaks inter alia at 564 (M+H, 100%), 259 (12%).

12bs) In analogy to Example 12h), with (4-bromophenyl)-cyclopropyl-methanone there is obtained cyclopropyl-{4-[5-(2,4-diamino-pyrimidin-5-ylmethyl)-2,3-dimethoxy-phenylethynyl]-phenyl}-methanone. Yield: 74%. M.p. 250°.

12bt) In analogy to Example 12h), with ethyl 3-(4-bromophenyl)-3-oxo-propionate (Example 13bn)) there is obtained ethyl 3-{4-[5-(2,4-diamino-pyrimidin-5-ylmethyl)-2,3-dimethoxy-phenyl-ethynyl]-phenyl}-3-oxo-propionate. Yield: 33%. M.p. 228°.

12bu) In analogy to Example 12h), with (7S,8R,9R,10S,22S,23R, 24R, 25S)-7,8,9,10,22,23,24,25-octaacetoxy-3, 18-dibromo-5,6,7,8,9,10,20,21,22,23,24,25,26-tetracahydro-5,29:14,20-dimetheno-dibenzo[b,o][7,20,1,14] dioxadiazacyclohexacosin-13,15,28,30-tetraone (Example 13bo)) there is obtained (7S, 8R, 9R, 10S,22S,23R,24R,25S) -7,8,9,10,22,23,24,25-octaacetoxy-3,18-bis-[5-(2,4-diamino-pyrimidin-5-ylmethyl)-2,3-dimethoxy-phenyl-ethynyl]-5,6,7,8,9,10,20,21,22,23,24,25,26-tetracahydro-5, 29: 14,20-dimethenodibenzo[b,o][7,20,1,14] dioxadiazacyclohexacosin-13,15,28,30-tetraone. Yield: 70%. M.p. 198°.

12bv) In analogy to Example 12h), with ethyl [E/Z]-3-(4-bromophenyl)-2-hydroxyimino-3-oxo-propionate (Example 13bp)) there is obtained ethyl [E/Z]-3-{4-[5-(2,4-diamino-pyrimidin-5-yl-methyl)-2,3-dimethoxy-phenylethynyl]-phenyl}-2-hydroxyimino-3-oxo-propionate. Yield: 62%. M.p. 223° (decomposition). Mass spectrum (ISP) peaks inter alia at 504 (M+H, 100%).

12bw) In analogy to Example 12h), with ethyl [E/Z]-3-(4-bromophenyl)-2-(2-methoxy-ethoxyimino)-3-oxo-propionate (Example 13bq)) there is obtained ethyl [E/Z]-3-{4-[5-(2,4-diamino-pyrimidin-5-ylmethyl)-2,3-dimethoxy-phenylethinyl]-phenyl}-2-(2-methoxy-ethoxyimino)-3-oxo-propionate. Yield: 70%. M.p. 117° (decomposition). Mass spectrum (ISP) peaks inter alia at 562 (M+H, 100%), 548 (5%).

12bx) In analogy to Example 12h), with ethyl [E/Z]-3-(4-bromophenyl)-2-methoxyimino-3-oxo-propionate (Example 13br)) there is obtained ethyl [E/Z]-3-{4-[5-(2,4-diamino-pyrimidin-5-yl-methyl)-2,3-dimethoxy-phenylethynyl]-phenyl}-2-methoxyimino-3-oxo-propionate. Yield: 74%. M.p. 112° (decomposition). Mass spectrum (ISP) peaks inter alia at 518 (M+H, 100%).

12by) In analogy to Example 12h), with ethyl [E/Z]-3-(4-bromo-2-chlorophenyl)-2-trityloxyimino-3-oxopropionate (Example 13bu)) there is obtained ethyl [E/Z]-3-{2-chloro-4-[5-(2,4-diamino-pyrimidin-5-ylmethyl)-2,3-dimethoxy-phenylethynyl]-phenyl}-3-oxo-2-trityloxyimino-propionate. Yield: 72%. M.p. 110° (decomposition). Mass spectrum (ISP) peaks inter alia at 780 (M+H, 100%), 538 (10%).

12bz) In analogy to Example 12h), with N-(4-bromophenyl)-C,C,C-trifluoro-methanesulphonamide (Example 13bv)) there was obtained N-[4-[5-(2,4-diamino-pyrimidin-5-ylmethyl)-2,3-dimethoxy-phenylethinyl]-phenyl]-C,C,C-trifluoro-methanesulphonamide as a pale yellow solid with m.p. 255°–260° (dec.). Yield: 12%.

12ca) In analogy to Example 12h), with N-(4-bromophenyl)-C,C,C-trifluoro-N-(4-methoxybenzyl)-methanesulphonamide (Example 13w)) there was obtained N-[4-[5-(2,4-diamino-pyrimidin-5-yl-methyl)-2,3-dimethoxy-phenylethynyl]-phenyl]-C,C,C-trifluoro-N-(4-methoxy-benzyl)-methanesulphonamide. This was dissolved in tetrahydrofuran, made acid with hydrogen chloride dissolved in diethyl ether, evaporated and the residue was digested in diethyl ether. N-[4-[5-(2,4-Diamino-pyrimidin-5-ylmethyl)-2,3-dimethoxy-phenylethynyl]-phenyl]-C,C,C-trifluoro-N-(4-methoxybenzyl)-methanesulphonamide 1:1 hydrochloride was obtained as a pale yellow solid with m.p. 200°–205° (dec.). Yield: 65%.

12cb) In analogy to Example 12ca), with N-(4-bromophenyl)-N-ethyl-C,C,C-trifluoro-methanesulphonamide (Example 13bx)) there was obtained N-[4-[5-(2,4-diamino-pyrimidin-5-ylmethyl)- 2,3-dimethoxy-phenylethynyl]-phenyl]-N-ethyl-C,C,C-trifluoro-methanesulphonamide 1:1 hydrochloride as a colourless solid with m.p. 240°–243° (dec.). Yield: 58%.

12cc) In analogy to Example 12h), with N-(4-bromophenyl)-N-methyl-C,C,C-trifluoro-methanesulphonamide (Example 13by)) there was obtained N-[4-[5-(2,4-diamino-pyrimidin-5-ylmethyl)-2,3-dimethoxy-phenylethynyl]-phenyl]-N-methyl-C,C,C-trifluoro-methanesulphonamide as a colourless solid with m.p. 117°–118°. Yield: 26%.

12cd) In analogy to Example 12h), with N-(4-bromophenyl)-N-isobutyl-C,C,C-trifluoro-methanesulphonamide (Example 13bz)) there was obtained N-[4-[5-(2,4-diamino-pyrimidin-5-ylmethyl)-2,3-dimethoxy-phenylethynyl]-phenyl]-N-isobutyl-C,C,C-trifluoro-methanesulphonamide as a colourless solid with m.p. 185°–186°. Yield: 42%.

12ce) In analogy to Example 12h), with ethyl [(4-bromophenyl)-(trifluoro-methylsulphonyl)-amino]-acetate (Example 13ca)) there was obtained ethyl [4-[5-(2,4-diamino-pyrimidin-5-yl-methyl)-2,3-dimethoxy-phenylethynyl]-phenyl]-trifluoro-methylsulphonyl)-amino]-acetate as a yellow foam. Yield: 28%. MS (ISP): 594.3 ([M+H]⁺, 100%).

12cf) In analogy to Example 12h), with N-(3-bromophenyl)-N-methyl-C,C,C-trifluoro-methanesulphonamide (Example 13cc)) there was obtained N-[3-[5-(2,4-diamino-pyrimidin-5-ylmethyl)-2,3-dimethoxy-phenylethynyl]-phenyl]-N-methyl-C,C,C-trifluoro-methanesulphonamide. After recrystallization from ethyl acetate/diethyl ether there was obtained a colourless solid with m.p. 197°–198°. Yield: 29%.

12cg) In analogy tom Example 12h), with N-(3-bromophenyl)-N-ethyl-C,C,C-trifluoromethanesulphonamide (Example 13cd)) there was obtained N-[3-[5-(2,4-diamino-pyrimidin-5-ylmethyl)-2,3-dimethoxy-phenylethinyl]-phenyl]-N-ethyl-C,C,C-trifluoro-methanesulphonamide. After recrystallization from ethyl acetate/diethyl ether there was obtained a colourless solid with m.p. 192°–194°. Yield: 54%.

EXAMPLE 13

Preparation of (hetero)aromatic compounds IV

13a) A suspension of 1.2 g of ethyl 1-ethyl-6,7-difluoro-1,4-dihydro-4-oxo-quinoline-3-carboxylate (European Offenlegungsschrift No. 230053, C.A. 108:112498) in 25 ml of 2N aqueous sodium hydroxide solution is heated at reflux for 4 hrs. After cooling to room temperature the reaction mixture is adjusted to pH 3 to 4 with 37% aqueous hydrochloric acid and the precipitate is filtered off under suction, washed with 200 ml of water and 200 ml of diethyl ether and dried. 980 mg (91%) of 1-ethyl-6-fluoro-7-hydroxy-1,4-dihydro-4-oxo-quinoline-3-carboxylic acid are isolated as a colourless solid. M.p.>250°.

13b) A suspension of 0.9 g of 1-ethyl-6-fluoro-7-hydroxy-1,4-dihydro-4-oxo-quinoline-3-carboxylic acid in 10 ml of pyridine is treated with 1.6 ml of trifluoromethanesulphonic anhydride at 0° and stirred at room temperature for 5 hrs. 5 ml of ethanol are slowly added dropwise thereto and the mixture is stirred for a further 1 hr. The reaction mixture is poured into 100 ml of water, adjusted to pH 4 with 37% aqueous hydrochloric acid and extracted three times with 50 ml of ethyl acetate each time. The combined organic phases are washed with 100 ml of water and 100 ml of saturated, aqueous sodium chloride solution, dried over magnesium sulphate and concentrated. The residue is chromatographed on silica gel with ethyl acetate. 0.61 g (41%) of ethyl 1-ethyl-6-fluoro-4-oxo-1,4-dihydro-7-[[(trifluoromethyl)-sulphonyl]oxy]-quinoline-3-carboxylate is isolated as a yellowish solid. M.p. 83°–85°.

13c) In analogy to Example 13b), from 6-hydroxy-naphthalene-2-carboxylic acid (J. Chem. Soc. 123, 1652 (1923)) there is obtained ethyl 6-(trifluoro-methanesulphonyloxy)-naphthalene-2-carboxylate as a colourless solid. Yield: 83%. Mass spectrum: peaks: inter alia at 348 (M+, 78%), 303 (31%), 215 (100%).

13d) A solution of 6-iodo-pyridine-3-carboxylic acid (J. Am. Chem. Soc. 72, 1032, (1950)), 1.2 g of trimethyl o-formate and 0.2 g of p-toluenesulphonic acid in 75 ml of methanol is held at reflux for 2 hrs. The reaction mixture is concentrated and the residue is taken up in 50 ml of diethyl ether. The ether phase is washed twice with 50 ml of 2N aqueous sodium hydroxide solution each time and twice with 50 ml of saturated, aqueous sodium chloride solution each time, dried over magnesium sulphate and concentrated. The residue is recrystallized from 30 ml of hot methanol. 1.15 g (43%) of methyl 6-iodo-pyridine-3-carboxylate are isolated as a colourless solid. M.p. 134°–135°.

13e) A suspension of 4.04 g of ethyl 7-bromo-4-hydroxy-quinoline-3-carboxylate (J. Am. Chem. Soc. 71,3226, (1949)) and 4.71 g of potassium carbonate in 30 ml of dimethylformamide is treated with 9.68 g of methyl iodide at room temperature. The reaction mixture is heated to 90° and stirred at this temperature for 3 hrs. The reaction mixture is concentrated in a high vacuum. The residue is suspended in 50 ml of water, filtered off under suction and washed with 50 ml of water. Recrystallization of the crude product from ethanol/diethyl ether yields 3.67 g (86%) of ethyl 7-bromo-1-methyl-4-oxo-1,4-dihydro-quinoline-3-carboxylate as a colourless solid. M.p. 189°–191°.

13f) In analogy to Example 13e), from ethyl 7-bromo-4-hydroxy-quinoline-3-carboxylate and benzyl bromide there is obtained ethyl 1-benzyl-7-bromo-1-methyl-4-oxo-1,4-dihydro-quinoline-3-carboxylate as a colourless solid. Yield: 70%. Mass spectrum: peaks inter alia at 387 (M+, 4%), 385 (3%), 313(18%), 91 (100%).

13g) In analogy to Example 13e), from ethyl 4-hydroxy-7-iodo-quinoline-3-carboxylate (J. Am. Chem. Soc. 71,3226, (1949)) and ethyl iodide there is obtained ethyl 1-ethyl-7-iodo-4-oxo-1,4-dihydro-quinoline-3-carboxylate as a colourless solid. Yield: 78%. M.p. 130°–132°.

13h) In analogy to Example 13 e), from ethyl 6-bromo-4-hydroxy-quinoline-3-carboxylate (J. Chem. Soc. 1950, 384–388) and ethyl iodide there is obtained ethyl 1-ethyl-6-bromo-4-oxo-1,4-dihydro-quinoline-3-carboxylate as a colourless solid. Yield: 92%. M.p. 128°–130°.

13i) In analogy to Example 13e), from ethyl 4-hydroxy-7-iodo-quinoline-3-carboxylate (J. Am. Chem. Soc. 1949, 71,3226) and 1-propyl iodide there is obtained ethyl 7-iodo-4-oxo-1-propyl-1,4-dihydro-quinoline-3-carboxylate as a colourless solid. Yield: 56%. M.p. 128°–130°.

13j) In analogy to Example 13e), from ethyl 4-hydroxy-7-iodo-quinoline-3-carboxylate (J. Am. Chem. Soc. 1949, 71,3226) and bromomethyl-cyclopropane there is obtained ethyl 1-cyclopropylmethyl-7-iodo-4-oxo-1,4-dihydro-quinoline-3-carboxylate as a beige solid. Yield: 73%. M.p. 128°–130°.

13k) In analogy to Example 13e), from ethyl 4-hydroxy-7-iodo-quinoline-3-carboxylate (J. Am. Chem. Soc. 1949, 71,3226) and 2-bromoethanol there is obtained ethyl 1-(2-hydroxyethyl)-7-iodo-4-oxo-1,4-dihydro-quinoline-3-carboxylate as a beige solid. Yield: 59%. M.p. 196°–198°.

13l) In analogy to Example 13e), from ethyl 4-hydroxy-7-iodo-quinoline-3-carboxylate (J. Am. Chem. Soc. 1949, 71,3226) and triethylene glycol mono-iodohydrin there is obtained ethyl 1-{2-[2-(2-hydroxy-ethoxy)-ethoxy]-ethyl}-7-iodo-4-oxo-1,4-dihydro-quinoline-3-carboxylate as a colourless solid. Yield: 43%. M.p. 104°–106°.

13m)ma) A suspension of 66 g of 2-chloro-4-iodo-benzoic acid (I.G.Farbenind. D.R.P. 565411 1930) in 690 ml of benzene is treated at 4° C. with 20.56 ml of thionyl chloride and 0.1 ml of dimethylformamide and the mixture is boiled at reflux under argon for 21 hrs. The reaction mixture is concentrated. Distillation of the residue at 160°/60 Pa yields 51.9 g (74%) of 2-chloro-4-iodo-benzoyl chloride as a colourless liquid.

mb) 4.2 g of magnesium shavings are suspended in 8.3 ml of anhydrous ethanol and treated with 0.83 ml of carbon tetrachloride. A solution of 27.63 g of diethyl malonate in 17 ml of ethanol and 62 ml of toluene is added dropwise in such a manner that the temperature remains at 50°–60°. Subsequently, the mixture is heated at 60° for a further 1 hr. The reaction mixture is cooled to –30° and a solution of 51.9 g 2-chloro-4-iodo-benzoyl chloride in 70 ml of anhydrous toluene is added dropwise within 30 min. The reaction mixture is stirred while slowly warming to room temperature within 1.30 hrs., then cooled to 0° and treated dropwise with a solution of 4 ml of conc. sulphuric acid in 60 ml of water. After 20 min. the phases are separated and the aqueous solution is back-extracted twice with 100 ml of toluene each time. The combined organic phases are washed with 100 ml of saturated, aqueous sodium chloride solution, dried over magnesium sulphate and concentrated. 70.3 g (96%) of diethyl 2-(2-chloro-4-iodo-benzoyl)-malonate are obtained as a yellowish oil. Mass spectrum: peaks inter alia at 424 (M+, 0.4%), 389 (48%), 343 (63%), 265 (100%).

mc) 70.3 g of diethyl 2-(2-chloro-4-iodo-benzoyl)-malonate are heated to boiling under reflux for 6 hrs. while stirring vigorously with 750 ml of water and 0.75 g of p-toluenesulphonic acid. The reaction mixture is cooled to room temperature and extracted three times with 200 ml of diethyl ether each time. The ether phases are washed twice with 200 ml of saturated, aqueous sodium chloride solution each time, dried over magnesium sulphate and concentrated. 53.7 g (92%) of ethyl 3-(2-chloro-4-iodo-phenyl)-3-oxo-propionate are obtained as a yellowish oil. Mass spectrum: peaks inter alia at 352 (M+, 3%), 317 (73%), 289 (19%), 265 (100%).

md) 53.7 g of ethyl 3-(2-chloro-4-iodo-phenyl)-3-oxo-propionate are heated to boiling under reflux for 4 hrs. with 40 g of triethyl orthoformate and 46.1 g of acetic anhydride. The volatile constituents are distilled off in a water-jet vacuum and finally in a high vacuum. 55.9 g (90%) of ethyl 2-(2-chloro-4-iodo-benzoyl)-3-ethoxy-acrylate are obtained as a yellowish oil. Mass spectrum: peaks inter alia at 408 (M+, 4%), 373 (67%), 342 (14%), 335 (100%).

mf) A solution of 31.18 g of ethyl 2-(2-chloro-4-iodo-benzoyl)-3-ethoxy-acrylate in 500 ml of methylene chloride is treated dropwise with 7.95 g of cyclohexylamine while cooling with ice and stirring. After 6 hrs. at room temperature the reaction mixture is concentrated and, for crystallization, the residue is stirred with 200 ml of hexane. The precipitate is filtered off under suction, washed with 100 ml of hexane and dried. 19.2 g (55%) of ethyl 2-(2-chloro-4-iodo-benzoyl)-3-cyclohexylamino-acrylate are obtained as a colourless solid. M.p. 154°–156° C.

mg) A suspension of 17.8 g of ethyl 2-(2-chloro-4-iodo-benzoyl)-3-cyclohexylamino-acrylate in 150 ml of dimethyl sulphoxide is treated portionwise at room temperature while stirring with 4.75 g of potassium tert-butylate and the mixture is subsequently heated at 50° for 1 hr. The mixture is left to cool to room temperature, poured into 500 ml of ice-water and stirred for a further 30 min. The suspension is suction filtered, the filter residue is washed three times with 100 ml of water each time and three times with 100 ml of hexane each time and dried. Recrystallization of the crude product from ethyl acetate/hexane yields 14.8 g (90%) of ethyl 1-cyclohexyl-7-iodo-4-oxo-1,4-dihydro-quinoline-3-carboxylate as a colourless solid. M.p. 169°–171° C.

13n) In analogy to Example 13m), from ethyl 2-(2-chloro-4-iodo-benzoyl)-3-ethoxy-acrylate and 4-picolylamine there is obtained 7-iodo-4-oxo-1-(pyridin-4-yl)methyl-1,4-dihydro-quinoline-3-carboxylate as a colourless solid. Yield: 18%. M.p. 198°–201°.

13o) In analogy to Example 13m), from ethyl 2-(2-chloro-4-iodo-benzoyl)-3-ethoxy-acrylate and cyclopentylamine there is obtained 1-cyclopentyl-7-iodo-4-oxo-1,4-dihydro-quinoline-3-carboxylate as a colourless solid. Yield: 64%. M.p. 148°–150°.

13p) In analogy to Example 13m), from ethyl 2-(2-chloro-4-iodo-benzoyl)-3-ethoxy-acrylate and adamantylamine there is obtained 1-adamantan-1-yl-7-iodo-4-oxo-1,4-dihydro-quinoline-3-carboxylate as a colourless solid. Yield: 53%. M.p.>250°. Mass spectrum (ISP): 478(M++H).

13q) In analogy to Example 13m), from ethyl 2-(2-chloro-4-iodo-benzoyl)-3-ethoxy-acrylate and ( )-exo-norbornylamine there is obtained ( )-1-exo-bicyclo[2.2.1]hept-2-yl-7-iodo-4-oxo-1,4-dihydro-quinoline-3-carboxylate as a colourless solid. Yield: 65%. M.p. 237°–240°.

13r) In analogy to Example 13m), from ethyl 2-(2-chloro-4-iodo-benzoyl)-3-ethoxy-acrylate and 1,1,3,3-tetramethyl-butylamine there is obtained 7-iodo-4-oxo-1-(1,1,3,3-tetramethyl-butyl)-1,4-dihydro-quinoline-3-carboxylate as a colourless solid. Yield: 42%. M.p. 154°–156°.

13s) In analogy to Example 13m), from ethyl 2-(2-chloro-4-iodo-benzoyl)-3-ethoxy-acrylate and tert-butylamine there is obtained 1-tert-butyl-7-iodo-4-oxo-1,4-dihydro-quinoline-3-carboxylate as a colourless solid. Yield: 48%. M.p. 169°–171°.

13t) In analogy to Example 13m), from ethyl 2-(2-chloro-4-iodo-benzoyl)-3-ethoxy-acrylate and trans-4-tert-butoxycarbonylamino-cyclohexyl-amine there is obtained 1-(trans-4-tert-butoxycarbonylamino-cyclohexyl)-7-iodo-4-oxo-1,4-dihydro-quinoline-3-carboxylate as a colourless solid. Yield: 35%. M.p. 137°–140°.

13u) In analogy to Example 13m), from ethyl 2-(2-chloro-4-iodo-benzoyl)-3-ethoxy-acrylate and 4-(aminomethyl)-piperidine there is obtained 7-iodo-4-oxo-1-piperidin-4-ylmethyl-1,4-dihydro-quinoline-3-carboxylate as a colourless solid. Yield: 45%. M.p. 154°–156°.

13v) In analogy to Example 13m), from ethyl 2-(2-chloro-4-iodo-benzoyl)-3-ethoxy-acrylate and cyclopropylamine there is obtained 1-cyclopropyl-7-iodo-4-oxo-1,4-dihydro-quinoline-3-carboxylate as a colourless solid. Yield: 52%. M.p. 198°–201°.

13w) In analogy to Example 13m), from ethyl 2-(2-chloro-4-iodo-benzoyl)-3-ethoxy-acrylate and 2,2,2-trifluoro-ethylamine there is obtained 7-iodo-4-oxo-(2,2,2-trifluoro-ethyl)-1,4-dihydro-quinoline-3-carboxylate as a colourless solid. Yield: 38%. M.p. 200°–202°.

13x) In analogy to Example 13m), from ethyl 2-(2-chloro-4-iodo-benzoyl)-3-ethoxy-acrylate and aniline there is obtained 7-iodo-4-oxo-1-phenyl-1,4-dihydro-quinoline-3-carboxylate as a colourless solid. Yield: 61%. M.p.>220°. Mass spectrum: peaks inter alia at 419 (M+, 9%), 374 (12%), 347 (100%), 246 (11%).

13y) A suspension of 2.4 g of ethyl 1-ethyl-7-iodo-4-oxo-1,4-dihydro-quinoline-3-carboxylate (Example 13 g)) in 20 ml of ethanol and 6 ml of water is treated at 0° with 325 mg of lithium hydroxide monohydrate. After 3 hrs. the reaction mixture is acidified with 25% aqueous hydrochloric acid. The precipitated substance is filtered off under suction, washed with 20 ml of water, 20 ml of ethanol and 20 ml of ether and dried. 2.1 g (94%) of 1-ethyl-7-iodo-4-oxo-1,4-dihydro-quinoline-3-carboxylic acid are obtained as a colourless solid. M.p. 237°–238°.

13z) A suspension of 0.68 g of 1-ethyl-7-iodo-4-oxo-1,4-dihydro-quinoline-3-carboxylic acid (Example 13y)) in 20 ml of methylene chloride is treated at 0° while stirring with 0.5 g of oxalyl chloride and 0.02 g of dimethylformamide. The reaction mixture is stirred at 0° C. for 1 hr. and at room temperature for 3 hrs. The reaction mixture is concentrated, the residue is dissolved in 50 ml of methylene chloride and again concentrated and dried. The yellow crude 1-ethyl-7-iodo-4-oxo-1,4-dihydro-quinoline-3-carbonyl chloride is dissolved in 25 ml of methylene chloride and treated dropwise at 0° C. with a solution of 0.3 g of dimethylaminopropylamine in 5 ml of methylene chloride. The reaction mixture is warmed to room temperature and stirred for 2 hrs. The methylene chloride solution is washed twice with 25 ml of a 2N aqueous hydrochloric acid solution each time. The acid solution is treated with 100 ml of a 2N aqueous sodium hydroxide solution and extracted three times with 50 ml of methylene chloride each time. The combined organic phases are dried over magnesium sulphate and concentrated. The residue is chromatographed on silica gel with methylene chloride/methanol/conc. ammonium hydroxide 90/9.9/0.1. 0.425 g (50%) of 1-ethyl-7-iodo-4-oxo-1,4-dihydro-quinoline-3-carboxylic acid (3-dimethylamino-propyl)-amide is isolated as a colourless solid. The crude product is recrystallized from methylene chloride/tert-butyl methyl ether. M.p. 161°–162°.

13aa) In analogy to Example 13z), from 1-ethyl-7-iodo-4-oxo-1,4-dihydro-quinoline-3-carboxylic acid and ethanolamine there is obtained 1-ethyl-7-iodo-4-oxo-1,4-dihydro-quinoline-3-carboxylic acid (2-hydroxy-ethyl)-amide as a colourless solid. Yield: 90%. M.p. 214°–216°.

13ab) In analogy to Example 13z), from 1-ethyl-7-iodo-4-oxo-1,4-dihydro-quinoline-3-carboxylic acid and 2-dimethylamino-ethanol there is obtained 2-dimethylamino-ethyl 1-ethyl-7-iodo-4-oxo-1,4-dihydro-quinoline-3-carboxylate as a beige amorphous solid. Yield: 78%. Mass spectrum (ISP): 415 (M++H).

13ac) 30.2 g of ethyl 3-dimethylaminoacrylate and 29.3 ml of triethylamine are dissolved in 180 ml of toluene and boiled at reflux. At this temperature a solution of 53 g of 4-bromo-2-chloro-benzoyl chloride (U.S. Pat. No. 4,959,363) in 50 ml of toluene is added dropwise over 30 min. and the mixture is subsequently heated at reflux for a further 1 hr. The mixture is left to cool to room temperature and is stirred in an ice bath for a further 30 min. The suspension is filtered and the precipitated triethylamine hydrochloride is washed with 40 ml of ice-cold toluene. The filtrate is concentrated to half of its volume and then, for crystallization, diluted with 100 ml of hexane and stirred in an ice bath for 1 hr. 51.2 g (67%) of ethyl 2-(4-bromo-2-chloro-benzoyl)-3-dimethylaminoacrylate are obtained as colourless crystals. M.p. 100°–101°.

13ad) A solution of 20 g of ethyl 2-(4-bromo-2-chloro-benzoyl)-3-dimethylaminoacrylate (Example 13ac)) in 200 ml of dimethyl sulphoxide is treated with 5.5 g of cyclohexylamine and stirred at room temperature under argon for 45 min. Immediately after the addition the solution begins to decolourize and a colourless, gel-like substance separates. 6.84 g of potassium tert-butylate are added in one portion to this suspension. The resulting suspension is stirred at room temperature for 10 min. and subsequently heated to 50° for 1.5 hrs. The reaction mixture is left to cool to room temperature, poured into 600 ml of ice-water and stirred for a further 30 min. The suspension is suction filtered, the filter residue is washed three times with 100 ml of water each time and three times with 100 ml of hexane each time and dried. Recrystallization of the crude product from ethyl acetate/hexane yields 14.8 g (90%) of ethyl 7-bromo-1-cyclohexyl-4-oxo-1,4-dihydro-quinoline-3-carboxylate as a colourless solid. M.p. 129°–133°.

13ae) In analogy to Example 13y), from ethyl 7-bromo-1-cyclohexyl-4-oxo-1,4-dihydro-quinoline-3-carboxylate (Example 13ad)) there is obtained 7-bromo-1-cyclohexyl-4-oxo-1,4-dihydro-quinoline-3-carboxylic acid as a colourless solid. Yield 87%. M.p. 251°–252°.

13af) In analogy to Example 13ab), from 7-bromo-1-cyclohexyl-4-oxo-1,4-dihydro-quinoline-3-carboxylic acid (Example 13ae)) and 2-(diisopropylamino)-ethanol there is obtained 2-diisopropylamino-ethyl 7-bromo-1-cyclohexyl-4-oxo-1,4-dihydro-quinoline-3-carboxylate as a pale yellow amorphous solid. Yield: 38%. Mass spectrum (ISP): 479.3 (M++H, 100%).

13ag) In analogy to Example 13ab), from 7-bromo-1-cyclohexyl-4-oxo-1,4-dihydro-quinoline-3-carboxylic acid (Example 13ae)) and N-(-2-hydroxyethyl)-morpholine there is obtained 2-morpholin- 4-yl-ethyl 7-bromo-1-cyclohexyl-4-oxo-1,4-dihydro-quinoline-3-carboxylate as a colourless amorphous solid. Yield: 60%. Mass spectrum (ISP): 463 (M++H, 100%).

13ah) In analogy to Example 13ma), from 2,4-dibromo-3-methoxy-benzoic acid (U.S. Pat. No. 5,026,896) there is obtained 2,4-dibromo-3-methoxy-benzoyl chloride as a colourless liquid. Yield: 98%. Mass spectrum: peaks inter alia at 328 (M+, 15%), 293 (100%), 278 (6%), 250 (16%).

13aha) In analogy to Example 13ac) and 13ad), from 2,4-dibromo-3-methoxy-benzoyl chloride (Example 13ah) after successive treatment with ethyl 3-dimethylaminoacrylate and cyclohexylamine there is obtained ethyl 7-bromo-1-cyclohexyl-8-methoxy-4-oxo-1,4-dihydro-quinoline-3-carboxylate. Yield: 55%. M.p. 123°–126°.

13ai) 22.6 g of diethyl 2-(2-chloro-4-iodo-benzoyl)-malonate (Example 13mb)) are heated to boiling under reflux with 250 ml of water and 0.75 g of p-toluenesulphonic acid while stirring vigorously for 24 hrs. The reaction mixture is cooled to room temperature and extracted three times with 200 ml of diethyl ether each time. The ether phases are washed twice with 200 ml of saturated, aqueous sodium chloride solution each time, dried over magnesium sulphate and concentrated. The residue is distilled in a high vacuum. 11.8 g (79%) of 2-chloro-4-iodo-acetophenone are obtained as a colourless liquid. B.p. 145°/70 Pa. Mass spectrum: peaks inter alia at 280(M+, 11%), 265(100%), 237(13%), 138(16%).

13aj) A mixture of 1 g of ethyl 7-bromo-1-cyclohexyl-4-oxo-1,4-dihydro-quinoline-3-carboxylate (Example 13ad)), 60 mg of palladium tetrakis-triphenylphosphine, 1.55 ml of tributyl-vinyl-stannate and 5 mg of 2,6-di-tert-butyl-4-methyl-cresol in 25 ml of toluene is heated at reflux for 1 hr. The reaction mixture is cooled to room temperature, treated with 100 ml of ethyl acetate and washed with 100 ml of 10% aqueous ammonia solution. The aqueous solution is extracted with 50 ml of ethyl acetate. The combined organic phases are washed with 100 ml of saturated aqueous sodium chloride solution, dried over magnesium sulphate and concentrated. The residue is chromatographed on silica gel with hexane/ethyl acetate 1:1. 0.646 g (75%) of ethyl 1-cyclohexyl-4-oxo-7-vinyl-1,4-dihydro-quinoline-3-carboxylate is obtained as a colourless amorphous solid. Mass spectrum (ISP): 326.3(M++H, 100%).

13ak) In analogy to Example 13a), from ethyl 1-cyclohexyl-6,7,8-trifluoro-4-oxo-1,4-dihydro-quinoline-carboxylate (J. Med. Chem. 31, 991–1001, (1988)) there is obtained 1-cyclohexyl-6,8-difluoro-7-hydroxy-4-oxo-1,4-dihydro-quinoline-carboxylic acid as a colourless solid. Yield: 96%. M.p.>250°. Mass spectrum (ISN) 322.2 (M±H, 100%).

13al) In analogy to Example 13a), from ethyl 6,7,8-trifluoro-4-oxo-1-phenyl-1,4-dihydro-quinoline-carboxylate (Liebigs Ann. Chem. 1987, 1,29–37) there is obtained 6,8-difluoro-7-hydroxy-4-oxo-1-phenyl-1,4-dihydro-quinoline-carboxylic acid as a colourless solid. Yield: 73%. M.p.>250°. Mass spectrum (ISN) 316.2 (M±H, 100%).

13am) In analogy to Example 13b), from 1-cyclohexyl-6,8-difluoro-7-hydroxy-4-oxo-1,4-dihydro-quinoline-carboxylic acid (Example 13ak)) there is obtained ethyl 1-cyclohexyl-6,8-difluoro-4-oxo-7-trifluoromethyl) sulphonyloxy-1,4-dihydro-quinoline-carboxylate as a colourless amorphous solid. Yield: 33%. Mass spectrum: peaks inter alia at 483 (M+, 8%), 411 (26%), 356 (23%), 329 (34%), 83 (75%), 55 (100%).

13an) In analogy to Example 13b), from 6,8-difluoro-7-hydroxy-4-oxo-1-phenyl-1,4-dihydro-quinoline-carboxylic acid (Example 13al)) there is obtained ethyl 6,8-difluoro-4-oxo-1-phenyl-7-trifluoromethyl)sulphonyloxy-1,4-dihydro-quinoline-carboxylate as a colourless amorphous solid. Yield: 64%. Mass spectrum: peaks inter alia at 477 (M+, 10%), 432 (9%), 405 (100%), 272 (36%).

13ao) 1.8 g of a 55 percent suspension of sodium hydride in oil is washed twice with pentane and suspended in 45 ml of THF. A solution of 3 g of 1,7-dihydroxynaphthalene in 45 ml of THF is slowly added dropwise and the mixture is held at reflux for 1 hr. Thereafter, a solution of 3.2 ml of chloromethyl methyl ether is added dropwise at room temperature and the mixture is heated at reflux for a further hour. The mixture is poured into 100 ml of ice-water and extracted three times with ether. After drying, evaporation and chromatography on silica gel with methylene chloride there are isolated 1.2 g of 1,7-bis-methoxymethoxy-naphthalene. Yield: 26%. Mass spectrum: peaks inter alia at 248 (M+, 42%), 188 (18%), 45 (100%).

1.2 g of 1,7-bis-methoxymethoxy-naphthalene are dissolved in 9 ml of THF and cooled to −78°. 3.13 ml of a 1.6M n-butyl-lithium solution in hexane are added dropwise thereto and the mixture is stirred at room temperature overnight. Subsequently, it is again cooled to −78° and a solution of 1.25 g of iodine in 3.4 ml of THF is added dropwise. The mixture is warmed to room temperature and 10 ml of saturated ammonium chloride solution are added. The organic solvents are evaporated on a rotary evaporator and the residue is extracted three times with ether. After drying and evaporation the residue is chromatographed on silica gel with ethylene chloride. 0.72 g of 8-iodo-1,7-bis-methoxy-naphthalene is thus isolated. Yield: 40%. Mass spectrum: peaks inter alia at 374 (M+, 87%), 171 (40%), 45 (100%).

13ap) 3.3 g of 5-bromoisatin, 0.8 g of hydroxylamine hydrochloride and 1.6 g of sodium acetate are held at reflux in 50 ml of water for 1.5 hrs. The yellow crystals are filtered off and dried. 2.11 g of 5-bromoisatin oxime are isolated. Yield: 83%. M.p.=215° (decomposition).

13aq) In analogy to Example 13ap), from N-benzyl-5-bromo-isatin (G.Tacconi et al., J. Prakt. Chem. 315, 339 (1973)) there is obtained the corresponding N-benzyl-5-bromo-isatin oxime as a yellow solid. Yield: 94%. Mass spectrum: peaks inter alia at 330 (M+, 17%); 285 (14%), 91 (100%). 13ar) 1.36 g of N-acetyl-3-iodo-aniline are dissolved in 25 ml of methylene chloride and treated with 61 mg of 4-dimethylamino-pyridine. A solution of 5.25 ml of cyclopropanecarbonyl chloride in 7 ml of methylene chloride is added dropwise to this solution. The mixture is stirred at room temperature overnight, then poured into 100 ml of water and made weakly acid with a few drops of dil. hydrochloric acid. Extraction with ethyl acetate and chromatography on silica gel with ethyl acetate gives 1.85 g of cyclopropanecarboxylic acid acetyl-(3-iodo-phenyl)-amide as a yellowish oil which solidifies in time. Yield: 92%. Mass spectrum: peaks inter alia at 329 (M+, 8%); 287 (58%), 69 (100%).

13as) In analogy to Example 13ap), from 3-iodo-4,5-dimethoxy-benzaldehyde and hydroxylamine hydrochloride there is obtained the corresponding 3-iodo-4,5-dimethoxy-benzaldehyde oxime as a colourless solid. Yield: 99%.

13at) 4.38 g of 3-iodoaniline, 1.06 g of acrylonitrile and 0.5 g of copper-(II)acetate are mixed and held at 70° for 5 hrs. The mixture is chromatographed on silica gel with ethyl acetate/cyclohexane 1:4 and yields 2.01 g of 3-(3-iodo-phenylamino)-propionitrile as a brown oil. Yield: 37%. Mass spectrum: peak inter alia at m/e : 272 (M+, 50%), 232 (100%); 105 (35%).

1.0 g of 3-(3-iodo-phenylamino)-propionitrile are dissolved in a mixture of 25 ml of methylene chloride and 0.45 ml of triethylamine and treated dropwise at 0° with a solution of 0.42 g of cyclopropanecarbonyl chloride in 5 ml of methylene chloride. The solution is stirred at room temperature for a further 2 hrs., then poured into ice-water and extracted three times with ethyl acetate. Concentration yields 1.19 g of crude cyclopropanecarboxylic acid (2-cyano-ethyl)-(3-iodo-phenyl)-amide which is used in Example 12av) without further purification. Yield: 95%.

13au) 1.0 g of ethyl 2-(4-bromo-2-chloro-benzoyl)-3-dimethyl-amino-acrylate (Example 13bk) and 0.283 g of tetrahydrofurfurylamine are stirred at room temperature in 20 ml of THF for 30 min. The mixture is concentrated and the residue is chromatographed on silica gel with ethyl acetate/hexane 7:3. 1.10 g of ethyl 2-(4-bromo-2-chloro-benzoyl)-3-[(tetrahydro-furan-2-ylmethyl)-amino]-acrylate are isolated as a colourless solid. Yield: 95%. M.p.=136°.

500 mg of ethyl 2-(4-bromo-2-chloro-benzoyl)-3-[(tetrahydro-furan-2-ylmethyl)-amino]- acrylate and 148 mg of potassium t-butylate are held at 60° in 20 ml of DMSO for 30 mins. After chromatography on silica gel with ethyl acetate/hexane 1:1 343 mg of ethyl 7-bromo-4-oxo-1-(tetrahydro-furan-2-ylmethyl)-1,4-dihydro-quinoline-3-carboxylate are isolated as a yellowish oil. Yield: 75%. Mass spectrum: peaks inter alia at m/e: 380 (M++H, 100%).

13av) In analogy to Example 13au), from ethyl 2-(4-bromo-2-chloro-benzoyl)-3-dimethylamino-acrylate and furfurylamine there is obtained ethyl 7-bromo-4-oxo-1-(furan-2-ylmethyl)-1,4-dihydro-quinoline-3-carboxylate as a colourless solid. Yields over the two steps: 80%. Mass spectrum: peaks inter alia at m/e: 378 and 376 (M+, 94 and 100%).

13ax) A mixture of 5.0 g of 3-iodo-4,5-dimethoxy-benzaldehyde, 1.18 g of hydroxylamine hydrochloride, 1.37 g of pyridine and 17 ml of toluene is held at reflux for 2 hrs. (see A. Saednya, Synthesis 1982, 190). The precipitate which separates after cooling is filtered off under suction. Chromatography on silica gel with methylene chloride/methanol 9:1 yields 3.09 g of 3-iodo-4,5-dimethoxy-benzonitrile as a colourless solid. Yield: 63%. Mass spectrum: peaks inter alia at m/e: 289 (100%), 274 (38%), 132 (30%), 119 (43%).

13ay) A mixture of 1.53 g of 3-iodoaniline, 2.02 g of triethylamine and 0.1 g of 4-dimethylaminopyridine in 25 ml of THF is treated dropwise with 1.83 g of cyclopropanecarbonyl chloride and subsequently held at reflux for 4 hrs. The mixture is poured into 50 ml of ice-water, made weakly acid (pH about 4) with dil. HCl and extracted three times with ethyl acetate. Chromatography on silica gel with petroleum ether/ethyl acetate 4:1 gives 1.73 g (69%) of crude cyclopropanecarboxylic acid cyclopropanecarbonyl-(3-iodo-phenyl)-amide as a colourless oil with solidifies after a few days. Yield: 69%.

13az) In analogy to Example 13au), from ethyl 2-(4-bromo-2-chloro-benzoyl)-3-dimethylamino-acrylate and tetrahydro-pyran-4-ylamine (T. P. Johnston, J. Med. Chem. 14, 611 (1971)) there is obtained ethyl 7-bromo-4-oxo-1-(tetrahydro-pyran-4-yl)-1,4-dihydro-quinoline-3-carboxylate as yellowish crystals. Yield over the two steps: 41%. Mass spectrum: peaks inter alia at m/e: 382.3 (83%) and 380.3 (M++H, 85%).

13ba) 272 mg of monomethyl malonate potassium salt and 0.41 ml of trimethylsilyl chloride are stirred at room temperature in 5 ml of acetonitrile for 4 hrs. Subsequently, the mixture is cooled to 0° and 0.75 ml of diazabicycloundecane is added. The mixture is stirred at room temperature for 30 min. Thereafter, 0.5 g of 3-iodo-4,5-dimethoxy-benzoyl chloride is added portionwise thereto and the mixture is stirred at room temperature for 19 hrs. The mixture is brought to about pH4 with 10 percent citric acid and extracted three times with ethyl acetate. Chromatography on silica gel with ethyl acetate/hexane 1:1 gives 126 mg of ethyl 3-(3-iodo-4,5-dimethoxy-phenyl)-3-oxo-propionate as a yellowish oil (Keto/Enol mixture). Yield: 26%. Mass spectrum: peaks inter alia at m/e: 378 (M+, 40%); 291 (100%).

13bb) 1.53 g of 3-iodoaniline and 2.78 ml of triethylamine are dissolved in 25 ml of methylene chloride and treated dropwise at room temperature with a solution of 1.6 ml of cyclopropane carbonyl chloride in 10 ml of methylene chloride. The mixture is stirred at room temperature for a further 5 hrs., evaporated and poured into 50 ml of water. The mixture is made slightly acid with dil. hydrochloric acid and extracted three times with ethyl acetate. The residue is recrystallized from toluene. 1.47 g of cyclopropanecarboxylic acid (3-iodo-phenyl)-amide are isolated as a colourless solid. Yield: 74%. M.p.=133°.

13bc) In analogy to Example 13ay), from 3-iodoaniline and furoyl chloride there is obtained furan-2-carboxylic acid (furan-2-carbonyl)-(3-iodo-phenyl)-amide as slightly pink coloured crystals. Yield: 58%. M.p.=112°.

13bd) A mixture of 2 g of 3-iodoaniline and 1.26 ml of tetrahydro-4H-pyran-4-one is boiled in 50 ml of toluene on a water separator for 4 hrs. The solution of the imine which remains behind is treated with 20 ml of methanol and 520 mg of sodium borohydride are added in portions. The mixture is stirred at room temperature for 16 hrs., then poured into water and extracted with ethyl acetate. Chromatography on silica gel with ethyl acetate/hexane 3:7 gives 559 mg of (3-iodo-phenyl)-(tetrahydropyran-4-yl)-amine as a colourless oil. Yield: 20%. Mass spectrum: peaks inter alia at m/e: 303 (M+, 100%), 245 (40%), 219 (40%), 130 (90%), 117 (62%).

13be) In analogy to Example 13bb), from 3-iodoaniline and furoyl chloride there is obtained furan-2-carboxylic acid (3-iodophenyl)-amide as a colourless solid. Yield: 95%. Mass spectrum: peaks inter alia at m/e: 313 (M+, 60%), 95 (100%).

13bf) 3.19 g of furan-2-carboxylic acid (3-iodo-phenyl)-amide (Example 13bf)) are dissolved in 25 ml of methylene chloride with 2.78 ml of triethylamine and 100 mg of 4-dimethylaminopyridine. 1.60 g of cyclopropanecarbonyl chloride are added thereto and the mixture is stirred at room temperature for 5 hrs. The mixture is concentrated, poured into water and extracted three times with ethyl acetate. Chromatography on silica gel with ethyl acetate/hexane 3:7 gives 1.56 g of cyclopropanecarboxylic acid (furan-2-carbonyl)-(3-iodo-phenyl)-amide as a colourless solid. Yield: 58%. Mass spectrum: peaks inter alia at m/e: 381 (20%), 353 (28%), 313 (86%), 95 (75%), 69 (100%).

13bg) in analogy to Example 13bb), from (3-iodo-phenyl)-(tetra-hydro-pyran-4-yl)-amine (Example 13bd)) and cyclopropanecarbonyl chloride there is obtained crude cyclopropanecarboxylic acid (3-iodo-phenyl)-(tetrahydro-pyran-4-yl)-amide as a colourless oil. Yield: 96%.

13bh) A mixture of 2.64 g of 2-hydroxy-5-iodo-benzoic acid, 0.69 g of cyclopropylamine and 3.65 g of carbon tetrabromide in 40 ml of methylene chloride is treated portionwise at room temperature with 2.62 g of triphenylphosphine. After 2 hrs. the mixture is filtered and the filtrate is concentrated. Chromatography on silica gel with ethyl acetate/cyclohexane 1:4 gives 550 mg of crude N-cyclopropyl-2-hydroxy-5-iodo-benzamide. Yield: 18%.

13bi) 1.15 g of 3-iodoaniline and 097 g of N-BOC-glycine are dissolved in 25 ml of methylene chloride and treated portionwise at 0° with 1.14 g of dicyclohexylcarbodiimide. The separated urea is filtered off and the filtrate is concentrated. Recrystallization from toluene yields tert.butyl [(3-iodo-phenyl-carbamoyl)-methyl]-carbamate as colourless crystals. Yield: 60%. M.p.=126°–128°.

13bj) 2 g of di-2-pyridyl-ketone and 1.51 g of hydroxylamine-hydrochloride are added to 13 ml of pyridine and the mixture is held at reflux for 4 hrs. After concentration and cooling there are isolated 2.95 g of crude di-2-pyridyl ketone oxime (contaminated with salts). Addition of 1.18 g of ammonium acetate, 44 ml of dil. ammonia, 30 ml of water and 30 ml of ethanol yields a suspension which is treated portionwise with 4.5 g of zinc powder. The mixture is held at reflux for 4 hrs., cooled and suction filtered. The filtrate is concentrated and the residue is triturated with methanol. 2.54 g of crude C,C-dipyridin-2-yl-methylamine are isolated. Yield: 93%.

1.5 g of C,C-dipyridin-2-yl-methylamine are suspended in 50 ml of methylene chloride and 1.15 ml of triethylamine and treated dropwise at 0° with a solution of 3-iodo-benzoyl chloride. After 1 hr. at 0° the reddish suspension is concentrated, the residue is poured into water and extracted three times with methylene chloride. Chromatography on silica gel with methylene chloride/methanol 9:1 yields 1.31 g of brownish N-(di-pyridin-2-yl-methyl)-3-iodo-benzamide. Yield: 39%. Mass spectrum: peaks inter alia at m/e: 415 (M+, 8%), 320 (44%), 231 (36%), 184 (100%).

13bk) 49.4 g of 4-bromo-2-chloro-benzoic acid were suspended in 60 ml of hexane, treated with 0.2 ml of N,N-dimethylformamide and 18.5 ml of thionyl chloride and boiled at reflux under argon for 15 hrs. The resulting solution was cooled to room temperature, filtered, evaporated and the residue was again evaporated with 60 ml of toluene. There were obtained 53 g (99%) of 4-bromo-2-chloro-benzoylchloride as a crude oil which crystallized upon standing, but which was used directly in the next step without further manipulation.

30.2 g of ethyl 3-dimethylaminoacrylate and 29.3 ml of triethylamine were dissolved in 180 ml of toluene and heated to reflux. At this temperature there was added dropwise thereto a solution of 53 g of 4-bromo-2-chloro-benzoyl chloride in 50 ml of toluene over 30 min. and the mixture was subsequently stirred at reflux for a further 1 hr. The mixture was left to cool to room temperature and was stirred in an ice bath for a further 30 min. The suspension was filtered and the triethylamine hydrochloride was washed with 40 ml of ice-cold toluene. The filtrate was concentrated to half of the volume and then, for crystallization, diluted with 100 ml of hexane and stirred in an ice bath for a further 1 hr. 51.2 g (67%) of ethyl 2-(4-bromo-2-chlorobenzoyl)-3-dimethylamino-acrylate were obtained as white crystals. M.p. 101°.

13bl) 3.6 g of ethyl 2-(4-bromo-2-chloro-benzoyl)-3-dimethylaminoacrylate (Example 13bk)) and 2-amino-2-methyl-1-propanol in 40 ml of 1,2-dichloroethane were stirred at room temperature for 1 hr. with the direct introduction of argon. Then, 0.74 ml of triethylamine, 1.66 g of tert.-butyldimethylchlorosilane and 1.22 mg of 4-dimethylaminopyridine were added and the mixture was stirred at room temperature for 24 hrs. The reaction mixture was chromatographed directly on silica gel in dichloromethane. 4.64 g (92%) of ethyl 2-(4-bromo-2-chloro-benzoyl)-3-[2-(tert.-butyl-dimethyl-silanyloxy)-1,1-dimethyl-ethylamino]-acrylate were obtained as a colourless oil. Mass spectrum (ISP): peaks inter alia at 520 (M+H, 100%), 518 (75%).

13bm) 4.3 g of ethyl 2-(4-bromo-2-chloro-benzoyl)-3-[2-(tert.-butyl-dimethyl-silanyloxy)-1,1-dimethyl-ethylamino]-acrylate (Example 13bl)) were dissolved in 40 ml of dimethyl sulphoxide under argon, treated with 1.1 g of potassium tert.-butylate and stirred for 15 min. Then, the mixture was stirred at 50° for 1.5 hrs. After cooling the mixture was diluted with 200 ml of water and the product was then extracted with two 200 ml portions of ethyl acetate, purified by silica gel chromatography in hexane/ethyl acetate 1:1 and crystallized from 30 ml of hexane/ethyl acetate 1:1. 2.45 g (62%) of ethyl 7-bromo-1-[2-(tert.-butyl-dimethyl-silanyloxy)-1,1-dimethyl-ethyl]-4-oxo-1,4-dihydro-quinoline-3-carboxylate were obtained as white crystals. M.p. 133° C.

13bn) 50 g of bromacetophenone in 500 ml of diethyl carbonate were treated portionwise with 20.8 g of sodium hydride dispersion (60% in oil) and the mixture was stirred at 80° for 2 hrs. Then, the mixture was poured into 1.5 l of ice-water and 75 ml of acetic acid and extracted with 1.5 l of ethyl acetate. The crude product was purified by distillation at 150°/0.2 Torr. 52 g (76%) of ethyl 3-(4-bromophenyl)-3-oxo-propionate were obtained as a yellowish oil.

13bo) 3.6 g of ethyl [E/Z]-2-(4-bromo-2-chloro-benzoyl)-3-dimethylaminoacrylate (Example 13bk)) and 1.8 g of D-glucamine were stirred for 15 min. at 50° C. with the direct introduction of argon. Then, 1.4 g of potassium tert.-butylate were added and the mixture was stirred at 50° for 2 hrs. and at 100° for a further 20 min. The viscous mass was diluted slowly with 40 ml of water and the precipitate was filtered off and washed with water. 2.26 g (49%) of (7S,8R,9R,10S,22S,23R,24R,25S)-3,18-dibromo-7,8,9,10,22,23,24,25-octahydro-5,6,7,8,9,10,20, 21,22,23,24,25,26-tetrahydro-5,29:14,20-dimethenodibenzo[b,o][7,20,1,14]dioxadiazacyclohexacosin-13,15,28,30-tetraone were obtained as a difficultly soluble beige powder.

1.3 g of this powder in 10 ml of pyridine and 10 ml of acetic anhydride were stirred with 192 mg of 4-dimethylaminopyridine at room temperature under argon for 19 hrs. Extraction: twice with 200 ml of ethyl acetate, twice with 100 ml of 1N HCl, once with 100 ml of water, once with 100 ml of sodium hydrogen carbonate solution. Chromatography: silica gel, dichloromethane/methanol 20:1. Crystallization: 10 ml of hot ethanol. 827 mg (45%) of (7S,8R,9R,10S,22S,23R,24R,25S)-7,8,9,10,22,23,24,25-octaacetoxy-3,18-dibromo-5,6,7,8,9,10,20,21,22,23,24,25, 26-tetrahydro-5,29:14,20-dimethenodibenzo[b,o][7,20,1, 14]dioxadiazacyclohexacosin-13,15,28,30-tetraone were obtained as white crystals. M.p. 208°.

13bp) 27.1 g of ethyl 3-(4-bromo-phenyl)-3-oxo-propionate in 70 ml of acetic acid were cooled in ice and treated dropwise with a solution of 8.3 g of sodium nitrite in 12 ml of water. Then, the mixture was stirred at room temperature for a further 2 hrs. and then diluted with 80 ml of water and cooled in ice for a further 1 hr. The precipitate was filtered off. 28.3 g (94%) of ethyl [E/Z]-3-(4-bromo-phenyl)-2-hydroxyimino-3-oxo-propionate were obtained as white crystals. M.p. 149°.

13bq) 600 mg of ethyl [E/Z]-3-(4-bromophenyl)-2-hydroxyimino-3-oxo-propionate (Example 13bp)), 787 mg of triphenylphosphine and 0.22 ml of ethylene glycol monomethyl ether in 6 ml of toluene were cooled in ice under argon and treated dropwise with 0.47 ml of diethyl azodicarboxylate. The mixture was stirred at room temperature for 15 hrs., evaporated and the residue was chromatographed on silica gel in hexane/ethyl acetate 5:1. 450 mg (66%) of ethyl [E/Z]-3-(4-bromophenyl)-2-(2-methoxyethoxyimino)-3-oxo-propionate were obtained as a colourless oil (not characterized further).

13br) 1.5 g of ethyl [E/Z]-3-(4-bromo-phenyl)-2-hydroxyimino-3-oxo-propionate (Example 13bp)), 0.67 ml of dimethyl sulphate and 1 g of sodium carbonate in 40 ml of acetone were boiled at reflux for 1.5 hrs., filtered and evaporated. The residue was chromatographed on silica gel in hexane/ethyl acetate 5:1. 560 mg (36%) of ethyl [E/Z]-3-(4-bromo-phenyl)-2-methoxyimino-3-oxo-propionate were obtained as a colourless oil. Mass spectrum (EI): peaks inter alia at 315/313 (M+, 1%), 185 (100%), 183 (85%), 155 (25%).

13bs) 6.8 g of monoethyl malonate potassium salt in 70 ml of acetonitrile were cooled to 10° under argon and treated with 5.3 ml of triethylamine and 4.8 g of magnesium chloride. The resulting thick suspension was stirred at room temperature for 2 hrs. Then, it was again cooled to 10° and 5 g of 4-bromo-2-chloro-benzoyl chloride were added dropwise thereto over 30 min. The mixture was stirred at room temperature for 15 hrs. and then concentrated. Extraction: twice with 100 ml of toluene, once with 100 ml of cold 1N HCl and twice with 100 ml of water. After drying and evaporation there were obtained 5.2 g (85%) of ethyl 3-(4-bromo-2-chlorophenyl)-3-oxo-propionate as a brown oil which crystallized in a refrigerator. M.p. 34° C.

13bt) In analogy to Example 13bp), with ethyl 3-(4-bromo-2-chlorophenyl)-3-oxo-propionate (Example 13bs)) there is obtained ethyl [E/Z]-3-(4-bromo-2-chlorophenyl)-2-hydroxyimino-3-oxo-propionate. Yield: 84%. M.p. 102°.

13bu) 1.1 g of ethyl [E/Z]-3-(4-bromo-2-chlorophenyl)-2-hydroxyimino-3-oxo-propionate (Example 13bt)), 1 g of triphenylchloromethane, 0.5 ml of triethylamine and 45 mg 4-dimethylaminopyridine in 12 ml of dichloromethane were stirred at room temperature under argon for 3 hrs. Extraction: 40 ml of dichloromethane, twice with 40 ml of water. Chromatography: silica gel, hexane/ethyl acetate 10:1. 1.25 g (64%) of ethyl [E/Z]-3-(4-bromo-2-chlorophenyl)-2-trityloxyimino-3-oxo-propionate as white crystals. M.p. 119°.

13bv) A solution of 34.4 g (200 mmol) of 4-bromoaniline in 300 ml of dichloromethane was cooled to 2° under argon and treated dropwise with a solution of 28.2 g (100 mmol) of trifluoromethanesulphonic anhydride at such a rate that the reaction temperature could be held at 4°. After completion of the addition the mixture was warmed to room temperature and was stirred at this temperature for one hour. Subsequently, the mixture was treated with 200 ml of 2N hydrochloric acid solution and the organic phase was separated. The latter was washed neutral with 100 ml of 2N hydrochloric acid solution and then twice with 200 ml of water each time. Drying over sodium sulphate and evaporation gave a solid crude product which was digested in pentane. There were obtained 18.69 g (61.5%) of N-(4-bromophenyl)-C,C,C-trifluoro-methanesulphonamide as a colourless powder of m.p. 52°–54°. A further 6.75 g (22%) of product could be obtained from the mother liquor.

13bw) A suspension of 1.52 g (5 mmol) of N-(4-bromophenyl)-C,C,C-trifluoro-methanesulphonamide (Example 13bv)), 1.56 g (10 mmol) of 4-methoxybenzyl chloride and 1.38 g (10 mmol) of powdered potassium carbonate in 15 ml of acetone was stirred at reflux for 18 hours. Thereafter, the mixture was concentrated and the residue was taken up in 100 ml of water and 100 ml of ethyl acetate, the organic phase was separated and the aqueous phase was extracted twice with 100 ml of ethyl acetate each time. The combined organic phases were washed neutral with sat. sodium chloride solution, dried over magnesium sulphate and evaporated. The resulting yellow oil was subjected to flash chromatography with hexane/ethyl acetate 95:5. 2.06 g (97%) of N-(4-bromophenyl)-C,C,C-trifluoro-N-(4-methoxy-benzyl)-methanesulphonamide were obtained as a colourless, viscous oil. MS (EI): 423 and 425 (M+, 3%), 121 ([CH$_2$—C$_6$H$_4$—OCH$_3$]$^+$, 100%).

13bx) A solution of 1.52 g (5 mmol) of N-(4-bromophenyl)-C,C,C-trifluoro-methanesulphonamide (Example 13bv)) in 25 ml of ethyl orthoformate was heated to reflux for 6 hours. Subsequently, the readily volatile constituents were distilled off on a water-jet vacuum and the residue was chromatographed over a flash column with hexane/ethyl acetate 95:5. There were obtained 1.55 g (93%) of N-(4-bromophenyl)-N-ethyl-C,C,C- trifluoro-methanesulphonamide as a pale yellow oil. MS (EI): 331 and 333 (M$^+$, 44%), 198 and 200 ([M-SO$_2$CF$_3$]$^+$, 80%), 118 ([M-(SO$_2$CF$_3$+HBr)]$^+$, 100%).

13by) A solution of 1.82 g (6 mmol) of N-(4-bromophenyl)-C,C,C-trifluoro-methanesulphonamide (Example 13bv)) in 30 ml of methyl orthoformate was heated to reflux for 23 hours. Subsequently, the readily volatile constituents were distilled off in a vacuum. 1.83 g (96%) of N-(4-bromophenyl)-N-methyl-C,C,C-trifluoro-methanesulphonamide remained behind as a colourless solid of m.p. 59°–60°.

13bz) In analogy to Example 13bw), from N-(4-bromophenyl)-C,C,C-trifluoro-methanesulphonamide (Example 13bv) and isobutyl iodide there was obtained N-(4-bromophenyl)-N-isobutyl-C,C,C-trifluoro-methanesulphonamide as a brown oil. Yield: 30%. MS (EI): 359 and 361 (M$^+$, 62%), 228 and 226 ([M-SO$_2$CF$_3$]$^+$, 41%), 184 ([M-(SO$_2$CF$_3$+C$_3$H$_7$)]$^+$, 100%).

13ca) In analogy to Example 13bw), from N-(4-bromophenyl)-C,C,C-trifluoro-methanesulphonamide (Example 13bv) and ethyl bromoacetate there was obtained [(4-bromophenyl)-(trifluoromethylsulphonyl)-amino]-acetate as a yellow oil. Yield: 67%. MS (EI): 389 and 391 (M$^+$, 56%), 183 and 185 ([Br—C$_6$H$_4$—NCH$_2$]$^+$, 100%).

13cb) In analogy to Example 13bv), from 3-bromoaniline and trifluoromethanesulphonic anhydride there was obtained N-(3-bromophenyl)-C,C,C-trifluoro-methansulphonamide. After recrystallization from pentane there was obtained a colourless crystalizate of m.p. 78°–79°. Yield: 67%.

13cc) In analogy to Example 13by), from N-(3-bromophenyl)-C,C,C-trifluoro-methanesulphonamide (Example 13cb)) and methyl orthoformate there was obtained N-(3-bromophenyl)-N-methyl-C,C,C-trifluoro-methanesulphonamide as a colourless oil. Yield: 81%. MS (EI): 317 and 319 (M+, 68%), 184 and 186 ([M—SO$_2$CF$_3$]$^+$, 100%).

13cd) In analogy to Example 13by), from N-(3-bromophenyl)-C,C,C-trifluoro-methansulphonamide (Example 13cb)) and ethyl orthoformate there was obtained N-(3-bromophenyl)-N-ethyl-C,C,C-trifluoro-methanesulphonamide as a yellowish oil. Yield: 83%. MS (EI): 331 and 333 (M+, 82%), 198 and 200 ([M—SO$_2$CF$_3$]$^+$, 82%), 118 ([M—(SO$_2$CF$_3$+HBr)]$^+$, 100%).

EXAMPLE 14

Preparation of ethynyl compounds IV

14a) A mixture of ethyl 1-ethyl-6-bromo-4-oxo-1,4-dihydro-quinoline-3-carboxylate (Example 13h)), 1.94 ml of ethynyltrimethylsilane, 70 mg of bis-trimethylphosphine-palladium dichloride and 2.5 mg of copper(I) iodide in 7 ml of triethylamine and 7 ml of dimethylformamide is stirred at 60° for 9 hrs. After cooling to room temperature the reaction mixture is treated with 100 ml of water and extracted twice with 50 ml of methylene chloride each time. The combined organic phases are washed twice with 250 ml of water each time and once with 250 ml of a saturated, aqueous sodium chloride solution and dried over magnesium sulphate. The crude product is chromatographed on aluminium oxide (neutral, grade III) with n-hexane/ethyl acetate 1:1. 1.27 g (80%) of ethyl 1-ethyl-6-trimethylsilyl-ethynyl-4-oxo-1,4-dihydro-quinoline-3-carboxylate are obtained.

A suspension of 1.26 g of ethyl 1-ethyl-6-trimethylsilyl-ethynyl-4-oxo-1,4-dihydro-quinoline-3-carboxylate in 5 ml of methanol is treated with 4 ml of a 1N aqueous potassium hydroxide solution at room temperature and stirred for 1 hr. The methanol is distilled off in a vacuum and the residue is treated with 50 ml of water. The suspension is extracted three times with 50 ml of methylene chloride each time. The combined organic phases are washed with 150 ml of saturated, aqueous sodium chloride solution and dried over magnesium sulphate. The crude product is triturated with 5 ml of methylene chloride, filtered off under suction and dried. 0.695 g (69%) of ethyl 1-ethyl-6-ethynyl-4-oxo-1,4-dihydro-quinoline-3-carboxylate is obtained as a beige solid. M.p. 185°–187°.

14b) In analogy to Example 14a), from ethyl 7-bromo-4-hydroxy-quinoline-3-carboxylate (J. Am. Chem. Soc. 71, 3226, (1949)) there is obtained ethyl 7-ethynyl-4-hydroxy-quinoline-3-carboxylate as a beige solid. Yield: 98%. Mass spectrum: peaks inter alia at 241 (M+, 42%), 195 (100%), 167 (14%).

14c) In analogy to Example 14a), from ethyl 7-bromo-1-methyl-4-oxo-1,4-dihydro-quinoline-3-carboxylate (Example 13e) there is obtained ethyl 7-ethynyl-1-methyl-4-oxo-1,4-dihydro-quinoline-3-carboxylate as a yellowish solid. Yield: 78%. M.p. 156°–158°.

14d) In analogy to Example 11a) and 11b), from ethyl 1-benzyl-7-bromo-4-oxo-1,4-dihydro-quinoline-3-carboxylate (Example 13f) there is obtained ethyl 1-benzyl-7-ethynyl-4-oxo-1,4-dihydro-quinoline-3-carboxylate as a yellowish solid. Yield: 97%. M.p. 181°–182°.

14e) 10 g of 6-bromo-2-naphthol, 13.4 g of imidazole and 15 g of t-butyldimethylchlorosilane were stirred at room temperature in 75 ml of dimethylformamide for 18 hrs. Thereafter, 500 ml of ether were added thereto and the organic phase was washed 5 times with 100 ml of water each time. The organic phases were concentrated and the residue was dried in a high vacuum. 15.0 g of 6-bromo-2-t-butyl-dimethylsilyloxy-naphthaline were isolated as a yellowish solid. Yield: 99%. Mass spectrum (ISP): peaks inter alia at m/e: 338 and 336 (M+, in each case 34%), 281 (100%), 279 (98%), 200 (98%).

In analogy to Example 14a), from this 6-bromo-2-t-butyl-dimethylsilyloxy-naphthaline there was obtained the corresponding 6-ethynyl-2-naphthol as a yellowish oil. Yield: 38%. Mass spectrum (ISP): peaks interalia at m/e: 168 (M+, 100%), 139 (38%).

14f) 2 g of 4-bromoacetophenone, 2.8 ml of ethynyltrimethylsilane, 140 mg of bis(triphenylphosphine) palladium dichloride, 3 ml of triethylamine and 14 mg of copper(I)iodide in 20 ml of N,N-dimethylformamide were stirred at 50° under argon for 2 hrs. After distillation of the solvent the residue was extracted once with 50 ml of ethyl acetate, once with 50 ml of 1N HCl and twice with 50 ml of water. The crude product was purified by silica gel chromatography in hexane/ethyl acetate 10:1 and distilled at 120°/0.1 Torr in a bulb-tube oven. 1.74 g (80%) were obtained as a colourless oil. This was dissolved in 17 ml of methanol, treated with 110 mg of potassium carbonate and stirred at room temperature for 1.5 hrs. After evaporation the product was extracted with 20 ml of ethyl acetate and 20 ml of water and then crystallized from 10 ml of hexane. 0.8 g (71%) of 1-(4-ethynyl-phenyl)-ethanone was obtained as white crystals. M.p. 71°.

EXAMPLE 15

Preparation of vinyl/ethynyl compounds of formula
I

15a) A mixture of 197 mg of 5-(3,4-dimethoxy-5-iodo-benzyl)pyrimidine-2,4-diamine, 155 mg of 2-ethynyl-naphthalene (Bull. Soc. Chim. Fr. [3], 7, 648, (1892)), 108 mg of potassium carbonate, 14 mg of triphenylphosphine and 5 mg of copper(I) iodide in 2 ml of dimethylformamide is heated at 100° for 4 hrs. The reaction mixture is cooled to room temperature, poured into 50 ml of water and extracted three times with 50 ml of methylene chloride each time. The organic phases are washed with 50 ml of water, dried over magnesium sulphate and concentrated. The crude product is recrystallized from ethyl acetate/n-hexane. 121 mg (58%) of 5-[3,4-dimethoxy-5-(naphthalen-2-ylethynyl)-benzyl]-pyrimidine-2,4-diamine are obtained as a yellowish solid. M.p. 152°–155°.

15b) In analogy to Example 15a), with 5-(3,4-dimethoxy-5-iodo-benzyl)-pyrimidine-2,4-diamine and phenyl-acetylene there is obtained 5-[3,4-dimethoxy-5-(phenylethynyl)-benzyl]-pyrimidine-2,4-diamine as a yellowish solid. Yield: 17%. M.p. 166°–168°.

15c) In analogy to Example 15a), with 5-(3,4-dimethoxy-5-iodo-benzyl)-pyrimidine-2,4-diamine and ethyl 1-ethyl-6-ethynyl-4-oxo-1,4-dihydro-quinoline-3-carboxylate there is obtained ethyl 1-ethyl-6-[5-(2,4-diamino-pyrimidin-5-ylmethyl)-2,3-di-methoxy-phenylethynyl]-4-oxo-1,4-dihydro-quinoline-3-carboxylate as a beige solid. Yield: 53%. Mass spectrum: peaks inter alia at 527 (M+, 100%), 512 (63%), 466 (96%).

15d) In analogy to Example 15a), with 5-(3,4-dimethoxy-5-iodo-benzyl)-pyrimidine-2,4-diamine and ethyl 7-ethynyl-4-hydroxy-quinoline-3-carboxylate (Example 5b)) there is obtained ethyl 7-[5-(2,4-diamino-pyrimidin-5-ylmethyl)-2,3-dimethoxy-phenylethynyl]-4-hydroxy-quinoline-3-carboxylate as a beige solid. Yield: 43%. M.p.>230°. Mass spectrum: peaks: inter alia at 499 (M+, 44%), 484 (11%), 453 (21%). The compound is in tautomeric equilibrium with the corresponding 4-oxo-1,4-dihydro-quinoline compound.

15e) In analogy to Example 15a), with 5-(3,4-dimethoxy-5-iodo-benzyl)-pyrimidine-2,4-diamine and ethyl 7-ethynyl-1-methyl-4-oxo-1,4-dihydro-quinoline-3-carboxylate (Example 14c)) there is obtained ethyl 7-[5-(2,4-diamino-pyrimidin-5-ylmethyl)-2,3-dimethoxy-phenylethynyl]-1-methyl-4-oxo-1,4-dihydro-quinoline-3-carboxylate as a beige solid. Yield: 28%. M.p.>2300. Mass spectrum (ISP): peaks inter alia at 514.5 (M++H, 100%).

15f) In analogy to Example 15a), with 5-(3,4-dimethoxy-5-iodo-benzyl)-pyrimidine-2,4-diamine and ethyl 1-benzyl-7-ethynyl-4-oxo-1,4-dihydro-quinoline-3-carboxylate (Example 14d)) there is obtained ethyl 1-benzyl-7-[5-(2,4-diamino-pyrimidin-5-yl-methyl)-2,3-dimethoxy-phenylethynyl]-1-methyl-4-oxo-1,4-dihydro-quinoline-3-carboxylate as a beige solid. Yield: 52%. M.p. 223°–225°.

15g) A mixture of 193 mg of 5-(3,4-dimethoxy-5-iodo-benzyl)-pyrimidine-2,4-diamine, 224 mg of ethyl 1-cyclopropyl-6,8-difluoro-7-vinyl-4-oxo-1,4-dihydro-quinoline-3-carboxylate (J. Heterocyclic Chem., 28, 1581 (1991)), 26 mg of triphenylphosphine, 0.084 ml of triethylamine and 11.2 mg of palladium acetate in 2 ml of dimethylformamide is heated at 100° for 5 hrs. The reaction mixture is cooled to room temperature, poured into 50 ml of water and extracted twice with 25 ml of ethyl acetate each time. The organic phases are washed twice with 25 ml of 2N aqueous hydrochloric acid each time. The hydrochloric acid phases are made basic with sodium bicarbonate and extracted three times with 25 ml of methylene chloride each time. The combined organic phases are washed with 25 ml of water, dried over magnesium sulphate and concentrated. The crude product is recrystallized from methylene chloride/ diethyl ether. 140 mg (49%) of ethyl (E)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylate are obtained as a yellowish solid. Mass spectrum (ISP): 578 (M++H, 100%).

15h) In analogy to Example 15g), with 5-(3,4-dimethoxy-5-iodo-benzyl)-pyrimidine-2,4-diamine and ethyl 1-cyclopropyl-6-fluoro-7-vinyl-4-oxo-1,4-dihydro-quinoline-3-carboxylate (J. Heterocyclic Chem., 28, 1581 (1991)) there is obtained ethyl (E)-7-[2-[5-(2,4-diamino-pyrimidin-5-ylmethyl)-2,3-dimethoxy-phenyl]-vinyl]-1-cyclopropyl-6-fluoro-4-oxo-1,4-dihydro-quinoline-3-carboxylate as a yellowish solid. Yield: 42%. Mass spectrum (FAB): 550.6 (M++H, 100%).

15i) In analogy to Example 15g), with 5-(3,4-dimethoxy-5-iodo-benzyl)-pyrimidin-2,4-diamine and 1-cyclohexyl-4-oxo-7-vinyl-1,4-dihydro-quinoline-3-carboxylate (Example 13aj)) there is obtained ethyl (E)-1-cyclohexyl-7-[2-[5-(2,4-diamino-pyrimidin-5-ylmethyl)-2,3-dimethoxy-phenyl]-vinyl]-4-oxo-1,4-dihydro-quinoline-3-carboxylate as a beige amorphous solid. Yield: 45%. Mass spectrum (FAB): peaks inter alia at 584 (M++H, 100%), 558 (2%), 519 (3%), 503 (4%).

15j) In analogy to Example 15a), from 6-ethynyl-2-naphthol (Example 14e) there is obtained 6-[5-(2,4-diaminopyrimidin-5-ylmethyl)-2,3-dimethoxy-phenylethynyl]-naphthalen-2-ol as a brownish solid. Yield: 29%. Mass spectrum (ISP): peaks inter alia at m/e: 427 (M++H, 100%).

EXAMPLE 16

Conversion of vinyl/ethynyl compounds of formula I

16a) A suspension of 250 mg of ethyl 1-cyclopropyl-7-[5-(2,4-diamino-pyrimidin-5-ylmethyl)-2,3-dimethoxy-phenylethynyl]-6,8-difluoro-4-oxo-1,4-dihydro-quinoline-3-carboxylate (Example 12a)) and 50 mg of 5% palladium-on-charcoal in 50 ml of methanol is hydrogenated at normal hydrogen pressure. The reaction mixture is filtered after 6 hrs. The filtrate is concentrated and the crude product is triturated in succession with 20 ml and 10 ml of ethyl acetate and filtered off under suction. 133 mg (53%) of ethyl (Z)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylate are obtained as a colourless solid. M.p.>220°. Mass spectrum: peaks: inter alia at 577 (M+, 100%), 562 (35%), 530 (28%), 516 (68%), 474 (45%).

16b) A suspension of 342 mg of ethyl 1-cyclopropyl-7-[5-(2,4-diamino-pyrimidin-5-ylmethyl)-2,3-dimethoxy-phenylethynyl]-6,8-difluoro-4-oxo-1,4-dihydro-quinoline-3-carboxylate (Example 12a)) and 70 mg of 10% palladium-on-charcoal in 35 ml of dimethylformamide and 35 ml of acetic acid is hydrogenated at normal hydrogen pressure. After 6 hrs. the reaction mixture is filtered and the filtrate is concentrated in a high vacuum at 50°. The yellow residue is treated with 100 ml of 1N aqueous sodium hydroxide solution and extracted three times with 50 ml of methylene chloride each time. The combined organic phases are washed with 50 ml of water, dried over magnesium sulphate and concentrated. The crude product is triturated with 10 ml of hot ethyl acetate and filtered off under suction. 275 mg (80%) of ethyl 1-cyclopropyl-7-[2-[5-(2,4-diamino-pyrimidin-5-yl-methyl)-2,3-dimethoxy-phenyl]ethyl]-6,8-difluoro-4-oxo-1,4-dihydro-quinoline-3-carboxylate are obtained as a yellowish solid. M.p. 218°–220°.

16c) 0.51 g of ethyl 1-cyclopropyl-7-[5-(2,4-diamino-pyrimidin-5ylmethyl)-2,3-dimethoxy-phenylethynyl]-6,8-difluoro-1,4-dihydro-4-oxo-quinoline-3-carboxylate (Example 12a)) is held at reflux in 7 ml of ethanol and 7 ml of a 2N aqueous sodium hydroxide solution for one hour. The reaction mixture is cooled to room temperature and acidified with 25% aqueous hydrochloric acid. The precipitated substance is filtered off under suction, washed with 20 ml of water, 20 ml of ethanol and 20 ml of ether and dried. 444 mg (86%) of 1-cyclopropyl-7-[5-(2,4-diamino-pyrimidin-5ylmethyl)-2,3-dimethoxy-phenylethynyl]-6,8-difluoro-1,4-dihydro-4-oxo-quinoline-3-carboxylic acid hydrochloride are obtained as a colourless solid. M.p.>230°. Mass spectrum (ISP): peaks: inter alia at 548.5 (M++H, 100%).

16d) In analogy to Example 16c), with ethyl (Z)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylate (Example 16a)) there is obtained (Z)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylic acid hydrochloride as a colourless solid. M.p.>230°. Yield: 42%. Mass spectrum (ISP): peaks inter alia at 549 (M+, 14%), 505 (100%), 490 (56%), 450 (21%), 123 (58%).

16e) In analogy to Example 16c), with ethyl 1-cyclopropyl-7-[5-(2,4-diamino-pyrimidin-5-ylmethyl)-2,3-dimethoxy-phenylethynyl]-6-fluoro-4-oxo-1,4-dihydro-quinoline-3-carboxylate (Example 12b)) there is obtained 1-cyclopropyl-7-[5-(2,4-diamino-pyrimidin-5-ylmethyl)-2,3-dimethoxy-phenylethynyl]-6-fluoro-4-oxo-1,4-dihydro-quinoline-3-carboxylic acid trifluoroacetate as a colourless solid. Yield: 54%. M.p.>230°. Mass spectrum (ISP): peaks inter alia at 530 (M++H, 100%).

16f) In analogy to Example 16c), with ethyl 1-ethyl-7-[5-(2,4-diamino-pyrimidin-5-ylmethyl)-2,3-dimethoxy-phenylethynyl]-6-fluoro-4-oxo-1,4-dihydro-quinoline-3-carboxylate (Example 12c) there is obtained 1-ethyl-7-[5-(2,4-diamino-pyrimidin-5-ylmethyl)-2,3-dimethoxy-phenylethynyl]-6-fluoro-4-oxo-1,4-dihydro-quinoline-3-carboxylic acid hydrochloride as a colourless solid. Yield: 38%. M.p.>230°. Mass spectrum (ISP): peaks inter alia at 546.5 (M++H, 100%).

16 g) In analogy to Example 16c), with methyl 6-[5-(2,4-diamino-pyrimidin-5-ylmethyl)-2,3-dimethoxy-phenylethynyl]-nicotinate (Example 12d)) there is obtained 6-[5-(2,4-diamino-pyrimidin-5-ylmethyl)-2,3-dimethoxy-phenylethynyl]-nicotinic acid hydrochloride. Yield: 31%. M.p.>211° (dec.). Mass spectrum (ISP): peaks inter alia at 406 (M++H, 100%).

16h) In analogy to Example 16c), with ethyl 1-ethyl-7-[5-(2,4-diamino-pyrimidin-5-ylmethyl)-2,3-dimethoxy-phenylethynyl]-4-oxo-1,4-dihydro-quinoline-3-carboxylate (Example 12 g)) there is obtained 1-ethyl-7[5-(2,4-diamino-pyrimidin-5-ylmethyl)-2,3-dimethoxy-phenylethynyl]-4-oxo-1,4-dihydro-quinoline-3-carboxylic acid hydrochloride as a pale beige solid. Yield: 60%. M.p.>230°. Mass spectrum (ISP): peaks inter alia at 500 (M++H, 100%).

16i) In analogy to Example 16c), with ethyl (E)-7-[2-[5-(2,4-diamino-pyrimidin-5-ylmethyl)-2,3-dimethoxyphenyl]-vinyl]-1-cyclopropyl-6-fluoro-4-oxo-1,4-dihydro-quinoline-3-carboxylate (Example 15h)) there is obtained (E)-7-[2-[5-(2,4-diamino-pyrimidin-5-ylmethyl)-2,3-dimethoxy-phenyl]-vinyl]-1-cyclopropyl-6-fluoro-4-oxo-1,4-dihydro-quinoline-3-carboxylic acid as a yellowish solid. Yield: 39%. M.p.>230°. Mass spectrum (ISP): peaks inter alia at 530.3 (M±H, 100%).

16j) In analogy to Example 16c), with ethyl 6-[5-(2,4-diamino-pyrimidin-5-ylmethyl)-2,3-dimethoxy-phenylethynyl]-naphthalene-2-carboxylate (Example 12e)) there is obtained 6-[5-(2,4-diamino-pyrimidin-5-ylmethyl)-2,3-dimethoxy-phenylethynyl]-naphthalene-2-carboxylic acid hydrochloride as a beige solid. Yield: 88%. M.p.>230°. Mass spectrum (ISP): peaks inter alia at 455.4 (M++H, 100%).

16k) In analogy to Example 16c), with ethyl 1-ethyl-6-[5-(2,4-diamino-pyrimidin-5-ylmethyl)-2,3-dimethoxy-phenylethynyl]-4-oxo-1,4-dihydro-quinoline-3-carboxylate (Example 15c)) there is obtained 1-ethyl-6-[5-(2,4-diamino-pyrimidin-5-ylmethyl)-2,3-dimethoxy-phenylethynyl]-4-oxo-1,4-dihydro-quinoline-3-carboxylic acid hydrochloride as a beige solid. Yield: 93%. Mass spectrum (ISP): peaks inter alia at 500.4 (M++H, 100%).

16l) In analogy to Example 16c), with ethyl 7-[5-(2,4-diamino-pyrimidin-5-ylmethyl)-2,3-dimethoxy-phenylethynyl]-4-hydroxy-quinoline-3-carboxylate (Example 15d)) there is obtained 7-[5-(2,4-diamino-pyrimidin-5-ylmethyl)-2,3-dimethoxy-phenylethynyl]-4-hydroxy-quinoline-3-carboxylic acid hydrochloride as a yellowish solid. Yield: 94%. Mass spectrum (ISP): peaks inter alia at 472.4 (M++H, 100%).

16m) In analogy to Example 16c), with ethyl 7-[5-(Z,4-diamino-pyrimidin-5-ylmethyl)-2,3-dimethoxy-phenylethynyl]-1-methyl-4-oxo-1,4-dihydro-quinoline-3-carboxylate (Example 15e)) there is obtained 7-[5-(2,4-diamino-pyrimidin-5-ylmethyl)-2,3-dimethoxy-phenylethynyl]-1-methyl-4-oxo-1,4-dihydro-quinoline-3-carboxylic acid hydrochloride as a beige solid. Yield: 52%. Mass spectrum (ISP): peaks inter alia at 486 (M++H, 100%).

16n) In analogy to Example 16c), with methyl 4-[5-(2,4-diamino-pyrimidin-5-ylmethyl)-2,3-dimethoxy-phenylethynyl]-2-hydroxy-benzoate (Example 12f)) there is obtained 4-[5-(2,4-diamino-pyrimidin-5-ylmethyl)-2,3-dimethoxy-phenylethynyl]-2-hydroxy-benzoic acid hydrochloride as a colourless solid. Yield: 40%. Mass spectrum (ISP): peaks inter alia at 421 (M++H, 100%).

16o) In analogy to Example 16c), with ethyl 1-cyclopropyl-7-[2-[5-(2,4-diamino-pyrimidin-5-ylmethyl)-2,3-dimethoxy-phenyl]ethyl]-6,8-difluoro-4-oxo-1,4-dihydro-quinoline-3-carboxylate (Example 16b) there is obtained 1-cyclopropyl-7-[2-[5-(2,4-diamino-pyrimidin-5-ylmethyl)-2,3-dimethoxy-phenyl]ethyl]-6,8-difluoro-4-oxo-1,4-dihydro-quinoline-3-carboxylic acid hydrochloride as a colourless solid. Yield: 72%. Mass spectrum (ISP): peaks inter alia at 552.3 (M++H, 100%).

16p) In analogy to Example 16c), with ethyl 1-benzyl-7-[5-(2,4-diamino-pyrimidin-5-ylmethyl)-2,3-dimethoxy-phenylethynyl]-1-methyl-4-oxo-1,4-dihydro-quinoline-3-carboxylate (Example 15f)) there is obtained 1-benzyl-7-[5-(2,4-diamino-pyrimidin-5-ylmethyl)-2,3-dimethoxy-phenylethynyl]-1-methyl-4-oxo-1,4-dihydro-quinoline-3-carboxylic acid hydrochloride as a yellowish solid. Yield: 92%. Mass spectrum (ISP): peaks inter alia at 562.4 (M++H, 100%).

16q) In analogy to Example 16c), with ethyl (E)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylate (Example 15g)) there is obtained (E)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylic acid hydrochloride as a yellowish solid. Yield: 77%. Mass spectrum (ISP): peaks inter alia at 550.3 (M++H, 100%).

16r) In analogy to Example 16c), from ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate (Example 12h)) there is obtained 1-cyclohexyl-7-[5-(2,4-diamino-pyrimidin-5-ylmethyl)-2,3-dimethoxy-phenylethynyl]-4-oxo-1,4-dihydro-quinoline-3-carboxylic acid hydrochloride as a beige solid. Yield: 94%. M.p.>230°. Mass spectrum (ISP): peaks inter alia at 554.4 (M++H, 100%).

16s) In analogy to Example 16c), from ethyl 7-[5-(2,4-diamino-pyrimidin-5-ylmethyl)-2,3-dimethoxy-phenylethynyl]-4-oxo-1-propyl-1,4-dihydro-quinoline-3-carboxylate (Example 12i)) there is obtained 7-[5-(2,4-diamino-pyrimidin-5-ylmethyl)-2,3-dimethoxy-phenylethynyl]-4-oxo-1-propyl-1,4-dihydro-quinoline-3-carboxylic acid hydrochloride as a beige solid. Yield: 88%. M.p.>230°. Mass spectrum (ISP): peaks inter alia at 514.4 (M++H, 100%).

16t) In analogy to Example 16c), from ethyl 1-cyclopropylmethyl-7-[5-(2,4-diamino-pyrimidin-5-ylmethyl)-2,3-dimethoxy-phenylethynyl]-4-oxo-1-propyl-1,4-dihydro-quinoline-3-carboxylate (Example 12j)) there is obtained 1-cyclopropylmethyl-7-[5-(2,4-diamino-pyrimidin-5-ylmethyl)-2,3-dimethoxy-phenylethynyl]-4-oxo-1-propyl-1,4-dihydro-quinoline-3-carboxylic acid hydrochloride as a beige solid. Yield: 98%. M.p.>230°. Mass spectrum (ISP): peaks inter alia at 526.3 (M++H, 100%).

16u) In analogy to Example 16c), from ethyl 1-7-[5-(2,4-diamino-pyrimidin-5-ylmethyl)-2,3-dimethoxy-phenylethynyl]-1-(2-hydroxy-ethyl)-4-oxo-1,4-dihydro-quinoline-3-carboxylate (Example 12k)) there is obtained 1-7-[5-(2,4-diamino-pyrimidin-5-ylmethyl)-2,3-dimethoxy-phenylethynyl]-1-(2-hydroxy-ethyl)-4-oxo-1,4-dihydro-quinoline-3-carboxylic acid hydrochloride as a beige solid. Yield: 82%. M.p.>230°. Mass spectrum (ISP): peaks inter alia at 516.1 (M++H, 100%).

16v) In analogy to Example 16c), from ethyl 7-[5-(2,4-diamino-pyrimidin-5-ylmethyl)-2,3-dimethoxy-phenylethynyl]-1-{2-[2-(2-hydroxy-ethoxy)-ethoxy]-ethyl}-4-oxo-1,4-dihydro-quinoline-3-carboxylate (Example 12l)) there is obtained 7-[5-(2,4-diamino-pyrimidin-5-ylmethyl)-2,3-dimethoxy-phenylethynyl]-1-{2-[2-(2-hydroxy-ethoxy)-ethoxy]-ethyl}-4-oxo-1,4-dihydro-quinoline-3-carboxylic acid hydrochloride as a yellowish solid. Yield: 76%. M.p.>153° (dec.). Mass spectrum (FAB): peaks inter alia at 604 (M++H, 100%).

16w) In analogy to Example 16c), from ethyl 7-[5-(2,4-diamino-pyrimidin-5-ylmethyl)-2,3-dimethoxy-phenylethynyl]-4-oxo-1-pyridin-4-ylmethyl-1,4-dihydro-quinoline-3-carboxylate (Example 12m)) there is obtained 7-[5-(2,4-diamino-pyrimidin-5-ylmethyl)-2,3-dimethoxy-phenylethynyl]-4-oxo-1-pyridin-4-ylmethyl-1,4-dihydro-quinoline-3-carboxylic acid dihydro-chloride as a colourless solid. Yield: 77%. M.p.>230°. Mass spectrum (FAB): 563 (M++H, 100%).

16x) In analogy to Example 16c), from ethyl 7-[5-(2,4-diamino-pyrimidin-5-ylmethyl)-2,3-dimethoxy-phenylethynyl]-1-ethyl-4-oxo-1,4-dihydro-[1,8]

naphthyridine-3-carboxylate (Example 12n)) there is obtained 7-[5-(2,4-diamino-pyrimidin-5-ylmethyl)-2,3-dimethoxy-phenylethynyl]-1-ethyl-4-oxo-1,4-dihydro-[1,8]naphthyridine-3-carboxylic acid hydrochloride as a yellowish solid. Yield: 86%. M.p.>230°. Mass spectrum (FAB): 501 (M++H, 100%).

16y) In analogy to Example 16c), from ethyl 1-cyclopentyl-7-[5-(2,4-diamino-pyrimidin-5-ylmethyl)-2,3-dimethoxy-phenylethynyl]-4-oxo-1,4-dihydro-quinoline-3-carboxylate (Example 12o)) there is obtained 1-cyclopentyl-7-[5-(2,4-diamino-pyrimidin-5-ylmethyl)-2,3-dimethoxy-phenylethynyl]-4-oxo-1,4-dihydro-quinoline-3-carboxylic acid hydrochloride as a beige solid. Yield: 83%. M.p.>230°. Mass spectrum (FAB): 540 (M++H, 100%).

16z) In analogy to Example 16c), from ethyl 1-adamantan-1-yl-7-[5-(2,4-diamino-pyrimidin-5-ylmethyl)-2,3-dimethoxy-phenylethynyl]-4-oxo-1,4-dihydro-quinoline-3-carboxylate (Example 12p)) there is obtained 1-adamantan-1-yl-7-[5-(2,4-diamino-pyrimidin-5-ylmethyl)-2,3-dimethoxy-phenylethynyl]-4-oxo-1,4-dihydro-quinoline-3-carboxylic acid hydrochloride as a beige solid. Yield: 82%. M.p.>230° (dec). Mass spectrum (ISP): Spitzen u.a. 606.3(M++H, 100).

16aa) In analogy to Example 16c), from ethyl ( )-1-bicyclo[2.2.1]hept-2-yl-7-[5-(2,4-diamino-pyrimidin-5-ylmethyl)-2,3-dimethoxy-phenylethynyl]- 4-oxo-1,4-dihydro-quinoline-3-carboxylate (Example 12q)) there is obtained ( )-1-bicyclo-[2.2.1]hept-2-yl-7-[5-(2,4-diamino-pyrimidin-5-ylmethyl)-2,3-dimethoxy-phenylethynyl]-4-oxo-1,4-dihydro-quinoline-3-carboxylic acid hydrochloride as a beige solid. Yield: 60%. M.p.>230°. Mass spectrum (ISP): peaks inter alia at 566.0 (M++H, 100%).

16ab) In analogy to Example 16c), from ethyl 7-[5-(2,4-diamino-pyrimidin-5-ylmethyl)-2,3-dimethoxy-phenylethynyl]-4-oxo-(1,1,3,3-tetramethyl-butyl)-1,4-dihydro-quinoline-3-carboxylate (Example 12r)) there is obtained 7-[5-(2,4-diamino-pyrimidin-5-ylmethyl)-2,3-dimethoxy-phenylethynyl]-4-oxo-(1,1,3,3-tetra-methyl-butyl)-1,4-dihydro-quinoline-3-carboxylic acid hydrochloride as a colourless solid. Yield: 69%. Mass spectrum: peaks inter alia at 584 (M++H, 19%), 522 (5%), 472 (100%).

16ac) In analogy to Example 16c), from ethyl 1-tert-butyl-7-[5-(2,4-diamino-pyrimidin-5-ylmethyl)-2,3-dimethoxy-phenylethynyl]-4-oxo-1,4-dihydro-quinoline-3-carboxylate (Example 12s)) there is obtained 1-tert-butyl-7-[5-(2,4-diamino-pyrimidin-5-ylmethyl)-2,3-dimethoxy-phenylethynyl]-4-oxo-1,4-dihydro-quinoline-3-carboxylate hydrochloride as a beige solid. Yield: 82%. M.p.>211° (dec.). Mass spectrum (ISP): peaks inter alia at 528.5 (M++H, 100%), 472.4 (48%).

16ad) A suspension of 0.415 g of ethyl 1-(trans-4-tert-butoxycarbonylamino-cyclohexyl)-7-[5-(2,4-diamino-pyrimidin-5-ylmethyl)-2,3-dimethoxy-phenylethynyl]-4-oxo-1,4-dihydro-quinoline-3-carboxylate (Example 12t)) in 4 ml of methylene chloride and 0.4 ml of anisole is treated at 0° C. under argon with 1.9 ml of trifluoroacetic acid. The reaction mixture is warmed to room temperature and is stirred at room temperature for 4 hrs. After cooling with ice the reaction mixture is treated with 10 ml of diethyl ether. The separated crystals are filtered off under suction, washed with diethyl ether and dried. The crude product is dissolved in 50 ml of water, the resulting suspension is filtered and the filtrate is lyophilized. 0.39 g (92%) of ethyl 1-(trans-4-amino-cyclohexyl)-7-[5-(2,4-diamino-pyrimidin-5-ylmethyl)-2,3-dimethoxy-phenylethynyl]-4-oxo-1,4-dihydro-quinoline-3-carboxylate is obtained as a beige amorphous solid. Mass spectrum (FAB): peaks inter alia at 597 (M++H, 100%), 500 (90%), 454 (92%).

16ae) In analogy to Example 16c), from ethyl 1-(trans-4-amino-cyclohexyl)-7-[5-(2,4-diamino-pyrimidin-5-ylmethyl)-2,3-dimethoxy-phenylethynyl]-4-oxo-1,4-dihydro-quinoline-3-carboxylate trifluoroacetate (Example 16ad)) there is obtained 1-(trans-4-amino-cyclohexyl)-7-[5-(2,4-diamino-pyrimidin-5-ylmethyl)-2,3-dimethoxy-phenylethynyl]-4-oxo-1,4-dihydro-quinoline-3-carboxylic acid dihydrochloride as a yellowish solid. Yield: 53%. M.p.>230°. Mass spectrum: peaks inter alia at 569 (M++H, 37%), 472 (44%), 454 (100%).

16af) In analogy to Example 16c), from ethyl 7-[5-(2,4-diamino-pyrimidin-5-ylmethyl)-2,3-dimethoxy-phenylethynyl]-4-oxo-1-piperidin-4-ylmethyl-1,4-dihydro-quinoline-3-carboxylate (Example 12u)) there is obtained 7-[5-(2,4-diamino-pyrimidin-5-ylmethyl)-2,3-dimethoxy-phenylethynyl]-4-oxo-1-piperidin-4-ylmethyl-1,4-dihydro-quinoline-3-carboxylic acid hydrochloride as a yellowish solid. Yield: 83%. M.p.>230°. Mass spectrum (FAB): peaks inter alia at 569 (M++H, 100%).

16ag) In analogy to Example 16c), from ethyl 1-cyclopropyl-7-[5-(2,4-diamino-pyrimidin-5-ylmethyl)-2,3-dimethoxy-phenylethynyl]-4-oxo-1,4-dihydro-quinoline-3-carboxylate (Example 12v)) there is obtained 1-cyclopropyl-7-[5-2,4-diamino-pyrimidin-5-ylmethyl)-2,3-dimethoxy-phenylethynyl]-4-oxo-1,4-dihydro-quinoline-3-carboxylic acid hydrochloride as a beige solid. Yield: 96%. M.p.>230°. Mass spectrum (ISP): 512.1 (M++H, 100%).

16ah) In analogy to Example 16c), from ethyl 7-[5-(2,4-diamino-pyrimidin-5-ylmethyl)-2,3-dimethoxy-phenylethynyl]-4-oxo-1-(2,2,2-trifluoro-ethyl)-1,4-dihydro-quinoline-3-carboxylate (Example 12w)) there is obtained 7-[5-(2,4-diamino-pyrimidin- 5-ylmethyl)-2,3-dimethoxy-phenylethynyl]-4-oxo-1-(2,2,2-trifluoro-ethyl)-1,4-dihydro-quinoline-3-carboxylic acid hydrochloride as a yellowish solid. Yield: 76%. M.p.>222° (dec.). Mass spectrum (ISP): 554.3 (M++H, 100%).

16ai) In analogy to Example 16c), from ethyl 7-[5-(2,4-diamino-pyrimidin-5-ylmethyl)-2,3-dimethoxy-phenylethynyl]-4-oxo-1-phenyl-1,4-dihydro-quinoline-3-carboxylate (Example 12x)) there is obtained 7-[5-(2,4-diamino-pyrimidin-5-ylmethyl)-2,3-dimethoxy-phenylethynyl]-4-oxo-1-phenyl-1,4-dihydro-quinoline-3-carboxylic acid hydrochloride as a beige solid. Yield: 74%. M.p.>221° (dec.) Mass spectrum (ISP): 548.4 (M++H, 100%).

16aj) A suspension of 0.2 g of 1-ethyl-7-[5-(2,4-diamino-pyrimidin-5-ylmethyl)-2,3-dimethoxy-phenylethynyl]-4-oxo-1,4-dihydro-quinoline-3-carboxylic acid (3-dimethylamino-propyl)-amide (Example 12z)) in 50 ml-of water is treated with a 0.1N aqueous methanesulphonic acid solution, with a slightly turbid solution being obtained. This solution is filtered and the filtrate is lyophilized. 1-ethyl-7-[5-(2,4-diamino-pyrimidin-5-yl-methyl)-2,3-dimethoxy-phenylethynyl]-4-oxo-1,4-dihydro-quinoline-3-carboxylic acid (3-dimethylamino-propyl)-amide dimethanesulphonate are obtained as a yellowish amorphous solid. Mass spectrum (FAB): 584 (M++H).

16ak) In analogy to Example 16aj), from 2-dimethylamino-ethyl 1-ethyl-7-[5-(2,4-diamino-pyrimidin-5-ylmethyl)-2,3-dimethoxy-phenylethynyl]-4-oxo-1,4-dihydro-quinoline-3-carboxylate (Example 12ab)) there is obtained 2-dimethylamino-ethyl 1-ethyl-7-[5-(2,4- diamino-pyrimidin-5-ylmethyl)-2,3-dimethoxy-phenylethynyl]-4-oxo-1,4-dihydro-quinoline-3-carboxylate trimethanesulphonate as a pale yellowish amorphous solid. Yield: 99%. Mass spectrum (FAB): peaks inter alia at 571 (M++H, 8%), 500(100%).

16al) In analogy to Example 16aj), from 2-diisopropylamino-ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate (Example 12ac)) there is obtained 2-diisopropylamino-ethyl 1-cyclohexyl-7-[5-(2,4-diamino-pyrimidin-5-yl-methyl)-2,3-dimethoxy-phenylethynyl]-4-oxo-1,4-dihydro-quinoline-3-carboxylate methanesulphonate as a colourless solid. Yield: 95%. M.p.>139° (dec.). Mass spectrum (FAB): peaks inter alia at 681 (M++H, 7%), 554(58%), 341 (100%).

16am) In analogy to Example 16aj), from 2-morpholin-4-yl-ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate (Example 12ad) there is obtained 2-morpholin-4-yl-ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate dimethanesulphonate as a yellowish solid. Yield: 98%. M.p.>124° (dec.). Mass spectrum: (ISP) peaks inter alia at 667.2 (M++H, 28%), 554.2 (41%), 536.3 (31%), 334.5 (100%).

16an) In analogy to Example 16c), from ethyl 1-cyclohexyl-7-[5-(2,4-diamino-pyrimidin-5-ylmethyl)-2,3-dimethoxy-phenylethynyl]-8-methoxy-4-oxo-1,4-dihydro-quinoline-3-carboxylate (Example 12ae)) there is obtained 1-cyclohexyl-7-[5-(2,4-diamino-pyrimidin-5-ylmethyl)-2,3-dimethoxy-phenylethynyl]-8-methoxy-4-oxo-1,4-dihydro-quinoline-3-carboxylic acid hydrochloride as a colourless solid. Yield: 92%. M.p.>194° (dec.). Mass spectrum (FAB): peaks inter alia at 584(M++H, 100%).

16ao) In analogy to Example 16c), from ethyl (E)-1-cyclohexyl-7-[2-[5-(2,4-diamino-pyrimidin-5-ylmethyl)-2,3-dimethoxy-phenyl]-vinyl]-4-oxo-1,4-dihydro-quinoline-3-carboxylate (Example 15i)) there is obtained (E)-1-cyclohexyl-7-[2-[5-(2,4-diamino-pyrimidin-5-ylmethyl)-2,3-dimethoxy-phenyl]-vinyl]-4-oxo-1,4-dihydro-quinoline-3-carboxylic acid hydrochloride as a yellowish solid. Yield: 98%. M.p.>230°. Mass spectrum (ISP): 556.6 (M++H, 100%).

16ap) In analogy to Example 16c), from methyl 5-[5-(2,4-diamino-pyrimidin-5-ylmethyl)-2,3-dimethoxy-phenylethynyl]-2-hydroxy-benzoate (Example 12ah)) there is obtained 5-[5-(2,4-diamino-pyrimidin-5-ylmethyl)-2,3-dimethoxy-phenylethynyl]-2-hydroxy-benzoic acid hydrochloride as a beige solid. Yield: 39%. M.p.>230°. Mass spectrum (ISP): 421.4 (M++H, 100%).

16aq) In analogy to Example 16c), from ethyl 1-cyclohexyl-7-[5-(2,4-diamino-pyrimidin-5-ylmethyl)-2,3-dimethoxy-phenylethynyl]-6,8-difluoro-4-oxo-1,4-dihydro-quinoline-3-carboxylate (Example 12ai)) there is obtained 1-cyclohexyl-7-[5-(2,4-diamino-pyrimidin-5-ylmethyl)-2,3-dimethoxy-phenylethynyl]-6,8-difluoro-4-oxo-1,4-dihydro-quinoline-3-carboxylic acid hydrochloride as a yellowish solid. Yield: 89%. M.p.>230°. Mass spectrum (FAB): peaks inter alia at 590 (M++H, 100%), 526 (2%), 494 (3%).

16ar) A suspension of 0.33 g of 1-cyclohexyl-7-[5-(2,4-diamino-pyrimidin-5-ylmethyl)-2,3-dimethoxy-phenylethynyl]-6,8-difluoro-4-oxo-1,4-dihydro-quinoline-3-carboxylic acid hydrochloride (Example 16aq)) in 5 ml of methanol is treated with 2 ml of 28% aqueous sodium hydroxide solution and held at reflux for 5 hrs. The beige suspension is cooled to room temperature and acidified with 25% aqueous hydrochloric acid. The precipitated substance is filtered off under suction, washed with 10 ml of water, 10 ml of ethanol and 10 ml of ether and dried. 0.264 g (78%) of 1-cyclohexyl-7-[5-(2,4-diamino-pyrimidin-5-ylmethyl)-2,3-dimethoxy-phenylethynyl]-6-fluoro-8-methoxy-4-oxo-1,4-dihydro-quinoline-3-carboxylic acid hydrochloride is obtained as a beige solid. Yield: 78%. M.p.>205° (dec.). Mass spectrum (FAB): peaks inter alia at 602 (M++H, 100%), 588 (10%), 520 (7%).

16as) In analogy to Example 16c), from ethyl 7-[5-(2,4-diamino-pyrimidin-5-ylmethyl)-2,3-dimethoxy-phenylethynyl]-6,8-difluoro-4-oxo-1-phenyl-1,4-dihydro-quinoline-3-carboxylate (Example 12aj)) there is obtained 7-[5-(2,4-diamino-pyrimidin-5-ylmethyl)-2,3-dimethoxy-phenylethynyl]-6,8-difluoro-4-oxo-1-phenyl-1,4-dihydro-quinoline-3-carboxylic acid hydrochloride as a beige solid. Yield: 72%. M.p.>230°. Mass spectrum (ISP): 684.3 (M++H, 100%).

16at) 145 mg of 3-[5-(2,4-diamino-pyrimidin-5-ylmethyl)-2,3-dimethoxy-phenylethynyl]-4-hydroxy-5-methoxy-benzaldehyde (Example 12ao)) are dissolved in 5 ml of methanol and treated at 0° with 80 mg of sodium borohydride. The mixture is stirred at room temperature for a further 15 min., then concentrated and the residue is chromatographed on silica gel with methylene chloride/methanol 9:1. 3-[5-(2,4-Diamino-pyrimidin-5-yl-methyl)-2,3-dimethoxy-phenylethynyl]-4-hydroxymethyl-6-methoxy-phenol is isolated as a colourless solid. Yield: 74%. Mass spectrum (ISP): peaks inter alia at m/e: 437.5 (M++H, 100%).

16au) 146 mg of 5-[3-(3,5-bis-methoxymethoxy-naphthalen-2-ylethynyl)-4,5-dimethoxybenzyl]-pyrimidin-2,4-diamine (Example 12ap)) in 2.5 ml of THF, 2.5 ml of water and 2.5 ml of 6N hydrochloric acid are held at 50° for 7.5 hrs. The mixture is concentrated and the residue is chromatographed on silica gel with methylene chloride/methanol 9:1. 59 mg of 6-[5-(2,4-diamino-pyrimidin-5-ylmethyl)-2,3-dimethoxy-phenylethynyl]-naphthalene-1,7-diol are isolated as a yellowish solid. Yield: 48%. Mass spectrum: peaks inter alia at 443 (M++H, 100%).

16av) In analogy to Example 16at), from 3-[5-(2,4-diamino-pyrimidin-5-ylmethyl)-2,3-dimethoxy-phenylethynyl]-4,5-dimethoxy-benzaldehyde (Example 12aq) there is obtained [3-[5-(2,4-diamino-pyrimidin-5-ylmethyl)-2,3-dimethoxy-phenylethynyl]-4,5-dimethoxy-phenyl]-methanol as a colourless solid. Yield: 53%. Mass spectrum: peaks inter alia at 451 (M++H, 100%).

16ax) In analogy to Example 16ar), from ethyl 7-[5-(2,4-diamino-pyrimidin-5-ylmethyl)-2,3-dimethoxy-phenylethynyl]-4-oxo-1-(tetrahydrofuran-2-ylmethyl)-1,4-dihydro-quinoline-3-carboxylate (Example 12ax) there is obtained 7-[5-(2,4-diamino-pyrimidin-5-ylmethyl)-2,3-dimethoxy-phenylethynyl]-4-oxo-1-(tetrahydrofuran-2-ylmethyl)-1,4-dihydro-quinoline-3-carboxylic acid hydrochloride as a beige solid. Yield: 76%. M.p.=165° (decomposition).

16ay) In analogy to Example 16ar), from ethyl 3-[5-(2,4-diamino-pyrimidin-5-ylmethyl)-2,3-dimethoxy-phenylethynyl]-4,5-dimethoxy-benzoic acid (Example 12ba) there is obtained the corresponding 3-[5-(2,4-diamino-pyrimidin-5-ylmethyl)-2,3-dimethoxy-phenylethynyl]-4,5-dimethoxy-benzoic acid hydrochloride as a colourless solid. Yield: 83%. Mass spectrum: peaks inter alia at m/e : 465 (M++H, 100%); 256 (15%).

16az) In analogy to Example 16ar), from ethyl 7-[5-(2,4-diamino-pyrimidin-5-ylmethyl)-2,3-dimethoxyphenylethynyl]-4-oxo-1-(tetrahydro-pyran-4-yl)-1,4-dihydro-quinoline-3-carboxylate (Example 12bc) there is obtained 7-[5-(2,4-diamino-pyrimidin-5-ylmethyl)-2,3-dimethoxy-phenylethynyl]-4-oxo-1-(tetrahydro-pyran-4-yl)-1,4-dihydro-quinoline-3-carboxylic acid as a beige solid. Yield: 78%. M.p.=253°.

16ba) 75 mg of tert.-butyl ([3-[5-(2,4-diamino-pyrimidin-5-ylmethyl)-2,3-dimethoxy-phenylethynyl]-phenylcarbamate (Example 12bn)) are dissolved in 2 ml of ethyl acetate and treated with a few drops of a saturated solution of hydrogen chloride in ether. The mixture is stirred at room temperature for 2 hrs. and then concentrated. 66 mg of tert.-butyl ([3-[5-(2,4-diamino-pyrimidin-5-ylmethyl)-2,3-dimethoxy-phenylethynyl]-phenylcarbamate are isolated as a brownish solid. Yield: 100%. M.p.=179° (decomposition).

16bb) 150 mg of diethyl [4-[5-(2,4-diamino-pyrimidin-5-ylmethyl)-2,3-dimethoxy-phenylethynyl]-phenyl]-phosphonate (Example 12bo)) are dissolved in 7 ml of ethanol and treated with 2 ml of a 2N sodium hydroxide solution. The solution is held under reflux for 45 min., then cooled and chromatographed on MCl-gel with water/acetonitrile. 74 mg of monoethyl [4-[5-(2,4-diamino-pyrimidin-5-ylmethyl)-2,3-dimethoxy-phenylethynyl]-phenyl]-phosphonate sodium salt are isolated. Yield: 50%. Mass spectrum: peaks inter alia at m/e: 491 (M++Na, 10%), 469.2 (M++H, 100%), 419.4 (15%), 413.3 (20%), 391.3 (45%).

16bc) 150 mg of diethyl [4-[5-(2,4-diamino-pyrimidin-5-ylmethyl)-2,3-dimethoxy-phenylethynyl]-phenyl]-phosphonate (Example 12bo)) are dissolved in 5 ml of ethanol and treated with 5 ml of a 2N sodium hydroxide solution. The solution is held under reflux for 2 hrs., then cooled and chromatographed on MCl gel with water/acetonitrile. 43 mg of [4-[5-(2,4-diamino-pyrimidin-5-ylmethyl)-2,3-dimethoxy-phenylethynyl]-phenyl]-phosphonic acid disodium salt are isolated. Yield: 29%. Mass spectrum: peaks inter alia at m/e: 463 (M++Na, 30%), 441 (M++H, 100%), 412 (22%).

16bd) 0.5 g of ethyl 1-[2-(tert-butyl-dimethyl-silanyloxy)-1,1-dimethyl-ethyl]-7-[5-(2,4-diamino-pyrimidin-5-ylmethyl)-2,3-dimethoxy-phenylethynyl]-4-oxo-1,4-dihydro-quinoline-3-carboxylate (Example 12bq)) were dissolved in 10 ml of tetrahydrofuran under argon and cooled in ice. Then, 0.8 ml of a 1M solution of tetrabutylammonium fluoride in tetrahydrofuran was added. The mixture was left to warm and was stirred at room temperature for a further 15 min. Then, it was chromatographed directly on silica gel in dichloromethane/methanol 109:1 and crystallized from 5 ml of methanol. 209 mg (50%) of ethyl 7-[5-(2,4-diamino-pyrimidin-5-ylmethyl)-2,3-dimethoxy-phenylethynyl-1-(2-hydroxy-1,1-dimethyl-ethyl)-4-oxo-1,4-dihydro-quinoline-3-carboxylate were obtained as M.p. 224°.

16be) 150 mg of ethyl [E/Z]-2-{2-chloro-4-[5-(2,4-diamino-pyrimidin-5-ylmethyl)-2,3-dimethoxy-phenylethynyl]-benzoyl}-3-dimethylamino-acrylate (Example 12br)) were dissolved in 4 ml of ethanol at 0°, treated with 0.3 ml of 1N sodium hydroxide solution and stirred at 80° for 10 min. Then, the mixture was acidified with an excess of 1N hydrochloric acid until the product separated. 33 mg (22%) of ethyl [E/Z]-2-{2-chloro-4-[5-(2,4-diamino-pyrimidin-5-ylmethyl)-2,3-dimethoxy-phenylethynyl]-benzoyl}-3-ethoxy-acrylate were obtained as beige crystals. M.p.>250°. Mass spectrum (ISP): peaks inter alia at 537.4 (M+H, 100%), 509.4 (15%), 419.4 (15%).

16bf) 140 mg of (7S,8R,9R,10S,22S,23R,24R,25S)-7,8,9,10,22,23,24,25-octaacetoxy-3,18-bis-[5-(2,4-diamino-pyrimidin-5-ylmethyl)-2,3-dimethoxy-phenylethinyl]-5,6,7,8,9,10,20,21,22,23,24,25,26-tetracahydro-5,29:14,20-dimetheno-dibenzo-[b,o][7,20,1,14]dioxadiazacyclohexacosin-13,15,28,30-tetraone (Example 12bu)) were boiled at reflux in 2 ml of ethanol and 1N NaOH for 20 min. Then, the mixture was treated with 2 ml of ethanol and 2 ml of 1N HCl, whereupon the product separated. 70 mg (62%) of 7-[5-(2,4-diamino-pyrimidin-5-ylmethyl)-2,3-dimethoxy-phenylethynyl]-4-oxo-1-(2,3,4,5,6-pentahydroxyhexyl)-1,4-dihydro-quinoline-3-carboxylic acid were obtained as yellow crystals. M.p. 250° (decomposition). Mass spectrum (ISP): peaks inter alia at 636.4 (M+H, 100%).

16bg) 200 mg of ethyl [E/Z]-3-{4-[5-(2,4-diamino-pyrimidin-5-ylmethyl)-2,3-dimethoxy-phenylethinyl]-phenyl}-2-hydroxyimino-3-oxo-propionate (Example 12bu)) were stirred at 80° in 6 ml of ethanol and 6 ml of 1N NaOH for 1 hr. and then evaporated. The residue was dissolved in 2 ml of water and acidified to pH 5 with 1N HCl. 146 mg (77%) of [E/Z]-3-{4-[5-(2,4-diamino-pyrimidin-5-ylmethyl)-2,3-dimethoxy-phenylethynyl]-phenyl}-2-hydroxyimino-3-oxo-propionic acid were obtained as yellow crystals. M.p. 245° (decomposition). Mass spectrum (EI): peaks inter alia at 474 (M+H, 55%), 412 (30%), 403 (100%).

16bh) In analogy to Example 16bg), with ethyl [E/Z]-3-{4-[5-(2,4-diamino-pyrimidin-5-ylmethyl)-2,3-dimethoxy-phenylethynyl]-phenyl}-2-methoxyimino-3-oxo-propionate there is obtained 4-[5-(2,4-diamino-pyrimidin-5-ylmethyl)-2,3-dimethoxy-phenylethynyl]-benzoic acid. Yield: 76%. M.p. 190° (decomposition). Mass spectrum (ISP): peaks inter alia at 403 (M−H, 100%).

16bi) 380 mg of ethyl [E/Z]-3-{2-chloro-4-[5-(2,4-diamino-pyrimidin-5-ylmethyl)-2,3-dimethoxy-phenylethynyl]-phenyl}-3-oxo-2-trityloxyimino-propionate (Example 12by)) in 2.8 ml of trifluoroacetic acid were treated at room temperature with 0.064 ml of triethylsilane, stirred for 2 hrs. and then concentrated. The residue was taken up in water at pH 5 and extracted with dichloromethane. Chromatography: silica gel, dichloromethane, then dichloromethane/methanol 10:1. 65 mg (34%) of ethyl [E/Z]-3-{2-chloro-4-[5-(2,4-diamino-pyrimidin-5-ylmethyl)-2,3-dimethoxy-phenylethynyl]-phenyl}-2-hydroxyimino-3-oxo-propionate were obtained as beige crystals. M.p. 208° (decomposition). Mass spectrum (ISP): peaks inter alia at 538 (M+H, 100%).

16bj) A solution of 430 mg (0.72 mmol) of ethyl [4-[5-(2,4-diamino-pyrimidin-5-ylmethyl)-2,3-dimethoxy-phenylethynyl]-phenyl]-trifluoro-methylsulphonyl)-amino]-acetate (Example 12ce)) in 15 ml of ethanol and 15 ml of 2N sodium hydroxide solution as stirred at room temperature for 1.5 hours. Then, the ethanol was drawn off, the aqueous phase was adjusted to about pH 3 with 2N hydrochloric acid solution and extracted three times with 20 ml of ethyl acetate each time. The combined organic phases were washed neutral with sat. sodium chloride solution, dried over sodium sulphate and evaporated. The yellow residue was recrystallized from acetonitrile/0.1N hydrochloric acid solution. 264 mg (64%) of [4-[5-(2,4-diamino-pyrimidin-5-ylmethyl)-2,3-dimethoxy-phenylethynyl]-phenyl]-trifluoromethylsulphonyl)-amino]-acetic acid were obtained as a pale yellow powder of m.p.>300°. MS (ISP): 566 ([M+H]+, 100%).

EXAMPLE A

| Tablets | |
|---|---|
| Sulfamethoxazole | 400 mg |
| Compounds of formula I, e.g. 2-cyclohexyl-7-[5-(2,4-diamino-pyrimidin-5-ylmethyl)-2,3-dimethoxy-phenylethynyl]-4-oxo-1,4-dihydro-quinoline-3-carboxylic acid hydrochloride | 80 mg |
| PRIMOJEL (starch derivative) | 6 mg |
| POVIDONE K30 (polyvinylpyrrolidone) | 8 mg |
| Magnesium stearate | 6 mg |
| Total weight | 500 mg |

EXAMPLE B

| Tablets | |
|---|---|
| Compounds of formula I, e.g. 1-cyclohexyl-7-[5-(2,4-diamino-pyrimidin-5-ylmethyl)-2,3-dimethoxy-phenylethynyl]-6,8-difluoro-1,4-dihydro-4-oxo-quinoline-3-carboxylic acid hydrochloride | 100 mg |
| Corn starch | 15 mg |
| Talc | 3 mg |
| Magnesium stearate | 2 mg |
| Total weight | 120 mg |

We claim:

1. A compound of the formula:

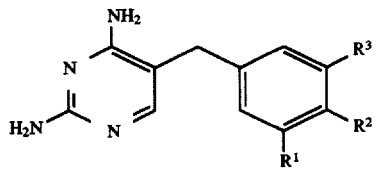

in which $R^1$ is lower alkoxy, $R^2$ is bromine or lower alkoxy, and $R^3$ is aryl;
hydrolyzable esters of the compound of formula I; and pharmaceutically acceptable salts of this compound.

2. A compound of the formula:

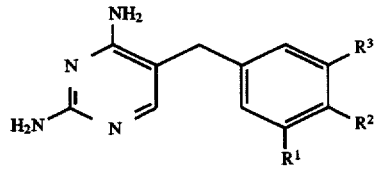

in which $R^1$ is lower alkoxy, $R^2$ is bromine or lower alkoxy, and $R^3$ is a residue of

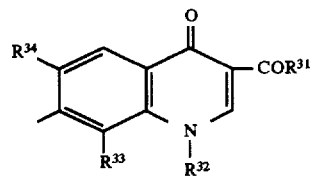

in which $R^{31}$ is hydroxy, lower-alkoxy, amino, (hydroxy-lower-alkyl)amino, di-lower-alkylamino-lower-alkoxy or morpholino-lower-alkoxy, $R^{32}$ is hydrogen, lower-alkyl, hydroxy-lower-alkyl, phenyl, cyclohexyl, aminocyclohexyl, cyclopentyl, cyclopropyl, cyclopropylmethyl, 2,2,2-trifluoroethyl, pyridylmethyl, piperidylmethyl, adamantyl, bicyclo[2.2.1]hept-2-yl, 2-(tert.-butyl-dimethylsilanyloxy)-1, 1-dimethylethyl, 2-(2-(2-hydroxyethoxy)ethoxy)ethyl, furylmethyl, tetrahydrofurylmethyl, tetrahydropyranyl, or aryl-lower-alkyl, and $R^{33}$ and $R^{34}$ each independently is hydrogen, fluorine, hydroxy, or methoxy,
hydrolyzable esters of the compound of formula I; and pharmaceutically acceptable salts of this compound.

3. A compound of the formula:

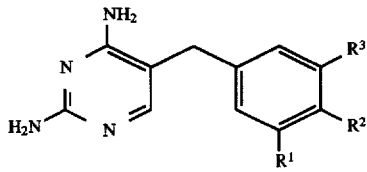

in which $R^1$ is lower alkoxy, $R^2$ is bromine or lower alkoxy, and $R^3$ is the group —Q—$R^{30}$ in which Q is vinylene or ethynylene, and $R^{30}$ is aryl; hydrolyzable esters of the compound of formula I; and pharmaceutically acceptable salts of this compound.

4. A compound of the formula:

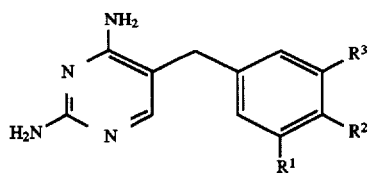

in which $R^1$ is lower alkoxy, $R^2$ is bromine or lower alkoxy, and $R^3$ is the group —Q—$R^{30}$ in which Q is vinylene or ethynylene, and $R^{30}$ is heteroaryl;
hydrolyzable esters of the compound of formula I; and pharmaceutically acceptable salts of this compound.

5. A method for treating infectious diseases which comprises administering an effective amount of a compound of the formula:

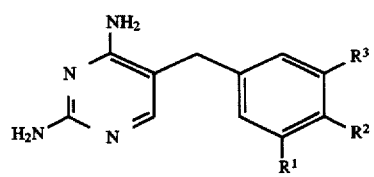

in which $R^1$ is lower alkoxy, $R^2$ is bromine or lower alkoxy, and $R^3$ is aryl;
hydrolyzable esters of the compound of formula I; and pharmaceutically acceptable salts of this compound.

6. A method for treating infectious diseases which comprises administering an effective amount of a compound of the formula:

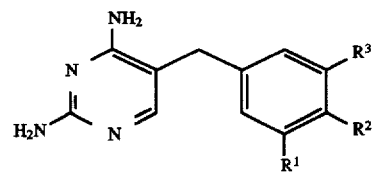

in which $R^1$ is lower alkoxy, $R^2$ is bromine or lower alkoxy, and $R^3$ is a residue of

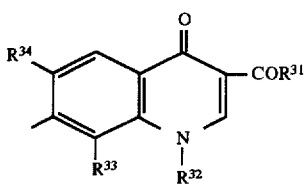

in which $R^{31}$ is hydroxy, lower-alkoxy, amino, (hydroxy-lower-alkyl)amino, di-lower-alkylamino-lower-alkoxy or morpholino-lower-alkoxy, $R^{32}$ is hydrogen, lower-alkyl, hydroxy-lower-alkyl, phenyl, cyclohexyl, aminocyclohexyl, cyclopentyl, cyclopropyl, cyclopropylmethyl, 2,2,2-trifluoroethyl, pyridylmethyl, piperidylmethyl, adamantyl, bicyclo[2.2.1]hept-2-yl, 2-(tert-butyl-dimethylsilanyloxy)-1,1-dimethylethyl, 2-(2-(2-hydroxyethoxy)ethoxy)ethyl, furylmethyl, tetrahydrofurylmethyl tetrahydropyranyl, or aryl-lower-alkyl, and $R^{33}$ and $R^{34}$ each independently is hydrogen, fluorine, hydroxy, or methoxy, hydrolyzable esters of the compound of formula I; and pharmaceutically acceptable salts of this compound.

7. A method for treating infectious diseases which comprises administering an effective amount of a compound of the formula:

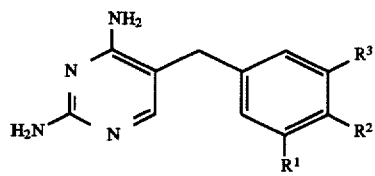

in which $R^1$ is lower alkoxy, $R^2$ is bromine or lower alkoxy, and $R^3$ is the group —Q—$R^{30}$ in which Q is vinylene or ethynylene, and $R^{30}$ is aryl; hydrolyzable esters of the compound of formula I; and pharmaceutically acceptable salts of this compound.

8. A method for treating infectious diseases which comprises administering an effective amount of a compound of the formula:

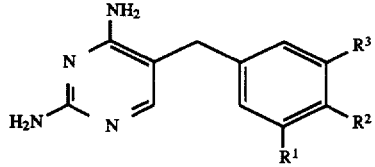

in which $R^1$ is lower alkoxy, $R^2$ is bromine or lower alkoxy, and $R^3$ is the group —Q—$R^{30}$ in which Q is vinylene or ethynylene, and $R^{30}$ is heteroaryl; hydrolyzable esters of the compound of formula I; and pharmaceutically acceptable salts of this compound.

9. The compound of claim 4 which is 1-ethyl-7[5-(2,4-diamino-pyrimidin-5-ylmethyl)-2,3-dimethoxy-phenylethynyl]-4-oxo-1,4-dihydro-quinoline-3-carboxylic acid.

10. The compound of claim 34 which is 5-(3,4-dimethoxy-5-naphthalen-2-yl-benzyl)-pyrimidine-2,4-diamine.

11. The compound according to claim 2, selected from the group consisting of:

1-cyclopropyl-7-[5-(2,4-diamino-pyrimidin-5-ylmethyl)-2,3-dimethoxy-phenyl]-6-fluoro-4-oxo-1,4-dihydro-quinoline-3-carboxylic acid, 1-cyclopropyl-7-[5-(2,4-diamino-pyrimidin-5-ylmethyl)-phenyl]-6-fluoro-4-oxo-1,4-dihydro-quinoline-3-carboxylic acid, and 1-cyclopropyl-7-[5-(2,4-diamino-pyrimidin-5-ylmethyl)-2-methoxyphenyl]-6-fluoro-4-oxo-1,4-dihydro-quinoline-3-carboxylic acid;

and their pharmaceutically usable salts.

12. The compound of claim 11 which is 1-cyclopropyl-7-[5-(2,4-diamino-pyrimidin-5-ylmethyl)-phenyl3-6-fluoro-4-oxo-1,4-dihydro-quinoline-3-carboxylic acid.

13. The compound of claim 11 which is 1-cyclopropyl-7-[5-(2,4-diamino-pyrimidin-5-ylmethyl)-2-methoxy-phenyl]-6-fluoro-4-oxo-1,4-dihydro-quinoline-3-carboxylic acid.

14. The compound of claim 11 which is 1-cyclopropyl-7-[5-(2,4-diamino-pyrimidin-5-ylmethyl)-2,3-dimethoxy-phenyl]-6-fluoro-4-oxo-1,4-dihydro-quinoline-3-carboxylic acid.

15. The compound according to claim 4, wherein $R^{30}$ is a residue of the formula:

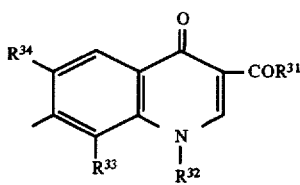

in which $R^{31}$ is hydroxy, lower-alkoxy, amino, (hydroxy-lower-alkyl)amino, di-lower-alkylamino-lower-alkoxy, or morpholino-lower-alkoxy, $R^{32}$ is hydrogen, lower-alkyl, phenyl, cyclohexyl, aminocyclohexyl, cyclopentyl, cyclopropyl cyclopropylmethyl, 2,2,2-trifluoroethyl, pyridylmethyl, piperidylmethyl, adamantyl, bicyclo2.2.1]hept-2-yl, 2-(tert.-butyl-dimethylsilanyloxy)-1,1-dimethylethyl, 2-(2-(2-hydroxyethoxy)ethoxy)ethyl, furylmethyl, tetrahydrofurylmethyl, tetrahydropyranyl, or aryl-lower-alkyl, and $R^{33}$ and $R^{34}$ each independently is hydrogen, fluorine, hydroxy, or methoxy.

16. The compound according to claim 15, selected from the group consisting of:

1-cyclohexyl-7-[5-(2,4-diamino-pyrimidin-5-ylmethyl)-2,3-dimethoxy-phenylethynyl]-4-oxo-1,4-dihydro-quinoline-3-carboxylic acid, 1-cyclopropyl-7-[5-(2,4-diamino-pyrimidin-5-ylmethyl)-2,3-dimethoxy-phenylethynyl-1]-6,8-difluoro-4-oxo-1,4-dihydro-quinoline-3-carboxylic acid, 1-cyclopropyl-7-[5-(2,4-diamino-pyrimidin-5-ylmethyl)-2,3-dimethoxy-phenylethynyl-1]-6-fluoro-4-oxo-1,4-dihydro-quinoline-3-carboxylic acid, 1-benzyl-7-[5-(2,4-diamino-pyrimidin-5-ylmethyl)-2,3-dimethoxy-phenylethynyl]-1-methyl-4-oxo-1,4-dihydro-quinoline-3-carboxylic acid, 1-tert-butyl-7-[5-(2,4-diamino-pyrimidin-5-ylmethyl)-2,3-dimethoxy-phenylethynyl]-4-oxo-1,4-dihydro-quinoline-3-carboxylic acid, and ethyl 1-ethyl-7-[5-(2,4-diamino-pyrimidin-5-ylmethyl)-2,3-dimethoxy-phenylethynyl]-4-oxo-1,4-dihydro-quinoline-3-carboxylate; and their pharmaceutically usable salts.

17. The compound of claim 16 which is 1-cyclopropyl-7-[5-(2,4-diamino-pyrimidin-5-ylmethyl)-2,3-dimethoxy-phenylethynyl-1]-6,8-difluoro-4-oxo-1,4-dihydro-quinoline-3-carboxylic acid.

18. The compound of claim 16 which is 1-cyclopropyl-7-[5-(2,4-diamino-pyrimidin-5-ylmethyl)-2,3-dimethoxy-phenylethynyl-1]-6-fluoro-4-oxo-1,4-dihydro-quinoline-3-carboxylic acid.

19. The compound of claim 16 which is 1-benzyl-7-[5-(2,4-diamino-pyrimidin-5-ylmethyl)-2,3-dimethoxy-phenylethynyl]-1-methyl-4-oxo-1,4-dihydro-quinoline-3-carboxylic acid.

20. The compound of claim 16 which is 1-cyclohexyl-7-[5-(2,4-diamino-pyrimidin-5-ylmethyl)-2,3-dimethoxy-phenylethynyl]-4-oxo-1,4-dihydro-quinoline-3-carboxylic acid.

21. The compound of claim 16 which is 1-cyclohexyl-7-[5-(2,4-diamino-pyrimidin-5-ylmethyl)-2,3-dimethoxy-phenylethynyl]-4-oxo-1,4-dihydro-quinoline-3-carboxylic acid.

22. The compound according to claim 1, selected from the group consisting of:

5-(5,6-dimethoxy-biphenyl-3-ylmethyl)-pyrimidine-2,4-diamine, 5-(4'-fluoro-5,6-dimethoxy-biphenyl-3-ylmethyl)-pyrimidine-2,4-diamine, 5-(4'-t-butyl-dimethylsilyloxy-5,6-dimethoxy-biphenyl-3-ylmethyl)-pyrimidine-2,4-diamine, 5-(3'-t-butyl-dimethylsilyloxy-5,6-dimethoxy-biphenyl-3-ylmethyl )-pyrimidine-2,4-diamine, 5-(4'-methoxycarbonyl-5,6-dimethoxy-biphenyl-3-ylmethyl)-pyrimidine-2,4-diamine, 5-(3'-methoxycarbonyl-5,6-dimethoxy-biphenyl-3-ylmethyl)-pyrimidine-2,4-diamine, 5-(4'-phenyl-5,6-dimethoxy-biphenyl-3-ylmethyl)-pyrimidine-2,4-diamine, 5-(4'-trifluoromethyl-5,6-dimethoxy-biphenyl-3-ylmethyl)-pyrimidine-2,4-diamine, 5-(4'-butyloxy-5,6-dimethoxy-biphenyl-3-ylmethyl)-pyrimidine-2,4-diamine, 5-(4'-pentenyl-5,6-dimethoxy-biphenyl-3-ylmethyl)-pyrimidine-2,4-diamine, 5-(4'-carbamoyl-5,6-dimethoxy-biphenyl-3-ylmethyl)-pyrimidine-2,4-diamine, 5-(4'-(4-amino-benzenesulphonyl)-5,6-dimethoxy-biphenyl-3-ylmethyl)-pyrimidine-2,4-diamine, 5-(4'-t-butyl-5,6-dimethoxy-biphenyl-3-ylmethyl)-pyrimidine-2,4-diamine, 5-(4'-sulphamoyl-5,6-dimethoxy-biphenyl-3-ylmethyl)-pyrimidine-2,4-diamine, 5-(3',4',5,6-tetramethoxy-biphenyl-3-ylmethyl)-pyrimidine-2,4-diamine, 5-(4'-dimethylamino-5,6-dimethoxy-biphenyl-3-ylmethyl)-pyrimidine-2,4-diamine, 5-(4'-diethylamino-5,6-dimethoxy-biphenyl-3-ylmethyl)-pyrimidine-2,4-diamine, 1,4-bis-(5-(2,4-diamino-pyrimidin-5-ylmethyl)-2,3-dimethoxy-phenyl)-benzene, 5-(3'-amino-5,6-dimethoxy-biphenyl-3-ylmethyl)-pyrimidine-2,4-diamine, 5-(3'-(2-ethoxycarbonyl-acetylamino)-5,6-dimethoxy-biphenyl-3-ylmethyl)-pyrimidine-2,4-diamine, 5-(3'-(4-nitrobenzenesulphonylamino)-5,6-dimethoxy-biphenyl-3-ylmethyl)-pyrimidine-2,4-diamine, 5-(3,4-dimethoxy-5-naphthalen-1-yl-benzyl)-pyrimidine-2,4-diamine, 5-(3'-furan-2-carbonylamino)-5,6-dimethoxy-biphenyl-3-ylmethyl)-pyrimidine-2,4-diamine, 5-(3'-(4-methoxycarbonyl-n-butyrylamino)-5,6-dimethoxy-biphenyl-3-ylmethyl)-pyrimidine-2,4-diamine, 5-(3'-(4-methoxycarbonyl-benzoyl)-amino)-5,6-dimethoxy-biphenyl-3-ylmethyl)-pyrimidine-2,4-diamine, 5-(3,4-dimethoxy-5-naphthalen-6-(t-butyl-dimethyl-silyloxy)-2-yl-benzyl)-pyrimidine-2,4-diamine, N-[5'-(2,4-diamino-pyrimidin-5-ylmethyl)-2',3'-dimethoxy-biphenyl-3-yl)-2-hydroxy-benzamid, 5-(3'-(2-methoxycarbonylethyl-amino)-5,6-dimethoxy-biphenyl-3-ylmethyl)-pyrimidine-2,4-diamine, 2-chloro-3-[5'-(2,4-diamino-pyrimidin-5-ylmethyl)-2',3'-dimethoxy-biphenyl-3-ylamino][1,4]-naphthoquinone, ethyl 1-cyclopropyl-7-[4-[5'-(2,4-diamino-pyrimidin-5-ylmethyl)-2',3'-dimethoxy-biphenyl-4-ylmethyl]-piperazin-1-yl]-6,8-difluoro-4-oxo-1,4-dihydro-quinoline-3-carboxylate, methyl 3-[5'-(2,4-diamino-pyrimidin-5-ylmethyl)-2',3'-dimethoxy-biphenyl-4-yl]-acrylate, 5'-(2,4-diamino-pyrimidin-5-ylmethyl)-2',3'-dimethoxy-biphenyl -4-carbaldehyde oxime 5'-(2,4-diamino-pyrimidin-5-ylmethyl)-2',3'-dimethoxy-biphenyl-4-carbaldehyde, 5-[5,6-dimethoxy-4'-(1H-tetrazol-5-yl)-biphenyl-3-ylmethyl]-pyrimidine-2,4-diamine, diethyl 2-[5'-(2,4-diamino-pyrimidin-5-ylmethyl)-2',3'-dimethoxy-biphenyl-4-ylmethylene]-malonate, 5-(4'-hydroxy-5,6-dimethoxy-biphenyl-3-ylmethyl)-pyrimidine-2,4-diamine, 5-(3'-carboxy-5,6-dimethoxy-biphenyl-3-ylmethyl)-pyrimidine, 2,4-diamine, 5-(3'-(4-aminobenzenesulphonylamino)-5,6-dimethoxy-biphenyl-3-ylmethyl)-pyrimidine-2,4-diamine, 5-(3'-(4-carboxy-n-butyrylamino)-5,6-dimethoxy-biphenyl-3-ylmethyl)-pyrimidine-2,4-diamine, 5-(3'-(4-carboxy-benzoyl)-amino)-5,6-dimethoxy-biphenyl-3-ylmethyl)-pyrimidine-2,4-diamine, 5-(3,4-dimethoxy-5-naphthalen-6-hydroxy-2-yl-benzyl)-pyrimidine-2,4-diamine, 5-(3'-(2-carboxyethyl-amino)-5,6-dimethoxy-biphenyl-3-ylmethyl)-pyrimidine-2,4-diamine, 5-(4'-pivaloyloxymethylcarbonyl-5,6-dimethoxy-biphenyl-3-ylmethyl)-pyrimidine-2,4-diamine, 1-cyclopropyl-7-[4-[5'-(2,4-diamino-pyrimidin-5-ylmethyl)-2',3'-dimethoxy-biphenyl-4-ylmethyl]-piperazin-1-yl]-6,8-difluoro-4-oxo-1,4-dihydro-quinoline-3-carboxylic acid hydrochloride, 3-[5'-(2,4-diamino-pyrimidin-5-ylmethyl)-2',3'-dimethoxy-biphenyl- 4-yl-acrylic acid, and

[5'-(2,4-diamino-pyrimidin-5-ylmethyl)-2',3'-dimethoxy-biphenyl-4-yl]-methanol.

23. The compound according to claim 3, selected from the group consisting of:

5-(3,4-dimethoxy-5-(2,6-dimethyl-4-pyridinyl)-benzyl)-pyrimidine-2,4-diamine, 5-(3,4-dimethoxy-5-(5-pyridinyl)-benzyl)-pyrimidine-2,4-diamine, 5-(3,4-dimethoxy-5-(3-pyridinyl)-benzyl-pyrimidine-2,4-diamine, 5-(3,4-dimethoxy-5-(4-pyridinyl)-benzyl-pyrimidine-2,4-diamine, ethyl 7-[5-(2,4-diamino-pyrimidin-5yl-methyl)-2,3-dimethoxy-phenyl]-1-ethyl-1,4-dihydro-4-oxo-quinoline-3-carboxylate ethyl 7-[5-(3-diamino-pyrimidin-5yl-methyl)-2-methoxy-phenyl]-1-ethyl-1,4-dihydro-4-oxo-quinoline-3-carboxylate, 5-(3-furan-2-yl-4,5-dimethoxy-benzyl)-pyrimidine-2,4-diamine, 5-(3-(1H-indol-5-yl)-4,5-dimethoxybenzyl]-pyrimidine-2,4-diamine, 5-(3-benzofuran-2-yl-4,5-dimethoxy-benzyl)-pyrimidine-2,4-diamine, methyl 3-[5-[5-(2,4-diaminopyrimidin-5-ylmethyl)-2,3-dimethoxyphenyl]-furan-2-yl-acrylate, 5-[5-(2,4-diamino-pyrimidin-5-ylmethyl)-2,3-dimethoxy-phenyl]-furan-2-carbaldehyde oxime, 5-[5-(2,4-diamino-pyrimidin-5-ylmethyl)-2,3-dimethoxy-phenyl]-furan-2-carbaldehyde, 5-(3-furan-3-yl-4,5-dimethoxy-benzyl)-pyrimidine-2,4-diamine, 5-(3-[2,2']-bifuranyl-5-yl-4,5-dimethoxy-benzyl)-pyrimidine-2,4-diamine, 7-[5-(2,4-diamino-pyrimidin-5-ylmethyl)-2,3-dimethoxy-phenyl]-1-ethyl-1,4-dihydro-4-oxo-quinoline-3-carboxylic acid hydrochloride, 7-[5-(2,4-diamino-pyrimidin-5-ylmethyl)-2-methoxy-phenyl]-1-ethyl-1,4-dihydro-4-oxo-quinoline-3-carboxylic acid hydrochloride, 3-[5-[5-(2,4-diaminopyrimidin-5-ylmethyl)-2,3-dimethoxyphenyl]-furan-2-yl-acrylic acid, and ethyl 1-ethyl-7-[5-(2,4-diamino-pyrimidin-5-ylmethyl)-2,3-dimethoxy-phenylethynyl]-6-fluoro-$^4$-oxo-1,4-dihydro-quinoline-3-carboxylate.

24. The compound according co claim 3, selected from the group consisting of:

5-(3,4-dimethoxy-5-styryl-benzyl)-pyrimidine-2,4-diamine, 5-(3,4-dimethoxy-5-(3',4'-dimethoxy-styryl)-benzyl]-pyrimidine-2,4-diamine, 5-(3-(2-biphenyl-4-yl-vinyl)-4,5-dimethoxy-benzyl]-pyrimidine-2,4-diamine, 5-[3,4-dimethoxy-5-(4'-dimethylamino-styryl)-benzyl]-pyrimidine-2,4-diamine, 5-[3,4-dimethoxy-5-(1-naphthalen-2-yl-vinyl)-benzyl]-pyrimidine-2,4-diamine, 5-[3-(2-(4-dimethylaminomethyl-phenyl)-vinyl]-4,5-dimethoxy-benzyl}-pyrimidine-2,4-diamine, 5-[3,4-dimethoxy-5-(4'-hydroxystyryl)-benzyl]-pyrimidine-2,4-diamine, ethyl 6-[5-(2,4-diamino-pyrimidin-5-ylmethyl)-2,3-dimethoxy-phenylethynyl]-naphthalen-2-carboxylate, methyl 4-[5-(2,4-diamino-pyrimidin-5-ylmethyl)-2,3-dimethoxy-phenylethynyl]-2-hydroxy-benzoate, 2-chloro-4-[5-(2,4-diamino-pyrimidin-5-ylmethyl)-2,3-dimethoxy-phenylethynyl]-acetophenone, methyl 5-[5-(2,4-diamino-pyrimidin-5-ylmethyl)-2,3-dimethoxy-phenylethynyl]-2-hydroxy-benzoate, N-{4-[5-(2,4-diamino-pyrimidin-5-ylmethyl)-2,3-dimethoxy-phenylethynyl]-benzoyl}-methanesulphonamide, 5-[3-(3,5-dimethoxy-naphthalen-2-ylethynyl)-4,5-dimethoxy-benzyl]-pyrimidine-2,4-diamine, 3-[5-(2,4-diamino-pyrimidin-5-ylmethyl)-2,3-dimethoxy-phenylethynyl]-4-hydroxy-5-methoxy-benzaldehyde, 5-[3-(3,5-bis-methoxymethoxy-naphthalen-2-ylethynyl)-4,5-dimethoxybenzyl]-pyrimidine-2,4-diamine, 3-[5-(2,4-diamino-pyrimidin-5-ylmethyl)-2,3-dimethoxy-phenylethynyl]-4,5-dimethoxy-benzaldehyde, cyclopropanecarboxylic acid acetyl-[3-[5-(2,4-diamino-pyrimidin-5-ylmethyl)-2,3-dimethoxy-phenylethynyl]-phenyl]-amide, 3-[5-(2,4-diamino-pyrimidin-5-ylmethyl)-2,3-dimethoxy-phenylethynyl]-4,5-dimethoxy-benzaldehyde oxime, cyclopropanecarboxylic acid (2-cyano-ethyl)-[3-[5-(2,4-diamino-pyrimidin-5-ylmethyl)-2,3-dimethoxy-phenylethynyl]-phenyl]-amide, 3-[5-(2,4-diamino-pyrimidin-5-ylmethyl)-2,3-dimethoxy-phenylethynyl]-4,5-dimethoxy-benzonitrile, ethyl 3-[5-(2,4-diamino-pyrimidin-5-ylmethyl)-2,3-dimethoxy-phenylethynyl]-4,5-dimethoxy-benzoate, cyclopropanecarboxylic acid cyclopropancarbonyl-[3-[5-(2,4-diamino-pyrimidin-5-ylmethyl)-2,3-dimethoxy-phenylethynyl]-phenyl]-amide, 1-[3-[5-(2,4-diamino-pyrimidin-5-ylmethyl)-2,3-dimethoxy-phenylethynyl]-4,5-dimethoxy-phenyl]-ethanone, 1-(3-[5-(2,4-diamino-pyrimidin-5-ylmethyl)-2,3-dimethoxy-phenylethynyl]-4-hydroxy-5-methoxy-phenyl]-ethanone, ethyl 3-[3-[5-(2,4-diamino-pyrimidin-5-ylmethyl)-2,3-dimethoxy-phenylethynyl]-4,5-dimethoxy-phenyl]-3-oxo-propionate, cyclopropanecarboxylic acid [3-[5-(2,4-diamino-pyrimidin-5-ylmethyl)-2,3-dimethoxy-phenylethynyl-phenyl]-amide, furan-2-carboxylic acid [3-[5-(2,4-diamino-pyrimidin-5-ylmethyl)-2,3-dimethoxy-phenyl]-(furan-2-carbonyl)-amide, 5-[3,4-dimethoxy-5-[3-(tetrahydro-pyran-4-ylamino)-phenylethynyl]-benzyl]-pyrimidine-2,4-diamine, furan-2-carboxylic acid [3-[5-(2,4-diamino-pyrimidin-5-ylmethyl)-2,3-dimethoxy-phenylethynyl]-phenyl]-amide, cyclopropanecarboxylic acid [3-(5-(2,4-diamino-pyrimidin-5-ylmethyl)-2,3-dimethoxy-phenylethynyl]-phenyl]-(furan-2-carbonyl)-amide, cyclopropanecarboxylic acid [3-[5-(2,4-diamino-pyrimidin-5-ylmethyl)-2,3-dimethoxy-phenylethynyl]-phenyl]-(tetrahydro-pyran-4-yl)-amide, N-cyclopropyl-5-[5-(2,4-diamino-pyrimidin-5-ylmethyl)-2,3-dimethoxy-phenylethynyl)-2-hydroxy-benzamide, tert. butyl ([3-[5-(2,4-diamino-pyrimidin-5-ylmethyl)-2,3-dimethoxy-phenylethynyl]-phenylcarbamate, diethyl [4-[5-(2,4-diamino-pyrimidin-5-ylmethyl)-2,3-dimethoxy-phenylethynyl]-phenyl]-phosphonate, 3-[5-(2,4-diamino-pyrimidin-5-ylmethyl)-2,3-dimethoxy-phenyl-ethynyl]-N-(di-pyridin-2-yl-methyl)-benzamide, ethyl [E/Z]-2-(2-chloro-4-[5-(2,4-diamino-pyrimidin-5-ylmethyl)-2,3-dimethoxy-phenylethynyl]-benzoyl}-3-dimethylamino-acrylate, cyclopropyl-{4-[5-(2,4-diamino-pyrimidin-5-ylmethyl)-2,3-dimethoxy-phenylethynyl]-phenyl}-methanone, ethyl 3-{4-[5-(2,4-diamino-pyrimidin-5-ylmethyl)-2,3-dimethoxy-phenylethynyl]-phenyl}-3-oxo-propionate, ethyl [E/Z]-3-{4-[5-(2,4-diamino-pyrimidin-5-ylmethyl)-2,3-dimethoxy-phenylethynyl]-phenyl}-2-hydroxyimino-3-oxo-propionate, ethyl [E/Z]-3-{4-[5-(2,4-diamino-pyrimidin-5-ylmethyl)-2,3-dimethoxy-phenylethynyl)-phenyl}-2-(2-methoxy-ethoxyimino)-3-oxo-propionate, ethyl [E/Z]-3-{4-[5-(2,4-diamino-pyrimidin-5-ylmethyl)-2,3-dimethoxy-phenylethynyl]-phenyl}-2-methoxyimino-3-oxo-propionate, ethyl [E/Z]-3-{2-chloro-4-[5-(2,4-diamino-pyrimidin-5-ylmethyl)-2,3-dimethoxy-phenylethynyl]-phenyl}-3-oxo-2-trityloxyimino-propionate, N-[4-[5-(2,4-diamino-pyrimidin-5-ylmethyl)-2,3-dimethoxy-phenylethynyl]-phenyl]-C,C,C-trifluoro-methanesulphonamide, N-[4-[5-(2,4-diamino-pyrimidin-5-ylmethyl)-2,3-dimethoxy-phenyl-ethynyl]-phenyl]-C,C,C-trifluoro-N-(4-methoxy-benzyl)-methanesulphonamide 1:1 hydrochloride, N-[4-[5-(2,4-diamino-pyrimidin-5-ylmethyl)- 2,3-dimethoxy-phenylethynyl]-phenyl]-N-ethyl-C,C,C-trifluoro-methanesulphonamide 1:1 hydrochloride, N-[4-[5-(2,4-diamino-pyrimidin-5-ylmethyl)-2,3-dimethoxy-phenylethynyl]-phenyl]-N-isobuthyl-C,C,C-trifluoro-methanesulphonamide, N-[4-[5-(2,4-diamino-pyrimidin-5-ylmethyl)-2,3-dimethoxy-phenyl-ethynyl]-phenyl]-N-isobutyl-C,C,C-trifluoro-methanesulphonamide, ethyl [4-[5-(2,4-diamino-pyrimidin-5-ylmethyl)-2,3-dimethoxy-phenylethynyl]-phenyl]-trifluoro-methylsulphonyl)-amino]-acetate, N-[3-[5-(2,4-diamino-pyrimidin-5-ylmethyl)-2,3-dimethoxy-phenylethynyl]-phenyl]-N-methyl-C,C,C-trifluoro-methanesulphonamide, N-[3-[5-(2,4-diamino-pyrimidin-5-ylmethyl)-2,3-dimethoxy-phenylethynyl]-phenyl] -N-ethyl-C,C,C-trifluoro-methanesulphonamide, 5-[3,4-dimethoxy-5-(2-naphthalen-2-ylethynyl)-benzyl]-pyrimidine-2,4-diamine, 5-[3,4-dimethoxy-5-(phenylethynyl)-benzyl]-pyrimidine-2,4-diamine, 6-[5-(2,4-diaminopyrimidin-5-ylmethyl)-2,3-dimethoxy-phenylethynyl]-naphthalen-2-ol, 4-[5-(2,4-diamino-pyrimidin-5-ylmethyl)-2,3-dimethoxy-phenylethynyl]-2-hydroxy-benzoic acid hydrochloride, 5-[5-(2,4-diamino-pyrimidin-5-ylmethyl)-2,3-dimethoxy-phenylethynyl]-2-hydroxy-benzoic acid hydrochloride, 3-[5-(2,4-diamino-pyrimidin-5-ylmethyl)-2,3-dimethoxy-phenylethynyl]-4-hydroxymethyl-6-methoxy-phenol, 6-[5-(2,4-diamino-pyrimidin-5-ylmethyl)-2,3-dimethoxy-phenylethynyl]-naphthalen-1,7-diol,

[3-[5-(2,4-diamino-pyrimidin-5-ylmethyl)-2,3-dimethoxyphenylethynyl]-4,5-dimethoxy-phenyl]-methanol, 3-[5-(2,4-diamino-pyrimidin-5-ylmethyl)-2,3-dimethoxy-phenylethynyl]-4,5-dimethoxy-benzoic acid hydrochloride, ([3-[5-(2,4-diamino-pyrimidin-5-ylmethyl)-2,3-dimethoxy-phenylethynyl]-phenylcarbamic acid hydrochloride, monoethyl [4-[5-(2,4-diamino-pyrimidin-5-ylmethyl)-2,3-dimethoxy-phenylethynyl]-phenyl]-phosphonate,

[4-[5-(2,4-diamino-pyrimidin-5-ylmethyl)-2,3-dimethoxy-phenylethynyl]-phenyl]-phosphonic acid, ethyl [E/Z]-2-{2-chloro-4-[5-(2,4-diamino-pyrimidin-5-ylmethyl)-2,3-dimethoxy-phenylethynyl]-benzoyl}-3-ethoxy-acrylate,

[E/Z]-3-{4-[5-(2,4-diamino-pyrimidin-5-ylmethyl)-2,3-dimethoxy-phenylethynyl]-phenyl}-2-hydroxyimino-3-oxo-propionic acid, 4-[5-(2,4-diamino-pyrimidin-5-ylmethyl)-2,3-dimethoxy-phenylethynyl]-benzoic acid, ethyl [E/Z]-3-{2-chloro-4-[5-(2,4-diamino-pyrimidin-5-ylmethyl)-2,3-dimethoxy-phenylethynyl]-phenyl}-2-hydroxyimino-3-oxo-propionate, acid

[4-(5-(2,4-diamino-pyrimidin-5-ylmethyl)-2,3-dimethoxy-phenylethynyl]-phenyl]-trifluoromethylsulphonyl)-amino]-acetic acid.

25. The compound according to claim 4, selected from the group consisting of:

ethyl 1-cyclopropyl-7-[5-(2,4-diamino-pyrimidin-5-ylmethyl)-2,3-dimethoxy-phenylethynyl]-6,8-difluoro-4-oxo-1,4-dihydro-quinoline-3-carboxylate, ethyl 1-cyclopropyl-7-[5-(2,4-diamino-pyrimidin-5-ylmethyl)-2,3-dimethoxy-phenylethynyl]- 6-fluoro-4-oxo-1,4-dihydro-quinoline-3-carboxylate, methyl 6-[5-(2,4-diamino-pyrimidin-5-ylmethyl)-2,3-dimethoxy-phenylethynyl]-nicotinate, ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate, ethyl 7-[5-(2,4-diamino-pyrimidin-5-ylmethyl)-2,3-dimethoxy-phenylethynyl]-4-oxo-1-propyl-1,4-dihydro-quinoline-3-carboxylate, ethyl 1-cyclopropylmethyl-7-[5-(2,4-diamino-pyrimidin-5-ylmethyl)-2,3-dimethoxy-phenylethynyl]-4-oxo-1-propyl-1,4-dihydro-quinoline-3-carboxylate, ethyl 1-7-[5-(2,4-diamino-pyrimidin-5-ylmethyl)-2,3-dimethoxy-phenylethynyl]-1-(2-hydroxy-ethyl)-4-oxo-1,4-dihydro-quinoline-3-carboxylate, ethyl 7-[5-(2,4-diamino-pyrimidin-5-ylmethyl)-2,3-dimethoxy-phenylethynyl]-1-{2-[2-(2-hydroxy-ethoxy)-ethoxy]-ethyl}-4-oxo-1,4-dihydro-quinoline-3-carboxylate, ethyl 7-[5-(2,4-diamino-pyrimidin-5-ylmethyl)-2,3-dimethoxy-phenylethynyl]-4-oxo-1-pyridin-4-ylmethyl-1,4-dihydro-quinoline-3-carboxylate, ethyl 7-[5-(2,4-diamino-pyrimidin-5-ylmethyl)-2,3-dimethoxy-phenylethynyl]-1-ethyl-4-oxo-1,4-dihydro-[1,8]naphthyridine-3-carboxylate, ethyl 1-cyclopentyl-7-[5-(2,4-diamino-pyrimidin-5-ylmethyl)-2,3-dimethoxy-phenylethynyl]-4-oxo-1,4-dihydro-quinoline-3-carboxylate, ethyl 1-adamantan-1-yl-7-[5-(2,4-diamino-pyrimidin-5-ylmethyl)-2,3-dimethoxy-phenylethynyl]-4-oxo-1,4-dihydro-quinoline-3-carboxylate, ethyl ( )-1-bicyclo[2.2.1]hept-2-yl-7-[5-(2,4-diamino-pyrimidin-5-ylmethyl)-2,3-dimethoxy-phenylethynyl]-4-oxo-1,4-dihydro-quinoline-3-carboxylate, ethyl 7-[5-(2,4-diamino-pyrimidin-5-ylmethyl)-2,3-dimethoxy-phenylethynyl]-4-oxo-(1,1,3,3-tetramethylbutyl)-1,4-dihydro-quinoline-3-carboxylate, ethyl 1-tert-butyl-7-[5-(2,4-diamino-pyrimidin-5-ylmethyl)-2,3-dimethoxy-phenylethynyl]-4-oxo-1,4-dihydro-quinoline-3-carboxylate, ethyl 1-(trans-4-tert-butoxycarbonylamino-cyclohexyl)-7-[5-(2,4-diamino-pyrimidin-5-ylmethyl)-2,3-dimethoxy-phenylethynyl]-4-oxo-1,4-dihydro-quinoline-3-carboxylate, ethyl 7-[5-(2,4-diamino-pyrimidin-5-ylmethyl)-2,3-dimethoxy-phenylethynyl]-4-oxo-1-piperidin-4-ylmethyl-1,4-dihydro-quinoline-3-carboxylate, ethyl 1-cyclopropyl-7-[5-(2,4-diamino-pyrimidin-5-ylmethyl)-2,3-dimethoxy-phenylethynyl]-4-oxo-1,4-dihydro-quinoline-3-carboxylate, ethyl 7-[5-(2,4-diamino-pyrimidin-5-ylmethyl)-2,3-dimethoxy-phenylethynyl]-4-oxo-1-(2,2,2-trifluoro-ethyl)-1,4-dihydro-quinoline-3-carboxylate, ethyl 7-[5-(2,4-diamino-pyrimidin-5-ylmethyl)-2,3-dimethoxy-phenylethynyl]-4-oxo-1-phenyl-1,4-dihydro-quinoline-3-carboxylate, 1-ethyl-7-[5-(2,4-diamino-pyrimidin-5-ylmethyl)-2,3-dimethoxy-phenylethynyl]-4-oxo-1,4-dihydro-quinoline-3-carboxylic acid (3-dimethylamino-propyl)-amide, 1-ethyl-7-[5-(2,4-diamino-pyrimidin-5-ylmethyl)-2,3-dimethoxy-phenylethynyl]-4-oxo-1,4-dihydro-quinoline-3-carboxylic acid-(2-hydroxy-ethyl)-amide, 2-dimethylamino-ethyl 1-ethyl-7-[5-(2,4-diamino-pyrimidin-5-ylmethyl)-2,3-dimethoxy-phenylethynyl]-4-oxo-1,4-dihydro-quinoline-3-carboxylate, 2-diisopropylamino-ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate, 2-morpholin-4-yl-ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate, ethyl 1-cyclohexyl-7-[5-(2,4-diamino-pyrimidin-5-ylmethyl)-2,3-dimethoxy-phenylethynyl]-8-methoxy-4-oxo-1,4-dihydro-quinoline-3-carboxylate, 1-ethyl-7-5-(2,4-diamino-pyrimidin-5-ylmethyl)-2,3-dimethoxy-phenylethynyl]-4-oxo-1,4-dihydro-quinoline-3-carboxamide, 4-amino-N-{6-[5-(2,4-diamino-pyrimidin-5-ylmethyl)-2,3-dimethoxy-phenylethynyl]-2-methoxy-pyridin-3-yl}-benzene-sulphonamide, ethyl 1-cyclohexyl-7-[5-(2,4-diamino-pyrimidin-5-ylmethyl)-2,3-dimethoxy-phenylethynyl]-6,8-difluoro-4-oxo-1,4-dihydro-quinoline-3-carboxylate, ethyl 7-[5-(2,4-diamino-pyrimidin-5-ylmethyl)-2,3-dimethoxy-phenylethynyl]-6,8-difluoro-4-oxo-1-phenyl-1,4-dihydro-quinoline-3-carboxylate, 5-[5-(2,4-diaminopyrimidin-5-ylmethyl)-2,3-dimethoxy-phenylethynyl]-1H-indole-2,4-dione, 5-(5-(2,4-diaminopyrimidin-5-ylmethyl)-2,3-dimethoxy-phenylethynyl]-1-benzyl-indole-2,4-dione, 5-[5-(2,4-diamino-pyrimidin-5-ylmethyl)-2,3-dimethoxy-phenylethynyl)-1H-indole-2,3-dione 3-oxime, 5-[5-(2,4-diamino-pyrimidin-5-ylmethyl)-2,3-dimethoxy-phenylethynyl)-1-benzyl-indole-2,3-dione-3 oxime, ethyl 7-[5-(2,4-diamino-pyrimidin-5-ylmethyl)-2,3-dimethoxy-phenylethynyl]-4-oxo-1-(tetrahydrofuran-2-ylmethyl)-1,4-dihydro-quinoline-3-carboxylate, ethyl 7-[5-(2,4-diamino-pyrimidin-5-ylmethyl)-2,3-dimethoxy-phenylethynyl]-4-oxo-1-(furan-2-ylmethyl)-1,4-dihydro-quinoline-3-carboxylate, ethyl 7-[5-(2,4-diamino-pyrimidin-5-ylmethyl)-2,3-dimethoxy-phenylethynyl]-4-oxo-I-(tetrahydro-pyran-4-yl)-1,4-dihydro-quinoline-3-carboxylate, ethyl 1-[2-(tert-butyl-dimethyl-silanyloxy)-1,1-dimethyl-ethyl]-7-[5-(2,4-diamino-pyrimidin-5-ylmethyl)-2,3-dimethoxy-phenylethynyl]-4-oxo-1,4-dihydro-quinoline-3-carboxylate, (7S,8R,9R,10S,22S,23R,24R,25S)-7,8,9,10,22,23,24,25-octaacetoxy-3,18-bis-[5-(2,4-diamino-pyrimidin-5-ylmethyl)-2,3-dimethoxy-phenylethynyl]-5,6,7,8,9,10,20,21,22,23,24,25,26-tetracahydro-5,29:14,20-dimetheno-dibenzo[b,o][7,20,1,14]dioxadiazacyclohexacosin-13,15,28,30-tetraone, ethyl 1-ethyl-6-[5-(2,4-diamino-pyrimidin-5-ylmethyl)-2,3-dimethoxy-phenylethynyl]-4-oxo-1,4-dihydro-quinoline-3-carboxylate, ethyl 7-[5-(2,4-diamino-pyrimidin-5-ylmethyl)-2,3-dimethoxy-phenylethynyl]-4-hydroxy-quinoline-3-carboxylate, ethyl 7-[5-(2,4-diamino-pyrimidin-5-ylmethyl)-2,3-dimethoxy-phenylethynyl]-1-methyl-4-oxo-1,4-dihydro-quinoline-3-carboxylate, ethyl 1-benzyl-7-[5-(2,4-diamino-pyrimidin-5-ylmethyl)-2,3-dimethoxy-phenylethynyl]-1-methyl-4-oxo-1,4-dihydro-quinoline-3-carboxylate, ethyl (E)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylate, ethyl (E)-7-[2-[5-(2,4-diamino-pyrimidin-5-ylmethyl)-2,3-dimethoxy-phenyl]-vinyl]-1-cyclopropyl-6-fluoro-4-oxo-1,4-dihydro-quinoline-3-carboxylate, ethyl (E)-1-cyclohexyl-7-[2-[5-(2,4-diamino-pyrimidin-5-ylmethyl)-2,3-dimethoxy-phenyl]-vinyl]-4-oxo-1,4-dihydro-quinoline-3-carboxylate, ethyl (Z)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylate, ethyl 1-cyclopropyl-7-[2-[5-(2,4-diamino-pyrimidin-5-ylmethyl)-2,3-dimethoxy-phenyl]ethyl]-6,8-difluoro-4-oxo-1,4-dihydro-quinoline-3-carboxylate, (Z)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylic acid, 1-cyclopropyl-7-[5-(2,4-diamino-pyrimidin-5-ylmethyl)-2,3-dimethoxy-phenylethynyl]-6-fluoro-4-oxo-1,4-dihydro-quinoline-3-carboxylic acid trifluoroacetate, 1-ethyl-7-[5-(2,4-diamino-pyrimidin-5-ylmethyl)-2,3-dimethoxy-phenylethynyl]-6-fluoro-4-oxo-1,4-dihydro-quinoline-3-carboxylic acid hydrochloride, 6-[5-(2,4-diamino-pyrimidin-5-ylmethyl)-2,3-dimethoxy-phenylethynyl}-nicotinic acid hydrochloride, 1-ethyl-7-[5-(2,4-diamino-pyrimidin-5-ylmethyl)-2,3-dimethoxy-phenylethynyl]-4-oxo-1,4-dihydro-quinoline-3-carboxylic acid hydrochloride, (E)-7-2-(5-(2,4-diamino-pyrimidin-5-ylmethyl)-2,3-dimethoxy-phenyl]-vinyl]-1-cyclopropyl-6-fluoro-4-oxo-1,4-dihydro-quinoline-3-carboxylic acid, 1-ethyl-6-[5-(2,4-diamino-pyrimidin-5-ylmethyl)-2,3-dimethoxy-phenylethynyl]-4-oxo-1,4-dihydro-quinoline-3-carboxylic acid hydrochloride, 7-[5-(2,4-diamino-pyrimidin-5-ylmethyl)-2,3-dimethoxy-phenylethynyl]-4-hydroxy-quinoline-3-carboxylic acid hydrochloride, 7-[5-(2,4-diamino-pyrimidin-5-ylmethyl)-2,3-dimethoxy-phenylethynyl]-1-methyl-4-oxo-1,4-dihydro-quinoline-3-carboxylic acid hydrochloride, 1-cyclopropyl-7-[2-[5-(2,4-diamino-pyrimidin-5-ylmethyl)-2,3-dimethoxy-phenyl]ethyl]-6,8-difluoro-4-oxo-1,4-dihydro-quinoline-3-carboxylic acid hydrochloride, (E)-7-[2-[5-(2,4-diamino-pyrimidin-5-ylmethyl)-2,3-dimethoxy-phenyl]-vinyl]-1-cyclopropyl-6,8-difluoro-4-oxo-1,4-dihydro-quinoline-3-carboxylic acid hydrochloride, 1-cyclohexyl-7-[5-(2,4-diamino-pyrimidin-5-ylmethyl)-2,3-dimethoxy-phenylethynyl]-4-oxo-1,4-dihydro-quinoline-3-carboxylic acidchydrochloride, 7-[5-(2,4-diamino-pyrimidin-5-ylmethyl)-2,3-dimethoxy-phenylethynyl]-4-oxo-1-propyl-1,4-dihydro-quinoline-3-carboxylic acid hydrochloride, 1-cyclopropylmethyl-7-[5-(2,4-diamino-pyrimidin-5-ylmethyl)-2,3-dimethoxy-phenylethynyl]-4-oxo-1-propyl-1,4-dihydro-quinoline-3-carboxylic acid hydrochloride, 1-7-[5-(2,4-diamino-pyrimidin-5-ylmethyl)-2,3-dimethoxy-phenylethynyl]-1-(2-hydroxy-ethyl)-4-oxo-1,4-dihydro-quinoline-3-carboxylic acid hydrochloride, 7-[5-(2,4-diamino-pyrimidin-5-ylmethyl)-2,3-dimethoxy-phenylethynyl]-1-{2-[2-(2-hydroxy-ethoxy)-ethoxy]-ethyl}-4-oxo-1,4-dihydro-quinoline-3-carboxylic acid hydrochloride, 7-[5-(2,4-diamino-pyrimidin-5-ylmethyl)-2,3-dimethoxy-phenylethynyl]-4-oxo-1-pyridin-4-ylmethyl-1,4-dihydro-quinoline-3-carboxylic acid dihydrochloride, 7-[5-(2,4-diamino-pyrimidin-5-ylmethyl)-2,3-dimethoxy-phenylethynyl]-1-ethyl-4-oxo-1,4-dihydro-[1,8]naphthyridine-3-carboxylic acid hydrochloride, 1-cyclopentyl-7-[5-(2,4-diamino-pyrimidin-5-ylmethyl)-2,3-dimethoxy-phenylethynyl]-4-oxo-1,4-dihydro-quinoline-3-carboxylic acid hydrochloride, 1-adamantan-1-yl-7-[5-(2,4-diamino-pyrimidin-5-ylmethyl)-2,3-dimethoxy-phenylethynyl]-4-oxo-1,4-dihydro-quinoline-3-carboxylic acid hydrochloride, ( )-1-bicyclo-[2.2.1]hept-2-yl-7-[5-(2,4-diamino-pyrimidin-5-ylmethyl)-2,3-dimethoxy-phenylethynyl]-4-oxo-1,4-dihydro-quinoline-3-carboxylic acid hydrochloride, 7-[5-(2,4-diamino-pyrimidin-5-ylmethyl)-2,3-dimethoxy-phenylethynyl]-4-oxo-(1,1,3,3-tetramethyl-butyl)-1,4-dihydro-quinoline- 3-carboxylic acid hydrochloride, 1-tert-butyl-7-[5-(2,4-diamino-pyrimidin-5-ylmethyl)-2,3-dimethoxy-phenylethynyl]-4-oxo-1,4-dihydro-quinoline-3-carboxylic acid hydrochloride, ethyl 1-(trans-4-amino-cyclohexyl)-7-[5-(2,4-diamino-pyrimidin-5-ylmethyl)-2,3-dimethoxy-phenylethynyl]-4-oxo-1,4-dihydro-quinoline-3-carboxylate trifluoroacetate, 1-(trans-4-amino-cyclohexyl)-7-[5-(2,4-diamino-pyrimidin-5-ylmethyl)-2,3-dimethoxy-phenylethynyl]-4-oxo-1,4-dihydro-quinoline-3-carboxylic acid dihydrochloride, 7-[5-(2,4-diamino-pyrimidin-5-ylmethyl)-2,3-dimethoxy-phenylethynyl]-4-oxo-1-piperidin-4-ylmethyl-1,4-dihydro-quinoline-3-carboxylic acid hydrochloride, 1-cyclopropyl-7-[5-(2,4-diamino-pyrimidin-5-ylmethyl)-2,3-dimethoxy-phenylethynyl]-4-oxo-1,4-dihydro-quinoline-3-carboxylic acid hydrochloride, 7-[5-(2,4-diamino-pyrimidin-5-ylmethyl)-2,3-dimethoxy-phenylethynyl]-4-oxo-1-(2,2,2-trifluoro-ethyl)-1,4-dihydro-quinoline-3-carboxylic acid hydrochloride, 7-[5-(2,4-diamino-pyrimidin-5-ylmethyl)-2,3-dimethoxy-phenylethynyl]-4-oxo-1-phenyl-1,4-dihydro-quinoline-3-carboxylic acid hydrochloride, 1-Ethyl-7-[5-(2,4-diamino-pyrimidin-5-ylmethyl)-2,3-dimethoxy-phenylethynyl]-4-oxo-1,4-dihydro-quinoline-3-carboxylic acid (3-dimethylamino-propyl)-amide dimethanesulphonate, 2-dimethylamino-ethyl 1-ethyl-7-[5-(2,4-diamino-pyrimidin-5-ylmethyl)-2,3-dimethoxy-phenylethynyl]-4-oxo-1,4-dihydro-quinoline-3-carboxylate trimethanesulphonate, 2-diisopropylamino-ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate methanesulphonate, 2-morpholin-4-yl-ethyl 1-cyclohexyl-7-[5-(2,4-diamino-pyrimidin-5-ylmethyl)-2,3-dimethoxy-phenylethynyl]-4-oxo-1,4-dihydro-quinoline-3-carboxylate dimethanesulphonate, 1-cyclohexyl-7-[5-(2,4-diamino-pyrimidin-5-ylmethyl)-2,3-dimethoxy-phenylethynyl]-8-methoxy-4-oxo-1,4-dihydro-quinoline-3-carboxylic acid hydrochloride, (E)-1-cyclohexyl-7-[2-[5-(2,4-diamino-pyrimidin-5-ylmethyl)-2,3-dimethoxy-phenyl]-vinyl]-4-oxo-1,4-dihydro-quinoline-3-carboxylate hydrochloride, 1-cyclohexyl-7-{5-(2,4-diamino-pyrimidin-5-ylmethyl)-2,3-dimethoxy-phenylethynyl]-6,8-difluoro-4-oxo-1,4-dihydro-quinoline-3-carboxylic acid hydrochloride, 1-cyclohexyl-7-[5-(2,4-diamino-pyrimidin-5-ylmethyl)-2,3-dimethoxy-phenylethynyl]-6-fluoro-8-methoxy-4-oxo-1,4-dihydro-quinoline-3-carboxylic acid hydrochloride, 7-[5-(2,4-diamino-pyrimidin-5-ylmethyl)-2,3-dimethoxy-phenylethynyl]-6,8-difluoro-4-oxo-1-phenyl-1,4-dihydro-quinoline-3-carboxylic acid hydrochloride, 7-[5-(2,4-diamino-pyrimidin-5-ylmethyl)-2,3-dimethoxy-phenylethynyl]-4-oxo-1-(tetrahydrofuran-2-ylmethyl)-1,4-dihydro-quinoline-3-carboxylic acid hydrochloride, 7-[5-(2,4-diamino-pyrimidin-5-ylmethyl)-2,3-dimethoxy-phenylethynyl]-4-oxo-1-(tetrahydro-pyran-4-yl)-1,4-dihydroquinoline-3-carboxylic acid, ethyl 7-[5-(2,4-diamino-pyrimidin-5-ylmethyl)-2,3-dimethoxy-phenylethynyl]-1-(2-hydroxy-1,1-dimethyl-ethyl)-4-oxo-1,4-dihydro-quinoline-3-carboxylate, and 7-[5-(2,4-diamino-pyrimidin-5-ylmethyl)-2,3-dimethoxy-phenylethynyl]-4-oxo-1-(2,3,4,5,6-pentahydroxy-hexyl)-1,4-dihydro-quinoline-3-carboxylic acid.

26. The compound according to claim 1, wherein $R^3$ is a residue (c) or (d):

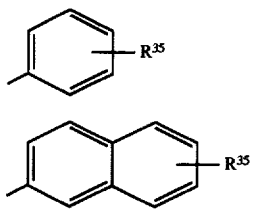

wherein $R^{35}$ is hydrogen, hydroxy or carboxy.

27. The compound according to claim 3, wherein $R^{30}$ is a residue (c) or (d):

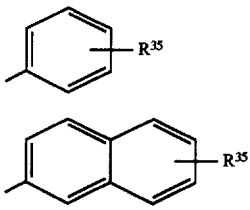

wherein $R^{35}$ is hydrogen, hydroxy or carboxy.

28. The compound according to claim 2, wherein $R^{32}$ is benzyl or tert.-butyl.

29. The compound according to claim 2, wherein $R^{33}$ is hydrogen or fluorine.

30. The compound according to claim 2, wherein $R^{34}$ is hydrogen or fluorine.

31. The compound according to claim 2, wherein $R^{32}$ is benzyl or tert.-butyl.

32. The compound according to claim 2, wherein $R^{33}$ is hydrogen or fluorine.

33. The compound according to claim 2, wherein $R^{34}$ is hydrogen or fluorine.

34. The compound according to claim 26, selected from the group consisting of:

5-(3,4-dimethoxy-5-naphthalen-2-yl-benzyl)-pyrimidine-2,4-diamine, 5-(3,4-dimethoxy-5-naphthalen-6-hydroxy-2-yl-benzyl)-pyrimidine-2,4-diamine, 5-(4'-carboxy-5,6-dimethoxy-biphenyl-3-ylmethyl)-pyrimidine-2,4-diamine, and 5-(3'-hydroxy-5,6-dimethoxy-biphenyl-3-ylmethyl)-pyrimidine-2,4-diamine.

35. The compound according to claim 27, selected from the group consisting of:

5-[3,4-dimethoxy-5-(2-naphthalen-2-yl-vinyl)-benzyl]-pyrimidine-2,4-diamine, and 5-[3,4-dimethoxy-5-(2-naphthalen-6-carboxy-2-yl-ethynyl)-benzyl]-pyrimidine-2,4-diamine.

36. A medicament which comprises:

a) a compound of the formula:

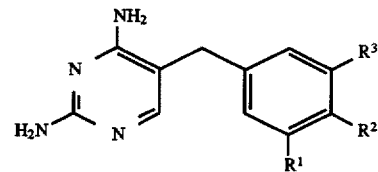

in which $R^1$ is lower alkoxy, $R^2$ is bromine or lower alkoxy, and $R^3$ is aryl, heteroaryl or a group —Q—$R^{30}$, wherein Q is ethylene, vinylene or ethynylene and $R^{30}$ is aryl, heteroaryl, lower alkoxycarbonyl or carbamoyl; hydrolyzable esters of carboxylic acids of formula I; and pharmaceutically acceptable salts of these compounds; and b) a therapeutically inert carrier.

* * * * *

UNITED STATES PATENT AND TRADEMARK OFFICE
CERTIFICATE OF CORRECTION

PATENT NO. : 5,763,450
DATED : June 9, 1998
INVENTOR(S) : Guerry, et al.

It is certified that error appears in the above-identified patent and that said Letters Patent is hereby corrected as shown below:

Claim 12, Column 66, line 9: " - phenyl3-6- " should read --- -phenyl]-6- ---.

Claim 15, Column 66, line 37: " bicyclco2.2.1] " should read --- bicyclo[2.2.1] ---.

Claim 22, Column 68, lines 10-11: " N-[5'-(2,4-diamino-pyrimidin-5-ylmethyl)-2',3'-dimethoxy-biphenyl-3-yl)-2-hydroxy-benzamid, " should read --- N-{5'-(2,4-diamino-pyrimidin-5-ylmethyl)-2',3'-dimethoxy- biphenyl-3-yl}-2-hydroxy-benzamid, ---.

Claim 23, Column 69, line 35: " -6-fluoro-⁴-oxo-1,4- " should read --- -6-fluoro-4-oxo-1,4- ---.

Signed and Sealed this

First Day of September, 1998

Attest:

BRUCE LEHMAN

*Attesting Officer*   *Commissioner of Patents and Trademarks*